(12) United States Patent
Morsey et al.

(10) Patent No.: US 6,759,393 B1
(45) Date of Patent: Jul. 6, 2004

(54) GROWTH HORMONE AND GROWTH HORMONE RELEASING HORMONE COMPOSITIONS

(75) Inventors: Mohamad A. Morsey, Niantic, CT (US); Michael G. Sheppard, North Stonington, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/628,730

(22) Filed: Jul. 28, 2000

Related U.S. Application Data

(63) Continuation of application No. 09/546,411, filed on Apr. 11, 2000, now abandoned.
(60) Provisional application No. 60/128,830, filed on Apr. 12, 1999.

(51) Int. Cl.[7] .......................... A61K 48/00; C07H 21/04
(52) U.S. Cl. .......................... 514/44; 536/24.1; 536/23.1
(58) Field of Search .............................. 536/23.4, 24.1; 514/44; 435/320.1, 325, 455, 458; 424/93.1, 2

(56) References Cited

U.S. PATENT DOCUMENTS

| | | |
|---|---|---|
| 3,818,911 A | 6/1974 | Fournier |
| 3,995,633 A | 12/1976 | Gougeon |
| 4,341,728 A | 7/1982 | Robertson et al. |
| 4,980,286 A | 12/1990 | Morgan et al. |
| 4,988,512 A | 1/1991 | Azria |
| 5,298,422 A | 3/1994 | Schwartz et al. |
| 5,436,146 A | 7/1995 | Shenk et al. |
| 5,756,264 A | 5/1998 | Schwartz et al. |
| 5,854,216 A | 12/1998 | Gaudreau |
| 6,423,693 B1 * | 7/2002 | Schwartz et al. ............. 514/44 |

FOREIGN PATENT DOCUMENTS

| | | |
|---|---|---|
| EP | 0199018 | 10/1986 |
| EP | 715847 | 6/1996 |
| EP | 1052286 | 11/2000 |
| GB | 1495735 | 12/1977 |
| GB | 2154875 | 9/1985 |
| WO | 8100356 | 2/1981 |
| WO | 8804544 | 6/1988 |
| WO | 9208180 | 4/1992 |
| WO | 9210576 | 6/1992 |
| WO | 9220316 | 11/1992 |
| WO | 9222635 | 12/1992 |
| WO | 9314188 | 7/1993 |
| WO | 9315788 | 8/1993 |
| WO | 9319698 | 10/1993 |
| WO | 9320221 | 10/1993 |
| WO | 9408598 | 4/1994 |
| WO | 9412649 | 6/1994 |
| WO | 9601092 | 1/1996 |
| WO | 9637514 | 11/1996 |
| WO | 9715242 | 5/1997 |
| WO | WO 99/05300 | * 2/1999 |
| WO | 9905300 | 2/1999 |

OTHER PUBLICATIONS

Ornitz et al.; Elastase I Promoter Directs Expression of Human Growth Hormone and SV40 T Antigen Genes to Pancreatic Acinar Cells in Transgenic Mice, 1988, Cold Spring Symp.Quart.Bio. 50: 399–409.*
Miller et.al.; Targeted vectors for gene therapy, 1995, FASEB J. 9: 190–199.*
Verma et al.; Gene therapy–promises, problems and prospects, 1997, Nature, vol. 389: 239–242.*
Orkin et.al.; Report and Recommendations of the Panel to Assess the NIH Investment in Research on Gene Therapy, 1995.*
Felix, et al.; Pegylated Peptides IV Enhanced Biological Activity of site–directed pegylated GRF analogs; Int. J. Peptide Protein Research; vol. 46 pp. 253–264 (1995).
Reecy, et al.; Structure and regulation of the porcine skeletal α–actin–encoding gene; GENE 180 pp. 23–28 (1996).
Kubiak, et al.; Position 2 and Position 2/Ala$^{15}$ –Substituted Analogs of Bovine Growth Hormone–Releasing Factor (bGRF) with Enhanced Metabolic Stability and Improved in Vivo Bioactivity; J. Med. Chem. vol. 36, pp. 888–897 (1993).
Breedam, et al.; Amidation of Growth Hormone releasing factor (1–29) by serine carboxypeptidase catalysed transpeptidation; Int. J. Peptide Protein Res.; vol. 37, pp. 153–160 (1991).
Draghia–Akli, et al; Enhanced growth by ectopic expression of growth hormone releasing hormone using an injectable myogenic vactor; Nature Biotechnology, vol. 15, pp. 1285–1289 (1997).
Hoffman, et al.; Inhibition of dipeptidyl peptidase IV (DP IV) by anti–DP IV antibodies and non–substrate X–X–Pro–oligopeptides ascertained by capillary electrophoresis; J. of Chromatogrpahy A; vol. 716 pp. 355–362 (1995).
Brar, et al.; Biosynthesis of Human Growth Hormone–Releasing Hormone (hGRH) in the Pituitary of hGRH Transgenic Mice; (1991) Endocrinolgoy 129:3274–3280.
Arase, et al.; Effects on Feeding Behavior of Rats of a Cryptic Peptide from the C–Terminal End of Prepro–Growh Hormone–Releasing Factor; (1987) Endocrinology 121: 1960–1965.
Vance; Growth–Hormone–Releasing Hormone; (1990) Clin. Chem. 36/3: 415–420.

(List continued on next page.)

Primary Examiner—Ram R. Shukla
(74) Attorney, Agent, or Firm—Paul H. Ginsburg; Lorraine B. Ling; Kohn & Associates, PLLC

(57) ABSTRACT

The present invention relates to methods and compositions of growth hormone and/or growth hormone releasing hormone that promote of the release and the elevation of growth hormone when administered to animals. The present invention further relates to methods and compositions of growth hormone and/or growth hormone releasing hormone for treatment of diseases or disorders resulting from growth hormone related deficiencies. The invention also provides methods for producing novel growth hormone releasing hormone variants and their uses thereof.

1 Claim, 5 Drawing Sheets

OTHER PUBLICATIONS

Frohman, et al.; Dipeptidylpeptidase IV and Trypsin–like Enzymatic Degradation of Human Growth Hormone–releasing Hormone in Plasma; (1989) J. Clin. Invest. 83: 1533–1540.

Etherton, et al.; Biotgy of Somatotropin in Growth and Lactation of Domestic Animals; (1998) Physiological reviews 78: 745–761.

Etherton; Growth Hormone Technology Develops New Twist; Nature Biotechnology 15: 1248.

Benoist, et al.; In Vivo Sequence Requirements of the SV40 Early Promoter Region; (1981) Nature 290: 304–310.

Yamamoto, et al.; Identification of a Functional Promoter in the Long Terminal Repeat of Rous Sarcoma Virus; (1980) Cell 22: 787–797.

Wagner, et al.; Nucleotide Sequence of the Thymidine Kinase Gene of Herpes Simplex Virus Type 1; Proc. Natl. Acad. USA 78: 1441–1445.

Brinster, et al.; Regulation of Metallothionein–Thymidine Kinase Fusion Plasmids Injected into Mouse Eggs; (1982) Nature 296: 39–42.

Villa–Kamaroff, et al.; A Bacterial Clone Synthesizing Proinsulin; (1978) Proc. Natl. Acad. Sci. USA 75: 3727–3731.

DeBoer, et al.; The Tac Promoter: A Functional Hybrid Derived from the trp and Iac Promoters; (1983) Proc. Natl. Acad. Sci. USA 80: 21–25.

Herrera–Estrella, et al.; Expression of Chimaeric Genes Transferred into Plant cell Using a Ti–plasmid–derived Vector; Nature 303: 209–213.

Herrera–Estrella, et al.; Light–Inductible and Chloroplast–Associated Expression of a Chimaeric Gene Introduced into Nicotiana Tabacum Using a Ti Plasmid Vector; Nature 310: 115–120.

Gardner, et al.; Abstract; (1981) Nucleic Acid Research; 9: 2871–2888.

Swift, et al.; Tissue–Specific Expression of the Rat Pancreatic Elastase I Gene in Transgenic Mice; (1984) Cell 38: 639–646.

Omitz, et al.; Elastase I Promoter Directs Expression of Human Growth Hormone and SV40 T Antigen Genes to Pancreatic Acinar Cells in Transgenic Mice; 1986) Cold Sprin Harbor Symp. Quant. Bio. 50: 399–409.

McDonald, et al.; Diminished Responsiveness of Male Homosexual Chronic Hepatits B Virus Carriers with HTLV–III Antibodies to Recombinant α–Interferon; (1987) Hepatology 7: 719–723.

Grosschedl, et al.; Introduction of a μ Immunoglobulin Gene Into the Mouse Gem Line: Specific Expression in Lymphoid Cells and synthesis of Functional Antibody; (1984) 38:647–658.

J.M. Adams, et al.; The c–myc Onocogene Driven by Immunoglobulin Enhancers Induces Lymphoid Mallgnancy in Transgenic Mice; (1985) Nature 318: 533–538.

Alexander, et al.; Expression of the c–myc Oncogene Under Control of an Immunoglobulin Enhancer in Eμ–myc Transgenic Mice; (1987) Mol. Cellular Biology; 7: 1436–1444.

Leder, et al.; Consequences of Widespread Deregulation of the c–myc Gene in Transgenic Mice: Multiple Neoplasms and Normal Development; (1986) Cell 45: 485–495.

Pinkert, et al.; An Albumin Enhancer Located 10 kb Upstream Functions along with its Promoter to Direct Efficient, Liver–Specific Expression in Transgenic Mice; (1987) Genes and Devel. 1:268–276.

Krumlauf, et al.; Development Regulation of α–Fetoprotein Genes In Transgenic Mice; (1985) Mol. Cell. Bio. 5: 1639–1648.

Hammer, et al.; Diversity of Alpha–Fetoprotein Gene Expression in Mice Is Generated by a Combination of Separate Enhancer Elements; (1987) Science 235: 53–58.

Kelsey, et al.; Species and Tissue–Specific Expression of Human $α_1$–Antitrypsin Mice; (1987) Genes Devel. 1: 161–171.

Magram, et al.; Developmental Regulation of a Cloned Adult β–Globin Gene in Transgenic Mice; (1985) Nature 315: 338–340.

Kollias, et al.; Regulated Expression of Human $^Aγ$–, β–, and Hybrid γβ–Globin Genes in Transgenic Mice; Manipulation of the Developmental Expression Patterns; (1986) Cell 46: 89–94.

Readhead, et al.; Expression of a Myelin Basic Protein Gene In Transgenic Shiverer Mice; Correction of the Dysmyelinating Phenotype; (1987) Cell 48: 703–712.

Shani; Tissue–Specific Expression of Rat Myosin Light–Chain 2 Gene in Transgenic Mice; (1985) Nature 314: 283–286.

Reecy, et al.; Multiple Regions of the Porcine α–Skeletal Actin Gene Modulate Muscle–Specific Expression in Cell culture and Directly Injected Skeletal Muscle; (1998) Animal Biotechnology 9: 101–120.

Mason, et al.; The Hypogonadal Mouse: Reproductive Functions Restored by Gene Therapy: (1986) Science 234: 1372–1378.

Wigler, et al.; Transfer of Purified Herpes Virus Thymidine Kinase Gene to Cultured Mouse Cells; (1977) Cell 11: 223–232.

Szybalska & Szybalski; Genetics of Human Cell Lines, IV. DNA–Mediated Heritable Transformation of Biochemical Trait; (1962) Proc. Natl. Acad. Sci. USA 48: 2026.

Lowy, et al.; Isolation of Transforming DNA: Cloning the Hamster Aprt Gene; (1980) Cell 22: 817–823.

Wigler, et al.; Transformation of Mammalian with an Amplifiable Dominant–Acting Gene; (1980) Natl. Acad. Sci. 77:3567–3570.

O'Hare, et al.; Transformation of Mouse Fibroblasts to Methotrexate Resistance by a Recombinant Plasmid Expressing a Prokarytoci Dehydrofolate Reductase; (1981) Proc. Natl. Acad. Sci. USA 78: 1527–1531.

Mulligan, et al.; Selection for Animal Cells that Express the *Escherichia Coli* Gene Coding for Xanthine–Guanine Phosphoribosytransferase; (1981) Proc. Natl. Acad. Sci. USA 78: 2072–2076.

Colbere–Garapin, et al.; A New Dominant Hybrid Selective Marker for Higher Eukaryotic Cells; (1981) J. Mol. Biol. 150: 1–14.

Santerre, et al.; Expression of Prokaryotic Genes for Hygromycin B and G418 Resistance as Dominant–Selection Markers in Mouse L Cells; (1984) Gene 30: 147–156.

Goldspiel, et al.; Human Gene Therapy; (1993) Clinical Pharmacy 12: 488–505.

Wu, et al.; Delivery Systems for Gene Therapy (1991) Biotherapy 3: 87–95.

Tolstoshev; Gene Therapy, Concepts, Current Trials and Future Directions: (1993) Ann. Rev. Pharmacol. Toxicol. 32: 573–596.

Mulligan; The Basic Science of Gene Therapy; (1993) Science 260: 926–932.

Morgan, et al.; Human Gene Therapy; (1993) Annual Rev. Biochem. 62: 191–217.

Editorial; Gene Therapy—Proceeding from Laboratory to Clinic; (1993) Tibtech 11(5) 155–215.

Koller, et al.; Inactivating the $\beta_2$–microglobulin Locus in Mouse Embryonic Stem Cells by Honologous Recombination; (1989) Proc. Natl. Acad. Sci. USA 86: 8932–8935.

Zijlstra, et al.; Gem–line Transmission of a distrupted $\beta_2$–microglobulin Gene Produced by Homologous Recomination in Embryonic Stem Cells; (1989) Nature 342: 435–438.

Wu, et al.; Receptor–Mediated in Vitro Gene Transformation by a Soluble DNA Carrier System; (1987) J. biologcial Chem. 262: 4429–4432.

Miller, et al.; Use of Retroviral Vectors for Gene Transfer and Expression; (1993) Methods in Enzymology 217: 581–599.

Boesen, et al.; Circumvention of Chemotherapy–Induced Myelosuppression by Transfer of the mdr1 Gene; (1994) Biotherapy 6: 291–302.

Clowes, et al.; Long–Term Biological Response of Injured Rat Carotid Artery Seeded with Smooth Muscle Cells Expressing Retrovirally Introduced Human Genes; (1994) J. Clin. Invest. 93: 644–651.

Kiern, et al.; Retrovirus–Mediated Gene Transduction Into Canine Peripheral Blood repopulating Cells; (1994) Blood 83: 1467–1473.

Grossman, et al.; Retroviruses: Delivery Vehicle to the Liver; (1993) Current Opin. in Genetics and Devel. 3: 110–114.

Bout, et al.; Lung Gene Therapy: In Vivo Adenovirus–Mediated Gene Transfer to Rhesus Monkey Airway Epithelium; (1994) Human Gene Therapy 5: 3–10.

Rosenfeld, et al.; Adenovirus–Mediated Transfer of a Recombinant $\alpha 1$–Antitrypsin Gene to the Lung Epithelium in Vivo; (1991) Science 252: 431–434.

Rosenfeld, et al.; In Vivo Transfer of the Human Cystic Fibrosis Transmembrane Conductance Regulator Gene to the Airway Epithelium; (1992) Cell 68: 143–155.

Mastrangeli, et al.; Diversity of Airway Epithelial Cell Targets for in Vivo Recombinant Adenovirus–Mediated Gene Trasnfer; (1993) J. Clin. Investigation 91: 225–234.

Wang, et al.; A Packaging Cell Line for Propagation of Recombinant Adenovirus Vectors Containing two Lethal Gene–region Deletions; (1995) Gene Therapy 2: 775–783.

Walsh, et al.; Gene Therapy for Human Hemoglobinopathies; (1993) Proc. Soc. Exp. Biolo. Med. 204: 289–300.

Loeffler, et al.; Gene Transfer into Primary and Established Mammalian Cell Lines with Lipopolyamine–Coated DNA; (1993) Methods in Enzymology 217: 599–618.

Cotton, et al.; Receptor–Mediated Transport of DNA into Eukaryotic Cells; (1993) Methods in Enzymol. 217: 618–644.

Cline; Perspectives for Gene Therapy: Inserting New Genetic Information into Mammalian Cells by Physical Techniques and Viral Vectors; (1985) Pharmac. Ther. 29:69–92.

Stemple, et al.; Isolation of Stem Cell for Neurons and Glia From the Mammalian Neural Crest; (1992) Cell 71: 973–985.

Rheinwald; Serial Cultivation of Normal Human Epidermal Keratinocytes; (1980) Methods in Cell Biology 21A: 229–254.

Pittelkow, et al.; New Techniques for the in Vitro Culture of Human Skin Keratinocytes and Perspectives on Their Use for Grafting of Patients with Extensive Burns; (1986) Mayo Clinc Proc. 61: 771–777.

Langer; New Methods of Drug Delivery; Science (1990) 249: 1527–1533.

Treat, et al.; Liposome Encapsulated Doxorubicin Preliminary Results of Phase I and II Trials; Liposomes in the Therapy of Infectious Disease and Cancer (1989) 353–365.

Lopez–Berestein; Treatment of Systemic Fungal Infections with Liposoml–amphotericin B; Liposomes in the Therapy of Infectious Disease and Cancer; 317–327.

Sefton; Implantable Pumps; CRC Critical Reviews in Biomed. Engineering 14: 201–240.

Buchwald, et al.; Long–Term Continuous Intravenous Heparing Administration by an Implantable infusion Pump In Ambulatory Patients with Recurrent Venous Thrombosis; (1980) SUrgery 88: 507–516.

Saudek, et al.; A Preliminary Trial of the Programmable Implantable Medication System for Insulin Delivery; (1989) The New England J. of Medicine 321: 574–579.

Langer, et al.; Chemical and Physical Structure of Polymers as Carriers for Controlled Release of Bioactive Agents: A Review; (1983) J. Macromol. Chem. Phys. 23:61–126.

Abstract, Science 228: (1985) 190–192.

During, et al.; Controlled Release of Dopamine From a Polymeric Brain Implant in Vivo Characterization; (1989) Ann. Neurol. 25: 351–356.

Howard, et al.; Intracerbral Drug Delivery in Rats with Lesion–Induced Memory Deficits; (1989) J. Neurosurg. 71: 105–112.

Goodson; (1984) Dental Applications; Medical Applications of Controlled Release, vol. II 115–138.

Joliot, Proc. Natl. Acad. Sci, USA (1991) 1864–1868.

* cited by examiner

SEQUENCE LISTING

<160> NUMBER OF SEQ ID NOS: 67

<210> SEQ ID NO 1
<211> LENGTH: 246
<212> TYPE: DNA
<213> ORGANISM: Artificial Sequence
<220> FEATURE:
<223> OTHER INFORMATION: Description of Artificial Sequence: oligonucleotide

<400> SEQUENCE: 1

```
ggatccgcca ccatgccact ctgggtgttc ttctttgtga tcctcaccct cagcaacagc      60
tcccactgct ccccacctcc ccctttgacc ctcaggatgc ggcggtatgc agatgccatc     120
ttcaccaaca gctaccggaa ggtgctgggc cagctgtccg cccgcaagct gctccaggac     180
atcatgagca ggcagcaggg agagagaaac caagagcaag gagcaagggt gcggctttga     240
agatct                                                                246
```

<210> SEQ ID NO 2
<211> LENGTH: 75
<212> TYPE: PRT
<213> ORGANISM: Artificial Sequence
<220> FEATURE:
<223> OTHER INFORMATION: Description of Artificial Sequence: GHRH protein

<400> SEQUENCE: 2

```
Met Pro Leu Trp Val Phe Phe Phe Val Ile Leu Thr Leu Ser Asn Ser
 1               5                  10                  15

Ser His Cys Ser Pro Pro Pro Leu Thr Leu Arg Met Arg Arg Tyr
             20                  25                  30

Ala Asp Ala Ile Phe Thr Asn Ser Tyr Arg Lys Val Leu Gly Gln Leu
         35                  40                  45

Ser Ala Arg Lys Leu Leu Gln Asp Ile Met Ser Arg Gln Gln Gly Glu
     50                  55                  60

Arg Asn Gln Glu Gln Gly Ala Arg Val Arg Leu
 65                  70                  75
```

<210> SEQ ID NO 3
<211> LENGTH: 685
<212> TYPE: DNA
<213> ORGANISM: Artificial Sequence
<220> FEATURE:
<223> OTHER INFORMATION: Description of Artificial Sequence: obligonucleotide

<400> SEQUENCE: 3

```
ggtaccatcg ctggggagct ggggagggg tcgccttcct gccctaccca ggactccggg      60
tgcgaccgct cctctatctc tccagcccac caccactcca ccacttggac acgtctccct     120
cctccctgga gtcgctctag agggtttggg ggtctgagta agaacccga agtagggata     180 cagtgtggcg gcaccttcca gaggccccgg gcgcagggta ccgggggcg gggcggcccg     240 cggacaggtg cagccccagg cgcaggcgca ctcgcgcctc ccggcgcagg cggtgaacct     300
cgccccaccc cagcccctcc gggggcagc tgggccgggt cggaggggc ccaccagccc      360 gggagacact ccatatacgg ccaggcccgc tttacctggg ctccggccag ccgctccttt     420
ctttggtcag cacaggggac ccgggcgggg gcccaggccg ctaacccgcc ggggagggg     480 gctccagtgc ccaacaccca aatatggctc gagaagggga gcgacattcc agtgaggcgg     540
```

```
ctcgggggga aacccgcgg gctatataaa acctgagcgt ggggaccagc ggccaccgca    600
gcggacagcg ccgagagaag cctcgcttcc ctcccgcggc gaccagggcc ccagccggag    660
agcagcaggt gtagccacca agctt                                          685
```

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 4

```
aatcccaagc ttgccaccat gccactctgg                                      30
```

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 5

```
tattgctcta gatcaaagcc gcacccttgc                                      30
```

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 6

```
cgggtaccat cgctggggga gctggggcag gggtcgcct                            39
```

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 7

```
cccgcttggt ggctacacct gctgctctcc ggctggggcc                           40
```

<210> SEQ ID NO 8
<211> LENGTH: 2014
<212> TYPE: DNA
<213> ORGANISM: Artificial Sequence
<220> FEATURE:
<223> OTHER INFORMATION: Description of Artificial Sequence: SK 2014

<400> SEQUENCE: 8

```
ggtaccgcta taggagagaa aagagctgca ctgagcaccc tccttcccct ttaaatgtca     60
acagattagg agtcagtgaa tgacagcaca cctcttgcta ccttagagac caaaatttaa    120
gctactcccc ttaagctata gctagagtgc acctgccagt gtctttagtc cccactgatg    180
gaacaggacc caaggtattg aagatggaac atagttattc attcatcctc taatttaaaa    240
agctggatat gctgtacagc agaaattgac ggaacaatgt aaatcaacta taacagaaga    300
aataaaaacc tgggggggaaa gaagctgact atgaaacccc aggagctttc tacatgggcc    360
tggactcacc aaactctttta ttttgtaatg gacttctgac attttaggaa agggctgtcc    420
```

```
tgatgtgggc tatagaagag ggtttcacat gcttcttcaa gaggacccac actgtcccag      480
ttgctgagtc ccaccaccag atgctagtgg cagctatttg ggaacactt aggcactaca       540 aaaaaatgag tgattccatt ctggctcaca ccatatccct gatgtacccc ttaaagcatg     600
tcactgagtt catcacagaa aattgtttcc cctgtgcctt ccacaacaag gttagagctg     660 tccttgggc caggggaagg gggcaggag tgagaagcac caactggata acctcctctg      720 accccactc caccttacca taagtagatc caaatccttc tagaaaatta ggaaggcata     780
tccccatata tcagcgatat aaatagaact gcttcagcgc tctggtagac ggtgactctc     840
caaggtggac tgggaggcag cctggccttg gctgggcatc gtcctctaaa tagaaagatg     900
aacttgttca gcctttccag aaggaaaact gctgcccagc ctacagtgca acgtccttgt    960
cttccatctg gaggaagcac gggtgacata tcatctagta agggcacctc tctgtttcca    1020
cctccaggtc gagggtgtg acccttactt ctcagcctca agggagggac actcaacycc     1080
ccaaaaagac atgagggcgc tcagctcggc ccaccgcacc ccggaccgga gccgtcaccc    1140
cccgaaattc actcccttca caagcccca agcgcgttct ctggtgcgga ctgctccggg    1200
gccctggctt tgtgcccagc gttgtcagag ccaccgccct gagcctgtcc ccgggagccc    1260
cgcgcctcct cccaccgctc crctctcgcg ccccgcggcc agttgtctgc cccgagacag    1320
ctgcgcgccc tcccgctgcc ggtggccctc tccggtgggg gtggggaccg acagggtcag    1380
ccctccggat ccggggcgct ccgggtagcg gggagaagtg atcgctgggg agctggggga    1440
ggggtcgcct tcctgcccta cccaggactc cgggtgcgac cgctcctcta tctctccagc    1500
ccaccaccac tccaccactt ggacacgtct ccctcctccc tggagtcgct ctagagggtt    1560
tgggggtctg agtaaagaac ccgaagtagg gatacagtgt ggcggcacct tccagaggcc    1620
ccgggcgcag ggtagaccgg ggcggggcgg cccgcggaca ggtgcagccc caggcgcagg    1680
cgcactcgcg cctcccggcg caggcggtga acctcgcccc accccagccc ctccgggggg    1740
cagctgggcc gggtcgggag gggcccacca gcccgggaga cactccatat acggccaggc    1800
ccgctttacc tgggctccgg ccaggccgct ccttctttgg tcagcacagg gaccccgggc    1860 ggggggcccag gccgctaacc cgccggggga ggggctcca gtgcccaaca cccaaatatg   1920
gctcgagaag gggagcgaca ttccagtgag gcggctcggg gggagaaccc gcgggctata    1980
taaaacctga gcgtggggac cagcggccaa gctt                                 2014
```

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
cccaagcttg gccgctggtc cccacgctca                                        30

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 10
caggtaccgc tataggagac aaaagagtgc actgagca                               38

```
<210> SEQ ID NO 11
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 11
agatatcccg gccgctctag accaggcccc tggatccgcc accatg            46

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 12
gaagatctct acctgctcat gatgtcctgg agcagcttgc gggc              44

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 13
gtcattccga gattcggata                                          20

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 14
gtcattccga gattcggata cacaggatcc gccaccatcc                    40

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 15
cactctgggt gttcttcttt gtgatcctca ccctcagcaa                    40

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 16
cagctcccac tgctcccccac ctcccccttt gaccctcagg                   40

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Primer
```

```
<400> SEQUENCE: 17
atgcggcggt attatgcaga tgccatcttc accaacagct                    40

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 18
accggaaggt gctgggccag ctgtccgccc gcaagctcct                    40

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 19
ccaggacatc atgagcaggt agagatctga taagcgttat                    40

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 20
ataacgctta tcagatctct                                          20

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 21
acctgctcat gatgtcctgg accagcttgc gggcggacag                    40

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 22
ctggcccagc accttccggt agctgttggt gaagatggca                    40

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 23
tctgcataat accgccgcat cctgagggtc aaaccccccag                   40

<210> SEQ ID NO 24
<211> LENGTH: 40
```

```
<212> TYPE: DNA
<213> ORGANISM: Artificial Sequence
<220> FEATURE:
<223> OTHER INFORMATION: Description of Artificial Sequence: Primer

<400> SEQUENCE: 24
gtggggagca gtgggagctg ttgctgaggg tgaggatcac                           40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 25
gtggggagca gtgggagctg ttgctgaggg tcaggatcac                           40

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 26
gagctcaagc ttgccaccat gccactctgg                                      30

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 27
aagatctaga ctacctgctc atgatgtc                                        28

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 28
gagctcaagc ttgccaccat gccactctgg                                      30

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 29
aagatctaga ctacctgctc atgatgtc                                        28

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 30
```
gtcattccga gattcggata                                              20

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 31
gtcattccga gattcggata cacaggatcc gccaccatcc                        40

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 32
cactctgggt gttcttcttt gtgatcctca ccctcagcaa                        40

<210> SEQ ID NO 33
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 33
cagctccact gctccccacc tcccccttcg accctcagg                         39

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 34
atgcggcggt attatgcaga tcccatcttc accaacagct                        40

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 35
accggaaggt gctggcccag ctgtccgccc gcaaggccct                        40

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 36
ccaggacatc atgagcaggt agagatctga taagcgttat                        40

<210> SEQ ID NO 37
<211> LENGTH: 20
<212> TYPE: DNA
<213> ORGANISM: Artificial Sequence -continued
<220> FEATURE:
<223> OTHER INFORMATION: Description of Artificial Sequence: Primer

<400> SEQUENCE: 37
ataacgctta tcagatctct                                                    20

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 38
acctgctcat gatgtcctgg agggccttgc gggcccacag                              40

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 39
ctgggccagc accttccggt acctgttggt gaagatggca                              40

<210> SEQ ID NO 40
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 40
tctccataat accgccgcat cctgagggtc aaaggggag                               40

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 41
gtggggagca gtgggagctg ttgctgaggg tgaggatcac                              40

<210> SEQ ID NO 42
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 42
gtggggagca gtgggagctc ttgctgaggg tgaggatcac                              40

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 43
ctagaaggca cagctgcttt ccacg                                              25

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 44
atggctgcag gcccccggac tctg         25

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 45
aaagatatca tggctgcagg cccccgg      27

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 46
aaaagatctc tagaaggcac agctgct      27

<210> SEQ ID NO 47
<211> LENGTH: 5185
<212> TYPE: DNA
<213> ORGANISM: Artificial Sequence
<220> FEATURE:
<223> OTHER INFORMATION: Description of Artificial Sequence: pGHRH-4
      construct

<400> SEQUENCE: 47
gctgtgcctt ctagttgcca gccatctgtt gtttgcccct cccccgtgcc ttccttgacc      60
ctggaaggtg ccactcccac tgtccttttc taataaaatg aggaaattgc atcgcattgt     120
ctgagtaggt gtcattctat tctggggggt ggggtggggc aggacagcaa ggggaggat     180
tgggaagaca atagcaggca tgctggggat gcggtgggct ctatgggtac ccaggtgctg     240
aagaattgac ccggttcctc ctgggccaga aagaagcagg cacatcccct tctctgtgac     300
acaccctgtc cacgcccctg gttcttagtt ccagccccac tcataggaca ctcatagctc     360
aggagggctc cgccttcaat cccacccgct aaagtacttg gagcggtctc tccctccctc     420
atcagcccac caaaccaaac ctagcctcca agagtgggaa gaaattaaag caagataggc     480
tattaagtgc agagggagag aaaatgcctc caacatgtga ggaagtaatg agagaaatca     540
tagaatttct tccgcttcct cgctcactga ctcgctgcgc tcggtcgttc ggctgcggcg     600
agcggtatca gctcactcaa aggcggtaat acgttatcc acagaatcag ggataacgc      660
aggaaagaac atgtgagcaa aaggccagca aaaggccagg aaccgtaaaa aggccgcgtt     720
gctggcgttt ttccataggc tccgcccccc tgacgagcat cacaaaaatc gacgctcaag     780
tcagaggtgg cgaaacccga caggactata aagataccag gcgtttcccc ctggaagctc     840
cctcgtgcgc tctcctgttc cgaccctgcc gcttaccgga tacctgtccg cctttctccc     900
ttcgggaagc gtggcgcttt ctcatagctc acgctgtagg tatctcagtt cggtgtaggt     960

-continued

```
cgttcgctcc aagctgggct gtgtgcacga accccccgtt cagcccgacc gctgcgcctt    1020
atccggtaac tatcgtcttg agtccaaccc ggtaagacac gacttatcgc cactggcagc    1080
agccactggt aacaggatta gcagagcgag gtatgtaggc ggtgctacag agttcttgaa    1140
gtggtggcct aactacggct acactagaag aacagtattt ggtatctgcg ctctgctgaa    1200
gccagttacc ttcggaaaaa gagttggtag ctccttgatcc ggcaaacaaa ccaccgctgg    1260
tagcggtggt ttttttgttt gcaagcagca gattacgcgc agaaaaaaag gatctcaaga    1320
agatcctttg atcttttcta cggggtctga cgctcagtgg aacgaaaact cacgttaagg    1380
gattttggtc atgagattat caaaaaggat cttcacctag atccttttaa attaaaaatg    1440
aagttttaaa tcaatctaaa gtatatatga gtaaacttgg tctgacagtt accaatgctt    1500
aatcagtgag gcacctatct cagcgatctg tctatttcgt tcatccatag ttgcctgact    1560 cgggggggggg gggcgctgag gtctgcctcg tgaagaaggt gttgctgact cataccaggc    1620
ctgaatcgcc ccatcatcca gccagaaagt gagggagcca cggttgatga gagctttgtt    1680
gtaggtggac cagttggtga ttttgaactt ttgctttgcc acggaacggt ctgcgttgtc    1740
gggaagatgc gtgatctgat ccttcaactc agcaaaagtt cgatttattc aacaaagccg    1800
ccgtcccgtc aagtcagcgt aatgctctgc cagtgttaca accaattaac caattctgat    1860
tagaaaaact catcgagcat caaatgaaac tgcaatttat tcatatcagg attatcaata    1920 ccatatttt gaaaagccg tttctgtaat gaaggagaaa actcaccgag gcagttccat    1980
aggatggcaa gatcctggta tcggtctgcg attccgactc gtccaacatc aatacaacct    2040
attaatttcc cctcgtcaaa aataaggtta tcaagtgaga aatcaccatg agtgacgact    2100
gaatccggtg agaatggcaa aagcttatgc atttctttcc agacttgttc aacaggccag    2160
ccattacgct cgtcatcaaa atcactcgca tcaaccaaac cgttattcat tcgtgattgc    2220
gcctgagcga cgaaatac gcgatcgctg ttaaaaggac aattacaaac aggaatcgaa    2280
tgcaaccggc gcaggaacac tgccagcgca tcaacaatat tttcacctga atcaggatat    2340
tcttctaata cctggaatgc tgttttcccg gggatcgcag tggtgagtaa ccatgcatca    2400
tcaggagtac ggataaaatg cttgatggtc ggaagaggca taaattccgt cagccagttt    2460
agtctgacca tctcatctgt aacatcattg gcaacgctac ctttgccatg tttcagaaac    2520
aactctggcg catcgggctt cccatacaat cgatagattg tcgcacctga ttgcccgaca    2580
ttatcgcgag cccatttata cccatataaa tcagcatcca tgttggaatt taatcgcggc    2640
ctcgagcaag acgtttcccg ttgaatatgg ctcataacac cccttgtatt actgtttatg    2700
taagcagaca gttttattgt tcatgatgat atatttttat cttgtgcaat gtaacatcag    2760
agattttgag acacaacgtg ctttcccccc cccccccatt attgaagcat ttatcagggt    2820
tattgtctca tgagcggata catatttgaa tgtatttaga aaataaaca aataggggtt    2880 ccgcgcacat ttccccgaaa agtgccacct gacgtctaag aaaccattat tatcatgaca    2940
ttaacctata aaaataggcg tatcacgagg ccctttcgtc ctcgcgcgtt tcggtgatga    3000
cggtgaaaac ctctgacaca tgcagctccc ggagacggtc acagcttgtc tgtaagcgga    3060
tgccgggagc agacaagccc gtcagggcgc gtcagcgggt gttggcgggt gtcgggctg    3120 gcttaactat gcggcatcag agcagattgt actgagagtg caccatatgc ggtgtgaaat    3180
accgcacaga tgcgtaagga gaaaataccg catcagattg gctattggcc attgcatacg    3240
ttgtatccat atcataatat gtacatttat attggctcat gtccaacatt accgccatgt    3300
tgacattgat tattgactag ttattaatag taatcaatta cggggtcatt agttcatagc    3360
```

-continued

```
ccatatatgg agttccgcgt tacataactt acggtaaatg gcccgcctgg ctgaccgccc    3420 aacgacccc gcccattgac gtcaataatg acgtatgttc ccatagtaac gccaataggg     3480
actttccatt gacgtcaatg ggtggagtat ttacggtaaa ctgcccactt ggcagtacat    3540
caagtgtatc atatgccaag tacgccccct attgacgtca atgacggtaa atggcccgcc    3600
tggcattatg cccagtacat gaccttatgg actttcctac ttggcagta catctacgta    3660 ttagtcatcg ctattaccat ggtgatgcgg ttttggcagt acatcaatgg gcgtggatag    3720
cggtttgact cacggggatt tccaagtctc cacccattg acgtcaatgg gagtttgttt     3780
tggcaccaaa atcaacggga ctttccaaaa tgtcgtaaca actccgcccc attgacgcaa    3840
atgggcggta ggcgtgtacg gtgggaggtc tatataagca gagctcgttt agtgaaccgt    3900
cagatcgcct ggagacgcca tccacgctgt tttgacctcc atagaagaca ccgggaccga    3960
tccagcctcc gcggccggga acggtgcatt ggaacgcgga ttccccgtgc caagagtgac    4020
gtaagtaccg cctatagact ctataggcac accccctttgg ctcttatgca tgctatactg   4080 ttttttggctt ggggcctata cacccccgct tccttatgct ataggtgatg gtatagctta   4140
gcctataggt gtgggttatt gaccattatt gaccactccc ctattggtga cgatactttc    4200
cattactaat ccataacatg gctctttgcc acaactatct ctattggcta tatgccaata    4260
ctctgtcctt cagagactga cacggactct gtattttta ggatggggt cccatttatt      4320 atttacaaat tcacatatac aacaacgccg tccccgtgc ccgcagtttt tattaaacat     4380
agcgtgggat ctccacgcga atctcgggta cgtgttccgg acatgggctc ttctccggta    4440 gcggcgagc ttccacatcc gagccctggt cccatgcctc cagcggctca tggtcgctcg     4500
gcagctcctt gctcctaaca gtggaggcca gacttaggca cagcacaatg cccaccacca    4560
ccagtgtgcc gcacaaggcc gtggcggtag gtatgtgtc tgaaaatgag cgtggagatt     4620
gggctcgcac ggctgacgca gatggaagac ttaaggcagc ggcagaagaa gatgcaggca    4680
gctgagttgt tgtattctga taagagtcag aggtaactcc cgttgcggtg ctgttaacgg    4740
tggagggcag tgtagtctga gcagtactcg ttgctgccgc gcgcgccacc agacataata    4800
gctgacagac taacagactg ttccttttcca tgggtctttt ctgcagtcac cgtcgtcgac    4860
acgtgtgatc agatatcgcg gccgctctag accaggcgcc tggatccgcc accatgccac    4920
tctgggtgtt cttctttgtg atcctcaccc tcagcaacag ctcccactgc tccccacctc    4980 ccccttttgac cctcaggatg cggcggtatg cagatgccat cttcaccaac agctaccgga    5040
aggtgctggg ccagctgtcc gcccgcaagc tgctccagga catcatgagc aggcagcagg    5100
gagagagaaa ccaagagcaa ggagcaaggg tgcggctttg aagatcttag tagtagtagg    5160
cggccgctct agaggatcca gatct                                          5185
```

<210> SEQ ID NO 48
<211> LENGTH: 3369
<212> TYPE: DNA
<213> ORGANISM: Artificial Sequence
<220> FEATURE:
<223> OTHER INFORMATION: Description of Artificial Sequence: pGHRH1-44SK
       construct

<400> SEQUENCE: 48

```
ggtaccgagc tcttacgcgt gctagcccgg gctcgagatc tgcgatctaa gtaagcttgc     60
caccatgcca ctctgggtgt tcttctttgt gatcctcacc ctcagcaaca gctcccactg    120
ctccccacct cccccctttga ccctcaggat gcggcggtat gcagatgcca tcttcaccaa   180
```

-continued

| | |
|---|---|
| cagctaccgg aaggtgctgg gccagctgtc cgcccgcaag ctgctccagg acatcatgag | 240 |
| caggcagcag ggagagagaa accaagagca aggagcaagg gtgcggcttt gatctagagt | 300 |
| cggggcggcc ggccgcttcg agcagacatg ataagataca ttgatgagtt tggacaaacc | 360 |
| acaactagaa tgcagtgaaa aaatgctttt atttgtgaaa tttgtgatgc tattgcttta | 420 |
| tttgtaacca ttataagctg caataaacaa gttaacaaca acaattgcat tcattttatg | 480 |
| tttcaggttc aggggaggt gtgggaggtt ttttaaagca agtaaaacct ctacaaatgt | 540 |
| ggtaaaatcg ataaggatcc gtcgaccgat gcccttgaga gccttcaacc cagtcagctc | 600 |
| cttccggtgg gcgcggggca tgactatcgt cgccgcactt atgactgtct tctttatcat | 660 |
| gcaactcgta ggacaggtgc cggcagcgct cttccgcttc ctcgctcact gactcgctgc | 720 |
| gctcggtcgt tcggctgcgg cgagcggtat cagctcactc aaaggcggta atacggttat | 780 |
| ccacagaatc aggggataac gcaggaaaga acatgtgagc aaaaggccag caaaaggcca | 840 |
| ggaaccgtaa aaaggccgcg ttgctggcgt ttttccatag gctccgcccc cctgacgagc | 900 |
| atcacaaaaa tcgacgctca agtcagaggt ggcgaaaccc gacaggacta taaagatacc | 960 |
| aggcgtttcc ccctggaagc tccctcgtgc gctctcctgt tccgaccctg ccgcttaccg | 1020 |
| gatacctgtc cgcctttctc ccttcgggaa gcgtggcgct ttctcaatgc tcacgctgta | 1080 |
| ggtatctcag ttcggtgtag gtcgttcgct ccaagctggg ctgtgtgcac gaaccccccg | 1140 |
| ttcagcccga ccgctgcgcc ttatccggta actatcgtct tgagtccaac ccggtaagac | 1200 |
| acgacttatc gccactggca gcagccactg gtaacaggat tagcagagcg aggtatgtag | 1260 |
| gcggtgctac agagttcttg aagtggtggc ctaactacgg ctacactaga aggacagtat | 1320 |
| ttggtatctg cgctctgctg aagccagtta ccttcggaaa aagagttggt agctcttgat | 1380 |
| ccggcaaaca aaccaccgct ggtagcggtg gttttttttgt ttgcaagcag cagattacgc | 1440 |
| gcagaaaaaa aggatctcaa gaagatcctt tgatctttc tacggggtct gacgctcagt | 1500 |
| ggaacgaaaa ctcacgttaa gggattttgg tcatgagatt atcaaaaagg atcttcacct | 1560 |
| agatcctttt aaattaaaaa tgaagtttta atcaatcta agtatatat gagtaaactt | 1620 |
| ggtctgacag ttaccaatgc ttaatcagtg aggcacctat ctcagcgatc tgtctatttc | 1680 |
| gttcatccat agttgcctga ctccccgtcg tgtagataac tacgatacgg gagggcttac | 1740 |
| catctggccc cagtgctgca atgataccgc gagacccacg ctcaccggct ccagatttat | 1800 |
| cagcaataaa ccagccagcc ggaagggccg agcgcagaag tggtcctgca actttatccg | 1860 |
| cctccatcca gtctattaat tgttgccggg aagctagagt aagtagttcg ccagttaata | 1920 |
| gtttgcgcaa cgttgttgcc attgctacag gcatcgtggt gtcacgctcg tcgtttggta | 1980 |
| tggcttcatt cagctccggt tcccaacgat caaggcgagt tacatgatcc cccatgttgt | 2040 |
| gcaaaaaagc ggttagctcc ttcggtcctc cgatcgttgt cagaagtaag ttggccgcag | 2100 |
| tgttatcact catggttatg gcagcactgc ataattctct tactgtcatg ccatccgtaa | 2160 |
| gatgcttttc tgtgactggt gagtactcaa ccaagtcatt ctgagaatag tgtatgcggc | 2220 |
| gaccgagttg ctcttgcccg gcgtcaatac gggataatac cgcgccacat agcagaactt | 2280 |
| taaaagtgct catcattgga aaacgttctt cggggcgaaa actctcaagg atcttaccgc | 2340 |
| tgttgagatc cagttcgatg taacccactc gtgcacccaa ctgatcttca gcatctttta | 2400 |
| ctttcaccag cgtttctggg tgagcaaaaa caggaaggca aaatgccgca aaaaagggaa | 2460 |
| taagggcgac acggaaatgt tgaatactca tactcttcct ttttcaatat tattgaagca | 2520 |

-continued

| | |
|---|---|
| tttatcaggg ttattgtctc atgagcggat acatatttga atgtatttag aaaaataaac | 2580 |
| aaataggggt tccgcgcaca tttccccgaa aagtgccacc tgacgcgccc tgtagcggcg | 2640 |
| cattaagcgc ggcgggtgtg gtggttacgc gcagcgtgac cgctacactt gccagcgccc | 2700 |
| tagcgcccgc tcctttcgct ttcttccctt cctttctcgc cacgttcgcc ggctttcccc | 2760 |
| gtcaagctct aaatcggggg ctcccttag ggttccgatt tagtgcttta cggcacctcg | 2820 |
| accccaaaaa acttgattag ggtgatggtt cacgtagtgg gccatcgccc tgatagacgg | 2880 |
| tttttcgccc tttgacgttg gagtccacgt tctttaatag tggactcttg ttccaaactg | 2940 |
| gaacaacact caaccctatc tcggtctatt cttttgattt ataagggatt ttgccgattt | 3000 |
| cggcctattg gttaaaaaat gagctgattt aacaaaaatt taacgcgaat tttaacaaaa | 3060 |
| tattaacgtt tacaatttcc cattcgccat tcaggctgcg caactgttgg gaagggcgat | 3120 |
| cggtgcgggc ctcttcgcta ttacgccagc ccaagctacc atgataagta agtaatatta | 3180 |
| aggtacggga ggtacttgga gcggccgcaa taaaatatct ttattttcat tacatctgtg | 3240 |
| tgttggtttt ttgtgtgaat cgatagtact aacatacgct ctccatcaaa acaaaacgaa | 3300 |
| acaaaacaaa ctagcaaaat aggctgtccc cagtgcaagt gcaggtgcca gaacatttct | 3360 |
| ctatcgata | 3369 |

<210> SEQ ID NO 49
<211> LENGTH: 3976
<212> TYPE: DNA
<213> ORGANISM: Artificial Sequence
<220> FEATURE:
<223> OTHER INFORMATION: Description of Artificial Sequence: pGHRH1-44WTSK685 construct

<400> SEQUENCE: 49

| | |
|---|---|
| ggtaccatcg ctggggagct gggggagggg tcgccttcct gccctaccca ggactccggg | 60 |
| tgcgaccgct cctctatctc tccagcccac caccactcca ccacttggac acgtctccct | 120 |
| cctccctgga gtcgctctag agggtttggg ggtctgagta aagaacccga agtagggata | 180 |
| cagtgtggcg gcaccttcca gaggccccgg gcgcagggta gaccggggcg gggcggcccg | 240 |
| cggacaggtg cagccccagg cgcaggcgca ctcgcgcctc ccggcgcagg cggtgaacct | 300 |
| cgccccaccc cagcccctcc gggggcagc tgggccgggt cggagggggc ccaccagccc | 360 |
| gggagacact ccatatacgg ccaggcccgc tttacctggg ctccggccag gccgctcctt | 420 |
| cttttggtcag cacaggggac ccgggcgggg gcccaggccg ctaacccgcc ggggagggg | 480 |
| gctccagtgc ccaacaccca aatatggctc gagaagggga gcgacattcc agtgaggcgg | 540 |
| ctcgggggga gaacccgcgg gctatataaa acctgagcgt ggggaccagc ggccaccgca | 600 |
| gcggacagcg ccgagagaag cctcgcttcc ctcccgcggc gaccagggcc ccagccggag | 660 |
| agcagcaggt gtagccacca agcttgccac catgccactc tgggtgttct tctttgtgat | 720 |
| cctcacccct cagcaacagc tcccactgct ccccacctcc cctttgaccc tcaggatgcg | 780 |
| gcggtatgca gatgccatct tcaccaacag ctaccggaag gtgctgggcc agctgtccgc | 840 |
| ccgcaagctg ctccaggaca tcatgagcag gcagcaggga gagagaaacc aagagcaagg | 900 |
| agcaagggtg cggctttgat ctagagtcgg ggcggccggc cgcttcgagc agacatgata | 960 |
| agatacattg atgagtttgg acaaaccaca actagaatgc agtgaaaaaa atgctttatt | 1020 |
| tgtgaaattt gtgatgctat tgctttattt gtaaccatta taagctgcaa taaacaagtt | 1080 |
| aacaacaaca attgcattca ttttatgttt caggttcagg gggaggtgtg ggaggttttt | 1140 |

```
taaagcaagt aaaacctcta caaatgtggt aaaatcgata aggatccgtc gaccgatgcc    1200
cttgagagcc ttcaacccag tcagctcctt ccggtgggcg cggggcatga ctatcgtcgc    1260
cgcacttatg actgtcttct ttatcatgca actcgtagga caggtgccgg cagcgctctt    1320
ccgcttcctc gctcactgac tcgctgcgct cggtcgttcg gctgcggcga gcggtatcag    1380
ctcactcaaa ggcggtaata cggttatcca cagaatcagg ggataacgca ggaaagaaca    1440
tgtgagcaaa aggccagcaa aaggccagga accgtaaaaa ggccgcgttg ctggcgtttt    1500
tccataggct ccgcccccct gacgagcatc acaaaaatcg acgctcaagt cagaggtggc    1560
gaaacccgac aggactataa agataccagg cgtttccccc tggaagctcc ctcgtgcgct    1620
ctcctgttcc gaccctgccg cttaccggat acctgtccgc ctttctccct tcgggaagcg    1680
tggcgctttc tcaatgctca cgctgtaggt atctcagttc ggtgtaggtc gttcgctcca    1740
agctgggctg tgtgcacgaa ccccccgttc agcccgaccg ctgcgcctta tccggtaact    1800
atcgtcttga gtccaacccg gtaagacacg acttatcgcc actggcagca gccactggta    1860
acaggattag cagagcgagg tatgtaggcg gtgctacaga gttcttgaag tggtggccta    1920
actacggcta cactagaagg acagtatttg gtatctgcgc tctgctgaag ccagttacct    1980
tcggaaaaag agttggtagc tcttgatccg gcaaacaaac caccgctggt agcggtggtt    2040
tttttgtttg caagcagcag attacgcgca gaaaaaagg atctcaagaa gatcctttga    2100
tcttttctac ggggtctgac gctcagtgga acgaaaactc acgttaaggg attttggtca    2160
tgagattatc aaaaaggatc ttcacctaga tccttttaaa ttaaaaatga agttttaaat    2220
caatctaaag tatatatgag taaacttggt ctgacagtta ccaatgctta atcagtgagg    2280
cacctatctc agcgatctgt ctatttcgtt catccatagt tgcctgactc cccgtcgtgt    2340
agataactac gatacgggag ggcttaccat ctggccccag tgctgcaatg ataccgcgag    2400
acccacgctc accggctcca gatttatcag caataaacca gccagccgga agggccgagc    2460
gcagaagtgg tcctgcaact ttatccgcct ccatccagtc tattaattgt tgccgggaag    2520
ctagagtaag tagttcgcca gttaatagtt tgcgcaacgt tgttgccatt gctacaggca    2580
tcgtggtgtc acgctcgtcg tttggtatgg cttcattcag ctccggttcc caacgatcaa    2640
ggcgagttac atgatccccc atgttgtgca aaaaagcggt tagctccttc ggtcctccga    2700
tcgttgtcag aagtaagttg gccgcagtgt tatcactcat ggttatggca gcactgcata    2760
attctcttac tgtcatgcca tccgtaagat gcttttctgt gactggtgag tactcaacca    2820
agtcattctg agaatagtgt atgcggcgac cgagttgctc ttgcccggcg tcaatacggg    2880
ataataccgc gccacatagc agaactttaa aagtgctcat cattggaaaa cgttcttcgg    2940
ggcgaaaact ctcaaggatc ttaccgctgt tgagatccag ttcgatgtaa cccactcgtg    3000
cacccaactg atcttcagca tcttttactt tcaccagcgt ttctgggtga gcaaaaacag    3060
gaaggcaaaa tgccgcaaaa aagggaataa gggcgacacg gaaatgttga atactcatac    3120
tcttcctttt tcaatattat tgaagcattt atcagggtta ttgtctcatg agcggataca    3180
tatttgaatg tatttagaaa aataaacaaa taggggttcc gcgcacattt ccccgaaaag    3240
tgccacctga cgcgccctgt agcggcgcat taagcgcggc gggtgtggtg gttacgcgca    3300
gcgtgaccgc tacacttgcc agcgccctag cgcccgctcc tttcgctttc ttcccttcct    3360
ttctcgccac gttcgccggc tttccccgtc aagctctaaa tcggggggctc cctttagggt    3420 tccgatttag tgctttacgg cacctcgacc ccaaaaaact tgattagggt gatggttcac    3480
gtagtgggcc atcgccctga tagacggttt ttcgcccttt gacgttggag tccacgttct    3540
```

-continued

| | |
|---|---|
| ttaatagtgg actcttgttc caaactggaa caacactcaa ccctatctcg gtctattctt | 3600 |
| ttgatttata agggattttg ccgatttcgg cctattggtt aaaaaatgag ctgatttaac | 3660 |
| aaaaatttaa cgcgaatttt aacaaaatat taacgtttac aatttcccat tcgccattca | 3720 |
| ggctgcgcaa ctgttgggaa gggcgatcgg tgcgggcctc ttcgctatta cgccagccca | 3780 |
| agctaccatg ataagtaagt aatattaagg tacgggaggt acttggagcg ccgcaataa | 3840 |
| aatatcttta tttcattac atctgtgtgt tggtttttg tgtgaatcga tagtactaac | 3900 |
| atacgctctc catcaaaaca aaacgaaaca aacaaacta gcaaaatagg ctgtccccag | 3960 |
| tgcaagtgca ggtgcc | 3976 |

<210> SEQ ID NO 50
<211> LENGTH: 5325
<212> TYPE: DNA
<213> ORGANISM: Artificial Sequence
<220> FEATURE:
<223> OTHER INFORMATION: Description of Artificial Sequence:
      pGHRH1-44WTSK2014 construct

<400> SEQUENCE: 50

| | |
|---|---|
| ggtaccgcta taggagagaa aagagctgca ctgagcaccc tccttcccct ttaaatgtca | 60 |
| acagattagg agtcagtgaa tgacagcaca cctcttgcta ccttagagac caaaatttaa | 120 |
| gctactcccc ttaagctata gctagagtgc acctgccagt gtctttagtc cccactgatg | 180 |
| gaacaggacc caaggtattg aagatggaac atagttattc attcatcctc taatttaaaa | 240 |
| agctggatat gctgtacagc agaaattgac ggaacaatgt aaatcaacta aacagaaga | 300 |
| aataaaaacc tggggggaaa gaagctgact atgaaacccc aggagctttc tacatgggcc | 360 |
| tggactcacc aaactcttta ttttgtaatg gacttctgac attttagga agggctgtcc | 420 |
| tgatgtgggc tatagaagag ggtttcacat gcttcttcaa gaggacccac actgtcccag | 480 |
| ttgctgagtc ccaccaccag atgctagtgg cagctatttg gggaacactt aggcactaca | 540 |
| aaaaaatgag tgattccatt ctggctcaca ccatatccct gatgtacccc ttaaagcatg | 600 |
| tcactgagtt catcacagaa aattgtttcc cctgtgcctt ccacaacaag gttagagctg | 660 |
| tccttgggc caggggaagg gggcagggag tgagaagcac caactggata acctcctctg | 720 |
| accccactc caccttacca taagtagatc caaatccttc tagaaaatta ggaaggcata | 780 |
| tccccatata tcagcgatat aaatagaact gcttcagcgc tctggtagac ggtgactctc | 840 |
| caaggtggac tgggaggcag cctggccttg gctgggcatc gtcctctaaa tagaaagatg | 900 |
| aacttgttca gccttccag aaggaaaact gctgcccagc ctacagtgca acgtccttgt | 960 |
| cttccatctg gaggaagcac gggtgacata tcatctagta agggcacctc tctgtttcca | 1020 |
| cctccaggtc gagggtgtg acccttactt ctcagcctca agggagggac actcaacccc | 1080 |
| ccaaaaagac atgagggcgc tcagctcggc ccaccgcacc ccggaccgga gccgtcaccc | 1140 |
| cccgaaattc actcccttca caagccccca agcgcgttct ctggtgcgga ctgctccggg | 1200 |
| gccctggctt tgtgcccagc gttgtcagag ccaccgccct gagcctgtcc ccgggagccc | 1260 |
| cgcgcctcct cccaccgctc cgctctcgcg cccgcggcc agttgtctgc cccgagacag | 1320 |
| ctgcgcgccc tcccgctgcc ggtggccctc tccgtgggg gtgggaccg acagggtcag | 1380 |
| ccctccggat ccggggcgct ccgggtagcg gggagaagtg atcgctgggg agctggggga | 1440 |
| gggtcgcct tcctgcccta cccaggactc cgggtgcgac cgctcctcta tctctccagc | 1500 |
| ccaccaccac tccaccactt ggacacgtct ccctcctccc tggagtcgct ctagagggtt | 1560 |

-continued

```
tgggggtctg agtaaagaac ccgaagtagg gatacagtgt ggcggcacct tccagaggcc    1620
ccgggcgcag ggtagaccgg ggcggggcgg cccgcggaca ggtgcagccc caggcgcagg    1680
cgcactcgcg cctcccggcg caggcggtga acctcgcccc accccagccc ctccgggggg    1740
cagctgggcc gggtcgggag gggcccacca gcccgggaga cactccatat acggccaggc    1800
ccgctttacc tgggctccgg ccaggccgct ccttctttgg tcagcacagg gacccgggc    1860 ggggggcccag gccgctaacc cgccggggga gggggctcca gtgcccaaca cccaaatatg    1920
gctcgagaag gggagcgaca ttccagtgag gcggctcggg gggagaaccc gcgggctata    1980
taaaacctga gcgtggggac cagcggccaa gcttgccacc atgccactct gggtgttctt    2040
ctttgtgatc ctcacccctca gcaacagctc ccactgctcc ccacctcccc ctttgaccct    2100
caggatgcgg cggtatgcag atgccatctt caccaacagc taccggaagg tgctgggcca    2160
gctgtccgcc cgcaagctgc tccaggacat catgagcagg cagcagggag agagaaacca    2220
agagcaagga gcaagggtgc ggctttgatc tagagtcggg gcggccggcc gcttcgagca    2280
gacatgataa gatacattga tgagtttgga caaaccacaa ctagaatgca gtgaaaaaaa    2340
tgctttattt gtgaaatttg tgatgctatt gcttatttg taaccattat aagctgcaat    2400
aaacaagtta acaacaacaa ttgcattcat tttatgtttc aggttcaggg ggaggtgtgg    2460
gaggtttttt aaagcaagta aaacctctac aaatgtggta aaatcgataa ggatccgtcg    2520
accgatgccc ttgagagcct tcaacccagt cagctccttc cggtgggcgc ggggcatgac    2580
tatcgtcgcc gcacttatga ctgtcttctt tatcatgcaa ctcgtaggac aggtgccggc    2640
agcgctcttc cgcttcctcg ctcactgact cgctgcgctc ggtcgttcgg ctgcggcgag    2700
cggtatcagc tcactcaaag gcggtaatac ggttatccac agaatcaggg gataacgcag    2760
gaaagaacat gtgagcaaaa ggccagcaaa aggccaggaa ccgtaaaaag gccgcgttgc    2820
tggcgttttt ccataggctc cgcccccctg acgagcatca caaaaatcga cgctcaagtc    2880
agaggtggcg aaacccgaca ggactataaa gataccaggc gtttccccct ggaagctccc    2940
tcgtgcgctc tcctgttccg accctgccgc ttaccggata cctgtccgcc tttctccctt    3000
cgggaagcgt ggcgctttct caatgctcac gctgtaggta tctcagttcg gtgtaggtcg    3060
ttcgctccaa gctgggctgt gtgcacgaac ccccgttca gcccgaccgc tgcgccttat    3120
ccggtaacta tcgtcttgag tccaacccgg taagacacga cttatcgcca ctggcagcag    3180
ccactggtaa caggattagc agagcgaggt atgtaggcgg tgctacagag ttcttgaagt    3240
ggtggcctaa ctacggctac actagaagga cagtatttgg tatctgcgct ctgctgaagc    3300
cagttacctt cggaaaaaga gttggtagct cttgatccgg caaacaaacc accgctggta    3360
gcggtggttt ttttgtttgc aagcagcaga ttacgcgcag aaaaaaagga tctcaagaag    3420
atcctttgat cttttctacg gggtctgacg ctcagtggaa cgaaaactca cgttaaggga    3480
ttttggtcat gagattatca aaaaggatct tcacctagat cctttaaat taaaaatgaa    3540 gttttaaatc aatctaaagt atatatgagt aaacttggtc tgacagttac caatgcttaa    3600
tcagtgaggc acctatctca gcgatctgtc tatttcgttc atccatagtt gcctgactcc    3660
ccgtcgtgta gataactacg atacgggagg gcttaccatc tggccccagt gctgcaatga    3720
taccgcgaga cccacgctca ccggctccag atttatcagc aataaaccag ccagccgaa    3780 gggccgagcg cagaagtggt cctgcaactt tatccgcctc catccagtct attaattgtt    3840
gccgggaagc tagagtaagt agttcgccag ttaatagttt cgcaacgtt gttgccattg    3900
```

```
ctacaggcat cgtggtgtca cgctcgtcgt ttggtatggc ttcattcagc tccggttccc    3960
aacgatcaag gcgagttaca tgatccccca tgttgtgcaa aaaagcggtt agctccttcg    4020
gtcctccgat cgttgtcaga agtaagttgg ccgcagtgtt atcactcatg gttatggcag    4080
cactgcataa ttctcttact gtcatgccat ccgtaagatg cttttctgtg actggtgagt    4140
actcaaccaa gtcattctga gaatagtgta tgcggcgacc gagttgctct tgcccgcgt    4200
caatacggga taataccgcg ccacatagca gaactttaaa agtgctcatc attggaaaac    4260
gttcttcggg gcgaaaactc tcaaggatct taccgctgtt gagatccagt tcgatgtaac    4320
ccactcgtgc acccaactga tcttcagcat cttttacttt caccagcgtt tctgggtgag    4380
caaaaacagg aaggcaaaat gccgcaaaaa agggaataag ggcgacacgg aaatgttgaa    4440
tactcatact cttcctttt caatattatt gaagcattta tcagggttat tgtctcatga    4500
gcggatacat atttgaatgt atttagaaaa ataaacaaat aggggttccg cgcacatttc    4560
cccgaaaagt gccacctgac gcgccctgta gcggcgcatt aagcgcggcg ggtgtggtgg    4620
ttacgcgcag cgtgaccgct acacttgcca gcgccctagc gcccgctcct ttcgctttct    4680
tcccttcctt tctcgccacg ttcgccggct tccccgtca agctctaaat cgggggctcc    4740
ctttagggtt ccgatttagt gctttacggc acctcgaccc caaaaaactt gattagggtg    4800
atggttcacg tagtgggcca tcgccctgat agacggtttt tcgccctttg acgttggagt    4860
ccacgttctt taatagtgga ctcttgttcc aaactggaac aacactcaac cctatctcgg    4920
tctattcttt tgatttataa gggattttgc cgatttcggc ctattggtta aaaaatgagc    4980
tgatttaaca aaaatttaac gcgaatttta acaaaatatt aacgtttaca atttcccatt    5040
cgccattcag gctgcgcaac tgttgggaag ggcgatcggt gcgggcctct tcgctattac    5100
gccagcccaa gctaccatga taagtaagta atattaaggt acgggaggta cttggagcgg    5160
ccgcaataaa atatctttat tttcattaca tctgtgtgtt ggttttttgt gtgaatcgat    5220
agtactaaca tacgctctcc atcaaaacaa aacgaaacaa aacaaactag caaaataggc    5280
tgtccccagt gcaagtgcag gtgccagaac atttctctat cgata               5325
```

<210> SEQ ID NO 51
<211> LENGTH: 5108
<212> TYPE: DNA
<213> ORGANISM: Artificial Sequence
<220> FEATURE:
<223> OTHER INFORMATION: Description of Artificial Sequence:
      pGHRH1-29WTCMV construct

<400> SEQUENCE: 51

```
gctgtgcctt ctagttgcca gccatctgtt gtttgcccct cccccgtgcc ttccttgacc      60
ctggaaggtg ccactcccac tgtcctttcc taataaaatg aggaaattgc atcgcattgt     120
ctgagtaggt gtcattctat tctggggggt ggggtgggc aggacagcaa gggggaggat     180
tgggaagaca atagcaggca tgctggggat gcggtgggct ctatgggtac ccaggtgctg     240
aagaattgac ccggttcctc ctgggccaga aagaagcagg cacatcccct tctctgtgac     300
acaccctgtc cacgcccctg gttcttagtt ccagccccac tcataggaca ctcatagctc     360
aggagggctc cgccttcaat cccacccgct aaagtacttg gagcggtctc tcccctccctc   420
atcagcccac caaaccaaac ctagcctcca agagtgggaa gaaattaaag caagataggc     480
tattaagtgc agagggagag aaaatgcctc caacatgtga ggaagtaatg agagaaatca     540
tagaatttct tccgcttcct cgctcactga ctcgctgcgc tcggtcgttc ggctgcggcg     600
```

-continued

```
agcggtatca gctcactcaa aggcggtaat acgttatccc acagaatcag gggataacgc    660
aggaaagaac atgtgagcaa aaggccagca aaaggccagg aaccgtaaaa aggccgcgtt    720
gctggcgttt ttccataggc tccgcccccc tgacgagcat cacaaaaatc gacgctcaag    780
tcagaggtgg cgaaacccga caggactata aagataccag gcgtttcccc ctggaagctc    840
cctcgtgcgc tctcctgttc cgaccctgcc gcttaccgga tacctgtccg cctttctccc    900
ttcgggaagc gtggcgcttt ctcatagctc acgctgtagg tatctcagtt cggtgtaggt    960
cgttcgctcc aagctgggct gtgtgcacga accccccgtt cagcccgacc gctgcgcctt   1020
atccggtaac tatcgtcttg agtccaaccc ggtaagacac gacttatcgc cactggcagc   1080
agccactggt aacaggatta gcagagcgag gtatgtaggc ggtgctacag agttcttgaa   1140
gtggtggcct aactacggct acactagaag aacagtattt ggtatctgcg ctctgctgaa   1200
gccagttacc ttcggaaaaa gagttggtag ctcttgatcc ggcaaacaaa ccaccgctgg   1260
tagcggtggt ttttttgttt gcaagcagca gattacgcgc agaaaaaaag gatctcaaga   1320
agatcctttg atcttttcta cggggtctga cgctcagtgg aacgaaaact cacgttaagg   1380
gattttggtc atgagattat caaaaaggat cttcacctag atccttttaa attaaaaatg   1440
aagttttaaa tcaatctaaa gtatatatga gtaaacttgg tctgacagtt accaatgctt   1500
aatcagtgag gcacctatct cagcgatctg tctatttcgt tcatccatag ttgcctgact   1560
cggggggggg gggcgctgag gtctgcctcg tgaagaaggt gttgctgact cataccaggc   1620
ctgaatcgcc ccatcatcca gccagaaagt gagggagcca cggttgatga gctttgtt    1680
gtaggtggac cagttggtga ttttgaactt ttgctttgcc acggaacggt ctgcgttgtc   1740
gggaagatgc gtgatctgat ccttcaactc agcaaaagtt cgatttattc aacaaagccg   1800
ccgtcccgtc aagtcagcgt aatgctctgc cagtgttaca accaattaac caattctgat   1860
tagaaaaact catcgagcat caaatgaaac tgcaatttat tcatatcagg attatcaata   1920
ccatattttt gaaaaagccg tttctgtaat gaaggagaaa actcaccgag gcagttccat   1980
aggatggcaa gatcctggta tcggtctgcg attccgactc gtccaacatc aatacaacct   2040
attaatttcc cctcgtcaaa aataaggtta tcaagtgaga aatcaccatg agtgacgact   2100
gaatccggtg agaatggcaa aagcttatgc atttctttcc agacttgttc aacaggccag   2160
ccattacgct cgtcatcaaa atcactcgca tcaaccaaac cgttattcat tcgtgattgc   2220
gcctgagcga cacgaaatac gcgatcgctg ttaaaaggac aattacaaac aggaatcgaa   2280
tgcaaccggc gcaggaacac tgccagcgca tcaacaatat tttcacctga atcaggatat   2340
tcttctaata cctggaatgc tgttttcccg gggatcgcag tggtgagtaa ccatgcatca   2400
tcaggagtac ggataaaatg cttgatggtc ggaagaggca taaattccgt cagccagttt   2460
agtctgacca tctcatctgt aacatcattg gcaacgctac ctttgccatg tttcagaaac   2520
aactctggcg catcgggctt cccatacaat cgatagattg tcgcacctga ttgcccgaca   2580
ttatcgcgag cccatttata cccatataaa tcagcatcca tgttggaatt taatcgcggc   2640
ctcgagcaag acgtttcccg ttgaatatgg ctcataacac cccttgtatt actgtttatg   2700
taagcagaca gttttattgt tcatgatgat atatttttat cttgtgcaat gtaacatcag   2760
agattttgag acacaacgtg ctttcccccc ccccccatt attgaagcat ttatcagggt   2820
tattgtctca tgagcggata catatttgaa tgtatttaga aaataaaca aatagggtt    2880
ccgcgcacat ttccccgaaa agtgccacct gacgtctaag aaaccattat tatcatgaca   2940
ttaacctata aaaataggcg tatcacgagg ccctttcgtc ctcgcgcgtt tcggtgatga   3000
```

```
cggtgaaaac ctctgacaca tgcagctccc ggagacggtc acagcttgtc tgtaagcgga      3060
tgccgggagc agacaagccc gtcagggcgc gtcagcgggt gttggcgggt gtcgggctg       3120 gcttaactat gcggcatcag agcagattgt actgagagtg caccatatgc ggtgtgaaat      3180
accgcacaga tgcgtaagga gaaaataccg catcagattg gctattggcc attgcatacg      3240
ttgtatccat atcataatat gtacatttat attggctcat gtccaacatt accgccatgt      3300
tgacattgat tattgactag ttattaatag taatcaatta cggggtcatt agttcatagc      3360
ccatatatgg agttccgcgt tacataactt acggtaaatg gcccgcctgg ctgaccgccc      3420 aacgacccc gcccattgac gtcaataatg acgtatgttc ccatagtaac gccaataggg       3480
actttccatt gacgtcaatg ggtggagtat ttacggtaaa ctgcccactt ggcagtacat      3540
caagtgtatc atatgccaag tacgccccct attgacgtca atgacggtaa atggcccgcc      3600
tggcattatg cccagtacat gaccttatgg gactttccta cttggcagta catctacgta      3660
ttagtcatcg ctattaccat ggtgatgcgg ttttggcagt acatcaatgg gcgtggatag      3720
cggtttgact cacggggatt tccaagtctc cacccccattg acgtcaatgg gagtttgttt     3780
tggcaccaaa atcaacggga ctttccaaaa tgtcgtaaca actccgcccc attgacgcaa      3840
atgggcggta ggcgtgtacg gtgggaggtc tatataagca gagctcgttt agtgaaccgt      3900
cagatcgcct ggagacgcca tccacgctgt tttgacctcc atagaagaca ccgggaccga      3960
tccagcctcc gcggccggga acggtgcatt ggaacgcgga ttcccgtgc caagagtgac        4020 gtaagtaccg cctatagact ctataggcac accccttggg ctcttatgca tgctatactg      4080 ttttggcct ggggcctata cacccccgct tccttatgct ataggtgatg gtatagctta       4140
gcctataggt gtgggttatt gaccattatt gaccactccc ctattggtga cgatactttc      4200
cattactaat ccataacatg gctctttgcc acaactatct ctattggcta tatgccaata     4260
ctctgtcctt cagagactga cacggactct gtattttttac aggatggggt cccatttatt    4320
atttacaaat tcacatatac aacaacgccg tcccccgtgc ccgcagtttt tattaaacat      4380
agcgtgggat ctcacgcga atctcgggta cgtgttccgg acatgggctc ttctccggta       4440
gcggcggagc ttccacatcc gagccctggt cccatgcctc cagcggctca tggtcgctcg      4500
gcagctcctt gctcctaaca gtggaggcca gacttaggca cagcacaatg cccaccacca     4560
ccagtgtgcc gcacaaggcc gtggcggtag ggtatgtgtc tgaaaatgag cgtggagatt     4620
gggctcgcac ggctgacgca gatggaagac ttaaggcagc ggcagaagaa gatgcaggca    4680
gctgagttgt tgtattctga taagagtcag aggtaactcc cgttgcggtg ctgttaacgg      4740
tggagggcag tgtagtctga gcagtactcg ttgctgccgc gcgcgccacc agacataata     4800
gctgacagac taacagactg ttcctttcca tgggtctttt ctgcagtcac cgtcgtcgac      4860
acgtgtgatc agatatcgcg gccgctctag accaggcgcc tggatccgcc accatgccac      4920
tctgggtgtt cttctttgtg atcctcaccc tcagcaacag ctcccactgc tccccacctc     4980
cccctttgac cctcaggatg cggcggtatg cagatgccat cttcaccaac agctaccgga      5040
aggtgctggg ccagctgtcc gcccgcaagc tgctccagga catcatgagc aggtagagat      5100
ccagatct                                                               5108
```

<210> SEQ ID NO 52
<211> LENGTH: 5108
<212> TYPE: DNA
<213> ORGANISM: Artificial Sequence
<220> FEATURE:

<223> OTHER INFORMATION: Description of Artificial Sequence:
      pGHRH1-29YWTCMV construct

<400> SEQUENCE: 52

| | | | | | |
|---|---|---|---|---|---|
| gctgtgcctt | ctagttgcca | gccatctgtt | gtttgcccct | ccccgtgcc | ttccttgacc | 60 |
| ctggaaggtg | ccactcccac | tgtccttcc | taataaaatg | aggaaattgc | atcgcattgt | 120 |
| ctgagtaggt | gtcattctat | tctgggggt | ggggtggggc | aggacagcaa | ggggaggat | 180 |
| tgggaagaca | atagcaggca | tgctggggat | gcggtgggct | ctatgggtac | ccaggtgctg | 240 |
| aagaattgac | ccggttcctc | ctgggccaga | aagaagcagg | cacatcccct | tctctgtgac | 300 |
| acaccctgtc | cacgcccctg | gttcttagtt | ccagccccac | tcataggaca | ctcatagctc | 360 |
| aggagggctc | cgccttcaat | cccacccgct | aaagtacttg | gagcggtctc | tccctccctc | 420 |
| atcagcccac | caaaccaaac | ctagcctcca | agagtgggaa | gaaattaaag | caagataggc | 480 |
| tattaagtgc | agagggagag | aaaatgcctc | caacatgtga | ggaagtaatg | agagaaatca | 540 |
| tagaatttct | tccgcttcct | cgctcactga | ctcgctgcgc | tcggtcgttc | ggctgcggcg | 600 |
| agcggtatca | gctcactcaa | aggcggtaat | acgttatcc | acagaatcag | gggataacgc | 660 |
| aggaaagaac | atgtgagcaa | aaggccagca | aaaggccagg | aaccgtaaaa | aggccgcgtt | 720 |
| gctggcgttt | ttccataggc | tccgccccc | tgacgagcat | cacaaaaatc | gacgctcaag | 780 |
| tcagaggtgg | cgaaacccga | caggactata | aagataccag | gcgtttcccc | ctggaagctc | 840 |
| cctcgtgcgc | tctcctgttc | cgaccctgcc | gcttaccgga | tacctgtccg | cctttctccc | 900 |
| ttcgggaagc | gtggcgcttt | ctcatagctc | acgctgtagg | tatctcagtt | cggtgtaggt | 960 |
| cgttcgctcc | aagctgggct | gtgtgcacga | accccccgtt | cagcccgacc | gctgcgcctt | 1020 |
| atccggtaac | tatcgtcttg | agtccaaccc | ggtaagacac | gacttatcgc | cactggcagc | 1080 |
| agccactggt | aacaggatta | gcagagcgag | gtatgtaggc | ggtgctacag | agttcttgaa | 1140 |
| gtggtggcct | aactacggct | acactagaag | aacagtattt | ggtatctgcg | ctctgctgaa | 1200 |
| gccagttacc | ttcggaaaaa | gagttggtag | ctcttgatcc | ggcaaacaaa | ccaccgctgg | 1260 |
| tagcggtggt | ttttttgttt | gcaagcagca | gattacgcgc | agaaaaaaag | gatctcaaga | 1320 |
| agatcctttg | atcttttcta | cggggtctga | cgctcagtgg | aacgaaaact | cacgttaagg | 1380 |
| gattttggtc | atgagattat | caaaaaggat | cttcacctag | atccttttaa | attaaaaatg | 1440 |
| aagttttaaa | tcaatctaaa | gtatatatga | gtaaacttgg | tctgacagtt | accaatgctt | 1500 |
| aatcagtgag | gcacctatct | cagcgatctg | tctatttcgt | tcatccatag | ttgcctgact | 1560 |
| cggggggggg | gggcgctgag | gtctgcctcg | tgaagaaggt | gttgctgact | cataccaggc | 1620 |
| ctgaatcgcc | ccatcatcca | gccagaaagt | gagggagcca | cggttgatga | gagctttgtt | 1680 |
| gtaggtggac | cagttggtga | ttttgaactt | ttgctttgcc | acggaacggt | ctgcgttgtc | 1740 |
| gggaagatgc | gtgatctgat | ccttcaactc | agcaaaagtt | cgatttattc | aacaaagccg | 1800 |
| ccgtcccgtc | aagtcagcgt | aatgctctgc | cagtgttaca | accaattaac | caattctgat | 1860 |
| tagaaaaact | catcgagcat | caaatgaaac | tgcaatttat | tcatatcagg | attatcaata | 1920 |
| ccatattttt | gaaaaagccg | tttctgtaat | gaaggagaaa | actcaccgag | gcagttccat | 1980 |
| aggatggcaa | gatcctggta | tcggtctgcg | attccgactc | gtccaacatc | aatacaacct | 2040 |
| attaatttcc | cctcgtcaaa | aataaggtta | tcaagtgaga | aatcaccatg | agtgacgact | 2100 |
| gaatccggtg | agaatggcaa | aagcttatgc | atttctttcc | agacttgttc | aacaggccag | 2160 |
| ccattacgct | cgtcatcaaa | atcactcgca | tcaaccaaac | cgttattcat | tcgtgattgc | 2220 |

-continued

```
gcctgagcga gacgaaatac gcgatcgctg ttaaaaggac aattacaaac aggaatcgaa    2280
tgcaaccggc gcaggaacac tgccagcgca tcaacaatat tttcacctga atcaggatat    2340
tcttctaata cctggaatgc tgttttcccg gggatcgcag tggtgagtaa ccatgcatca    2400
tcaggagtac ggataaaatg cttgatggtc ggaagaggca taaattccgt cagccagttt    2460
agtctgacca tctcatctgt aacatcattg gcaacgctac ctttgccatg tttcagaaac    2520
aactctggcg catcgggctt cccatacaat cgatagattc tcgcacctga ttgcccgaca    2580
ttatcgcgag cccatttata cccatataaa tcagcatcca tgttggaatt taatcgcggc    2640
ctcgagcaag acgtttcccg ttgaatatgg ctcataacac cccttgtatt actgtttatg    2700
taagcagaca gtttttattgt tcatgatgat atattttat cttgtgcaat gtaacatcag    2760
agattttgag acacaacgtg gctttccccc cccccccatt attgaagcat ttatcagggt    2820
tattgtctca tgagcggata catatttgaa tgtatttaga aaataaaca aatagggtt     2880 ccgcgcacat ttccccgaaa agtgccacct gacgtctaag aaaccattat tatcatgaca    2940
ttaacctata aaataggcg tatcacgagg cccttttcgtc ctcgcgcgtt tcggtgatga    3000
cggtgaaaac ctctgacaca tgcagctccc ggagacggtc acagcttgtc tgtaagcgga    3060
tgccgggagc agacaagccc gtcagggcgc gtcagcgggt gttggcgggt gtcggggctg    3120
gcttaactat gcggcatcag agcagattgt actgagagtg caccatatgc ggtgtgaaat    3180
accgcacaga tgcgtaagga gaaaataccg catcagattg gctattggcc attgcatacg    3240
ttgtatccat atcataatat gtacatttat attggctcat gtccaacatt accgccatgt    3300
tgacattgat tattgactag ttattaatag taatcaatta cggggtcatt agttcatagc    3360
ccatatatgg agttccgcgt tacataactt acggtaaatg gcccgcctgg ctgaccgccc    3420
aacgaccccc gcccattgac gtcaataatg acgtatgttc ccatagtaac gccaataggg    3480
actttccatt gacgtcaatg ggtggagtat ttacggtaaa ctgcccactt ggcagtacat    3540
caagtgtatc atatgccaag tacgccccct attgacgtca atgacggtaa atggcccgcc    3600
tggcattatg cccagtacat gaccttatgg gactttccta cttggcagta catctacgta    3660
ttagtcatcg ctattaccat ggtgatgcgg ttttggcagt acatcaatgg gcgtggatag    3720
cggtttgact cacggggatt tccaagtctc cacccccattg acgtcaatgg gagtttgttt    3780
tggcaccaaa atcaacggga ctttccaaaa tgtcgtaaca actccgcccc attgacgcaa    3840
atgggcggta ggcgtgtacg gtgggaggtc tatataagca gagctcgttt agtgaaccgt    3900
cagatcgcct ggagacgcca tccacgctgt tttgacctcc atagaagaca ccgggaccga    3960
tccagcctcc gcggccggga acggtgcatt ggaacgcgga ttccccgtgc caagagtgac    4020
gtaagtaccg cctatagact ctataggcac accccttggg ctcttatgca tgctatactg    4080
tttttggctt ggggcctata caccccgct tccttatgct ataggtgatg gtatagctta    4140
gcctataggt gtgggttatt gaccattatt gaccactccc ctattggtga cgatactttc    4200
cattactaat ccataacatg gctctttgcc acaactatct ctattggcta tgccaata     4260 ctctgtcctt cagagactga cacgactct gtattttac aggatggggt cccatttatt     4320
atttacaaat tcacatatac aacaacgccg tccccgtgc ccgcagtttt tattaaacat    4380
agcgtgggat ctccacgcga atctcgggta cgtgttccgg acatgggctc ttctccggta    4440
gcggcggagc ttccacatcc gagccctggt cccatgcctc cagcggctca tggtcgctcg    4500
gcagctcctt gctcctaaca gtggaggcca gacttaggca cagcacaatg cccaccacca    4560
ccagtgtgcc gcacaaggcc gtggcggtag ggtatgtgtc tgaaaatgag cgtggagatt    4620
```

-continued

```
gggctcgcac ggctgacgca gatggaagac ttaaggcagc ggcagaagaa gatgcaggca    4680
gctgagttgt tgtattctga taagagtcag aggtaactcc cgttgcggtg ctgttaacgg    4740
tggagggcag tgtagtctga gcagtactcg ttgctgccgc gcgcgccacc agacataata    4800
gctgacagac taacagactg ttcctttcca tgggtctttt ctgcagtcac cgtcgtcgac    4860
acgtgtgatc agatatcgcg gccgctctag accaggcgcc tggatccgcc accatgccac    4920
tctgggtgtt cttctttgtg atcctcaccc tcagcaacag ctcccactgc tccccacctc    4980
cccctttgac cctcaggatg cggcggtatg cagatgccat cttcaccaac agctaccgga    5040
aggtgctggg ccagctgtcc gcccgcaagc tcctccagga catcatgagc aggtagagat    5100
ccagatct                                                              5108
```

<210> SEQ ID NO 53
<211> LENGTH: 3954
<212> TYPE: DNA
<213> ORGANISM: Artificial Sequence
<220> FEATURE:
<223> OTHER INFORMATION: Description of Artificial Sequence:
      pGHRH1-29YWTSK685 construct

<400> SEQUENCE: 53

```
ggtaccatcg ctggggagct gggggagggg tcgccttcct gccctaccca ggactccggg     60
tgcgaccgct cctctatctc tccagcccac caccactcca ccacttggac acgtctccct    120
cctccctgga gtcgctctag agggtttggg ggtctgagta agaacccga agtagggata    180
cagtgtggcg gcaccttcca gaggccccgg gcgcagggta gaccggggcg gggcggcccg    240
cggacaggtg cagccccagg cgcaggcgca ctcgcgcctc ccggcgcagg cggtgaacct    300
cgccccaccc cagcccctcc gggggggcagc tgggccgggt cgggagggc ccaccagccc    360
gggagacact ccatatacgg ccaggcccgc tttacctggg ctccggccag gccgctcctt    420
cttttggtcag cacaggggac ccgggcgggg gcccaggccg ctaacccgcc gggggagggg    480
gctccagtgc ccaacaccca aatatggctc gagaagggga gcgacattcc agtgaggcgg    540
ctcgggggga gaacccgcgg gctatataaa acctgagcgt ggggaccagc ggccaccgca    600
gcggacagcg ccgagagaag cctcgcttcc ctcccgcggc gaccagggcc ccagccggag    660
agcagcaggt gtagccacca agcttgccac catgccactc tgggtgttct ctttgtgat    720
cctcaccctc agcaacagct cccactgctc cccacctccc cctttgaccc tcaggatgcg    780
gcggtattat gcagatgcca tcttcaccaa cagctaccgg aaggtgctgg gccagctgtc    840
cgcccgcaag ctcctccagg acatcatgag caggtagtct agagtcgggg cggccggccg    900
cttcgagcag acatgataag atacattgat gagtttggac aaaccacaac tagaatgcag    960
tgaaaaaaat gctttatttg tgaaatttgt gatgctattg ctttatttgt aaccattata   1020
agctgcaata aacaagttaa caacaacaat gcattcatt ttatgtttca ggttcagggg   1080
gaggtgtggg aggttttttta aagcaagtaa aacctctaca aatgtggtaa aatcgataag   1140
gatccgtcga ccgatgccct tgagagcctt caacccagtc agctccttcc ggtgggcgcg   1200
ggcatgact atcgtcgccg cacttatgac tgtcttcttt atcatgcaac tcgtaggaca   1260
ggtgccggca gcgctcttcc gcttcctcgc tcactgactc gctgcgctcg tcgttcggc   1320
tgcggcgagc ggtatcagct cactcaaagg cggtaatacg gttatccaca gaatcagggg   1380
ataacgcagg aaagaacatg tgagcaaaag gccagcaaaa ggccaggaac cgtaaaaagg   1440
ccgcgttgct ggcgtttttc cataggctcc gcccccctga cgagcatcac aaaaatcgac   1500
```

-continued

```
gctcaagtca gaggtggcga aacccgacag gactataaag ataccaggcg tttcccoctg   1560 gaagctccct cgtgcgctct cctgttccga ccctgccgct taccggatac ctgtccgcct   1620
ttctcccttc gggaagcgtg gcgctttctc aatgctcacg ctgtaggtat ctcagttcgg   1680
tgtaggtcgt tcgctccaag ctgggctgtg tgcacgaacc ccccgttcag cccgaccgct   1740
gcgccttatc cggtaactat cgtcttgagt ccaacccggt aagacacgac ttatcgccac   1800
tggcagcagc cactggtaac aggattagca gagcgaggta tgtaggcggt gctacagagt   1860
tcttgaagtg gtggcctaac tacggctaca ctagaaggac agtatttggt atctgcgctc   1920
tgctgaagcc agttaccttc ggaaaaagag ttggtagctc ttgatccggc aaacaaacca   1980
ccgctggtag cggtggtttt tttgtttgca agcagcagat tacgcgcaga aaaaaaggat   2040
ctcaagaaga tcctttgatc ttttctacgg ggtctgacgc tcagtggaac gaaaactcac   2100
gttaagggat tttggtcatg agattatcaa aaaggatctt cacctagatc cttttaaatt   2160
aaaaatgaag ttttaaatca atctaaagta tatatgagta aacttggtct gacagttacc   2220
aatgcttaat cagtgaggca cctatctcag cgatctgtct atttcgttca tccatagttg   2280
cctgactccc cgtcgtgtag ataactacga tacgggaggg cttaccatct ggccccagtg   2340
ctgcaatgat accgcgagac ccacgctcac cggctccaga tttatcagca ataaaccagc   2400
cagccggaag ggccgagcgc agaagtggtc ctgcaacttt atccgcctcc atccagtcta   2460
ttaattgttg ccgggaagct agagtaagta gttcgccagt taatagtttg cgcaacgttg   2520
ttgccattgc tacaggcatc gtggtgtcac gctcgtcgtt tggtatggct tcattcagct   2580
ccggttccca acgatcaagg cgagttacat gatcccccat gttgtgcaaa aaagcggtta   2640
gctccttcgg tcctccgatc gttgtcagaa gtaagttggc cgcagtgtta tcactcatgg   2700
ttatggcagc actgcataat tctcttactg tcatgccatc cgtaagatgc ttttctgtga   2760
ctggtgagta ctcaaccaag tcattctgag aatagtgtat gcggcgaccg agttgctctt   2820
gcccggcgtc aatacgggat aataccgcgc cacatagcag aactttaaaa gtgctcatca   2880
ttggaaaacg ttcttcgggg cgaaaactct caaggatctt accgctgttg agatccagtt   2940
cgatgtaacc cactcgtgca cccaactgat cttcagcatc ttttactttc accagcgttt   3000
ctgggtgagc aaaaacagga aggcaaaatg ccgcaaaaaa gggaataagg gcgacacgga   3060
aatgttgaat actcatactc ttcctttttc aatattattg aagcatttat cagggttatt   3120
gtctcatgag cggatacata tttgaatgta tttagaaaaa taaacaaata ggggttccgc   3180
gcacatttcc ccgaaaagtg ccacctgacg cgccctgtag cggcgcatta agcgcggcgg   3240
gtgtggtggt tacgcgcagc gtgaccgcta cacttgccag cgccctagcg cccgctcctt   3300
tcgctttctt cccttccttt ctcgccacgt tcgccggctt tccccgtcaa gctctaaatc   3360
ggggctcccc tttagggttc cgatttagtg ctttacggca cctcgacccc aaaaaacttg   3420
attagggtga tggttcacgt agtgggccat cgccctgata cggttttt cgccctttga   3480 cgttggagtc cacgttcttt aatagtggac tcttgttcca aactggaaca acactcaacc   3540
ctatctcggt ctattctttt gatttataag ggattttgcc gatttcggcc tattggttaa   3600
aaaatgagct gatttaacaa aaatttaacg cgaattttaa caaaatatta acgtttacaa   3660
tttcccattc gccattcagg ctgcgcaact gttgggaagg gcgatcggtg cgggcctctt   3720
cgctattacg ccagcccaag ctaccatgat aagtaagtaa tattaaggta cgggaggtac   3780
ttggagcggc cgcaataaaa tatctttatt ttcattacat ctgtgtgttg gttttttgtg   3840
```

```
tgaatcgata gtactaacat acgctctcca tcaaaacaaa acgaaacaaa acaaactagc    3900
aaaataggct gtccccagtg caagtgcagg tgccagaaca tttctctatc gata          3954

<210> SEQ ID NO 54
<211> LENGTH: 5163
<212> TYPE: DNA
<213> ORGANISM: Artificial Sequence
<220> FEATURE:
<223> OTHER INFORMATION: Description of Artificial Sequence:
      pGHRH1-29YWTSK2014 construct

<400> SEQUENCE: 54
ggtaccgcta taggagagaa aagagctgca ctgagcaccc tccttcccct ttaaatgtca      60
acagattagg agtcagtgaa tgacagcaca cctcttgcta ccttagagac caaaatttaa    120
gctactcccc ttaagctata gctagagtgc acctgccagt gtctttagtc cccactgatg    180
gaacaggacc caaggtattg aagatggaac atagttattc attcatcctc taatttaaaa    240
agctggatat gctgtacagc agaaattgac ggaacaatgt aaatcaacta aacagaaga     300 aataaaaacc tggggggaaa gaagctgact atgaaacccc aggagctttc tacatgggcc    360
tggactcacc aaactcttta ttttgtaatg gacttctgac attttagga agggctgtcc     420 tgatgtgggc tatagaagag ggtttcacat gcttcttcaa gaggacccac actgtcccag    480
ttgctgagtc ccaccaccag atgctagtgg cagctatttg gggaacactt aggcactaca    540
aaaaaatgag tgattccatt ctggctcaca ccatatccct gatgtacccc ttaaagcatg    600
tcactgagtt catcacagaa aattgtttcc cctgtgcctt ccacaacaag gttagagctg    660 tccttgggc caggggaagg gggcagggag tgagaagcac caactggata acctcctctg     720
acccccactc caccttacca taagtagatc caaatccttc tagaaaatta ggaaggcata    780
tccccatata tcagcgatat aaatagaact gcttcagcgc tctggtagac ggtgactctc    840
caaggtggac tgggaggcag cctggccttg gctgggcatc gtcctctaaa tagaaagatg    900
aacttgttca gccttttccag aaggaaaact gctgcccagc ctacagtgca acgtccttgt   960
cttccatctg gaggaagcac gggtgacata tcatctagta agggcacctc tctgtttcca  1020
cctccaggtc gagggtgtg accccttactt ctcagcctca agggagggac actcaacccc  1080
ccaaaaagac atgagggcgc tcagctcggc ccaccgcacc ccggaccgga gccgtcaccc   1140
cccgaaattc actcccttca caagccccca agcgcgttct ctggtgcgga ctgctccggg   1200
gccctggctt tgtgcccagc gttgtcagag ccaccgccct gagcctgtcc ccgggagccc   1260
cgcgcctcct cccaccgctc cgctctcgcg ccccgcggcc agttgtctgc cccgagacag   1320
ctgcgcgccc tcccgctgcc ggtggccctc tccggtgggg gtggggaccg acagggtcag   1380
ccctccggat ccggggcgct ccgggtagcg gggagaagtg atcgctgggg agctggggga   1440
ggggtcgcct tcctgcccta cccaggactc cgggtgcgac cgctcctcta tctctccagc   1500
ccgggcgcag ggtagaccgg ggcggggcgg cccgcggaca ggtgcagccc caggcgcagg   1560
cgcactcgcg cctcccggcg caggcggtga acctcgcccc accccagccc ctccgggggg   1620
cagctgggcc gggtcgggag gggcccacca gcccgggaga cactccatat acggccaggc   1680
ccgctttacc tggctccgg ccaggccgct ccttctttgg tcagcacagg gacccgggc     1740 gggggcccag gccgctaacc cgccggggga ggggctccca gtgcccaaca cccaaatatg   1800
gctcgagaag gggagcgaca ttccagtgag gcggctcggg gggagaaccc gcgggctata   1860
taaaacctga gcgtggggac cagcggccaa gcttgccacc atgccactct gggtgttctt   1920
```

-continued

```
ctttgtgatc ctcaccctca gcaacagctc ccactgctcc ccacctcccc ctttgacccct    1980
caggatgcgg cggtattatg cagatgccat cttcaccaac agctaccgga aggtgctggg    2040
ccagctgtcc gcccgcaagc tcctccagga catcatgagc aggtagtcta gagtcggggc    2100
ggccggccgc ttcgagcaga catgataaga tacattgatg agtttggaca aaccacaact    2160
agaatgcagt gaaaaaaatg ctttatttgt gaaatttgtg atgctattgc tttatttgta    2220
accattataa gctgcaataa acaagttaac aacaacaatt gcattcattt tatgtttcag    2280
gttcagggg aggtgtggga ggttttttaa agcaagtaaa acctctacaa atgtggtaaa    2340
atcgataagg atccgtcgac cgatgccctt gagagccttc aacccagtca gctccttccg    2400
gtgggcgcgg ggcatgacta tcgtcgccgc acttatgact gtcttcttta tcatgcaact    2460
cgtaggacag gtgccggcag cgctcttccg cttcctcgct cactgactcg ctgcgctcgg    2520
tcgttcggct gcggcgagcg gtatcagctc actcaaaggc ggtaatacgg ttatccacag    2580
aatcagggga taacgcagga aagaacatgt gagcaaaagg ccagcaaaag gccaggaacc    2640
gtaaaaaggc cgcgttgctg gcgttttttcc ataggctccg cccccctgac gagcatcaca    2700
aaaatcgacg ctcaagtcag aggtggcgaa acccgacagg actataaaga taccaggcgt    2760
ttccccctgg aagctccctc gtgcgctctc ctgttccgac cctgccgctt accggatacc    2820
tgtccgcctt tctcccttcg ggaagcgtgg cgctttctca atgctcacgc tgtaggtatc    2880
tcagttcggt gtaggtcgtt cgctccaagc tgggctgtgt gcacgaaccc cccgttcagc    2940
ccgaccgctg cgccttatcc ggtaactatc gtcttgagtc caacccggta agacacgact    3000
tatcgccact ggcagcagcc actggtaaca ggattagcag agcgaggtat gtaggcggtg    3060
ctacagagtt cttgaagtgg tggcctaact acggctacac tagaaggaca gtatttggta    3120
tctgcgctct gctgaagcca gttaccttcg gaaaaagagt ggtagctct tgatccggca    3180
aacaaaccac cgctggtagc ggtggttttt ttgtttgcaa gcagcagatt acgcgcagaa    3240
aaaaaggatc tcaagaagat cctttgatct tttctacggg gtctgacgct cagtggaacg    3300
aaaactcacg ttaagggatt ttggtcatga gattatcaaa aaggatcttc acctagatcc    3360
ttttaaatta aaaatgaagt tttaaatcaa tctaaagtat atatgagtaa acttggtctg    3420
acagttacca atgcttaatc agtgaggcac ctatctcagc gatctgtcta tttcgttcat    3480
ccatagttgc ctgactcccc gtcgtgtaga taactacgat acgggagggc ttaccatctg    3540
gccccagtgc tgcaatgata ccgcgagacc cacgctcacc ggctccagat ttatcagcaa    3600
taaaccagcc agccggaagg gccgagcgca gaagtggtcc tgcaactttc tccgcctcca    3660
tccagtctat taattgttgc cgggaagcta gagtaagtag ttcgccagtt aatagtttgc    3720
gcaacgttgt tgccattgct acaggcatcg tggtgtcacg ctcgtcgttt ggtatggctt    3780
cattcagctc cggttcccaa cgatcaaggc gagttacatg atcccccatg ttgtgcaaaa    3840
aagcggttag ctccttcggt cctccgatcg ttgtcagaag taagttggcc gcagtgttat    3900
cactcatggt tatggcagca ctgcataatt ctcttactgt catgccatcc gtaagatgct    3960
tttctgtgac tggtgagtac tcaaccaagt cattctgaga atagtgtatg cggcgaccga    4020
gttgctcttg cccggcgtca atacgggata ataccgcgcc acatagcaga actttaaaag    4080
tgctcatcat tggaaaacgt tcttcgggc gaaaactctc aaggatctta ccgctgttga    4140
gatccagttc gatgtaaccc actcgtgcac ccaactgatc ttcagcatct tttactttca    4200
ccagcgtttc tgggtgagca aaaacaggaa ggcaaaatgc cgcaaaaaag ggaataaggg    4260
cgacacggaa atgttgaata ctcatactct tcctttttca atattattga agcatttatc    4320
```

```
agggttattg tctcatgagc ggatacatat ttgaatgtat ttagaaaaat aaacaaatag    4380
gggttccgcg cacatttccc cgaaaagtgc cacctgacgc gccctgtagc ggcgcattaa    4440
gcgcggcggg tgtggtggtt acgcgcagcg tgaccgctac acttgccagc gccctagcgc    4500
ccgctccttt cgctttcttc ccttcctttc tcgccacgtt cgccggcttt ccccgtcaag    4560
ctctaaatcg gggctccct ttaggggttcc gatttagtgc tttacggcac ctcgacccca    4620
aaaaacttga ttagggtgat ggttcacgta gtgggccatc gccctgatag acggttttc    4680
gcccttgac gttggagtcc acgttcttta atagtggact cttgttccaa actgaacaa    4740
cactcaaccc tatctcggtc tattcttttg atttataagg gattttgccg atttcggcct    4800
attggttaaa aaatgagctg atttaacaaa aatttaacgc gaattttaac aaaatattaa    4860
cgtttacaat ttcccattcg ccattcaggc tgcgcaactg ttgggaaggg cgatcggtgc    4920
gggcctcttc gctattacgc cagcccaagc taccatgata agtaagtaat attaaggtac    4980
gggaggtact tggagcggcc gcaataaaat atctttattt tcattacatc tgtgtgttgg    5040
tttttttgtgt gaatcgatag tactaacata cgctctccat caaaacaaaa cgaaacaaaa    5100
caaactagca aaataggctg tccccagtgc aagtgcaggt gccagaacat ttctctatcg    5160
ata                                                                   5163
```

<210> SEQ ID NO 55
<211> LENGTH: 5111
<212> TYPE: DNA
<213> ORGANISM: Artificial Sequence
<220> FEATURE:
<223> OTHER INFORMATION: Description of Artificial Sequence:
      pGHRH1-29Yala1522CMV construct

<400> SEQUENCE: 55

```
gctgtgcctt ctagttgcca gccatctgtt gtttgcccct cccccgtgcc ttccttgacc     60
ctggaaggtg ccactcccac tgtcctttcc taataaaatg aggaaattgc atcgcattgt    120
ctgagtaggt gtcattctat tctggggggt ggggtggggc aggacagcaa ggggaggat    180
tgggaagaca atagcaggca tgctggggat gcggtgggct ctatgggtac ccaggtgctg    240
aagaattgac ccggttcctc ctgggccaga aagaagcagg cacatcccct tctctgtgac    300
acaccctgtc cacgcccctg gttcttagtt ccagccccac tcataggaca ctcatagctc    360
aggagggctc cgccttcaat cccacccgct aaagtacttg gagcggtctc tccctcccctc    420
atcagcccac caaaccaaac ctagcctcca agagtgggaa gaaattaaag caagataggc    480
tattaagtgc agagggagag aaaatgcctc caacatgtga ggaagtaatg agagaaatca    540
tagaatttct tccgcttcct cgctcactga ctcgctgcgc tcggtcgttc ggctgcggcg    600
agcggtatca gctcactcaa aggcggtaat acggttatcc acagaatcag gggataacgc    660
aggaaagaac atgtgagcaa aaggccagca aaaggccagg aaccgtaaaa aggccgcgtt    720
gctggcgttt ttccataggc tccgcccccc tgacgagcat cacaaaaatc gacgctcaag    780
tcagaggtgg cgaaacccga caggactata aagataccag gcgtttcccc ctggaagctc    840
cctcgtgcgc tctcctgttc cgaccctgcc gcttaccgga tacctgtccg cctttctccc    900
ttcgggaagc gtggcgcttt ctcatagctc acgctgtagg tatctcagtt cggtgtaggt    960
cgttcgctcc aagctgggct gtgtgcacga accccccgtt cagcccgacc gctgcgcctt   1020
atccggtaac tatcgtcttg agtccaaccc ggtaagacac gacttatcgc cactggcagc   1080
agccactggt aacaggatta gcagagcgag gtatgtaggc ggtgctacag agttcttgaa   1140
```

-continued

```
gtggtggcct aactacggct acactagaag aacagtattt ggtatctgcg ctctgctgaa    1200
gccagttacc ttcggaaaaa gagttggtag ctcttgatcc ggcaaacaaa ccaccgctgg    1260
tagcggtggt ttttttgttt gcaagcagca gattacgcgc agaaaaaaag gatctcaaga    1320
agatcctttg atcttttcta cggggtctga cgctcagtgg aacgaaaact cacgttaagg    1380
gattttggtc atgagattat caaaaaggat cttcacctag atccttttaa attaaaaatg    1440
aagttttaaa tcaatctaaa gtatatatga gtaaacttgg tctgacagtt accaatgctt    1500
aatcagtgag gcacctatct cagcgatctg tctatttcgt tcatccatag ttgcctgact    1560
cggggggggg gggcgctgag gtctgcctcg tgaagaaggt gttgctgact cataccaggc    1620
ctgaatcgcc ccatcatcca gccagaaagt gagggagcca cggttgatga gagctttgtt    1680
gtaggtggac cagttggtga ttttgaactt ttgctttgcc acggaacggt ctgcgttgtc    1740
gggaagatgc gtgatctgat ccttcaactc agcaaaagtt cgatttattc aacaaagccg    1800
ccgtcccgtc aagtcagcgt aatgctctgc cagtgttaca accaattaac caattctgat    1860
tagaaaaact catcgagcat caaatgaaac tgcaatttat tcatatcagg attatcaata    1920
ccatattttt gaaaagccg tttctgtaat gaaggagaaa actcaccgag gcagttccat     1980
aggatggcaa gatcctggta tcggtctgcg attccgactc gtccaacatc aatacaacct    2040
attaatttcc cctcgtcaaa aataaggtta tcaagtgaga atcaccatg agtgacgact     2100
gaatccggtg agaatggcaa aagcttatgc atttctttcc agacttgttc aacaggccag    2160
ccattacgct cgtcatcaaa atcactcgca tcaaccaaac cgttattcat tcgtgattgc    2220
gcctgagcga cgaaatac gcgatcgctg ttaaaaggac aattacaaac aggaatcgaa      2280
tgcaaccggc gcaggaacac tgccagcgca tcaacaatat tttcacctga atcaggatat    2340
tcttctaata cctggaatgc tgttttcccg gggatcgcag tggtgagtaa ccatgcatca    2400
tcaggagtac ggataaaatg cttgatggtc ggaagaggca taaattccgt cagccagttt    2460
agtctgacca tctcatctgt aacatcattg gcaacgctac ctttgccatg tttcagaaac    2520
aactctggcg catcgggctt cccatacaat cgatagattg tcgcacctga ttgcccgaca    2580
ttatcgcgag cccatttata cccatataaa tcagcatcca tgttggaatt taatcgcggc    2640
ctcgagcaag acgtttcccg ttgaatatgg ctcataacac cccttgtatt actgtttatg    2700
taagcagaca gttttattgt tcatgatgat atatttttat cttgtgcaat gtaacatcag    2760
agattttgag acacaacgtg gctttccccc cccccccatt attgaagcat ttatcagggt    2820
tattgtctca tgagcggata catatttgaa tgtatttaga aaataaaca aatagggt       2880
ccgcgcacat ttccccgaaa agtgccacct gacgtctaag aaaccattat tatcatgaca    2940
ttaacctata aaaataggcg tatcacgagg ccctttcgtc ctcgcgcgtt tcggtgatga    3000
cggtgaaaac ctctgacaca tgcagctccc ggagacggtc acagcttgtc tgtaagcgga    3060
tgccgggagc agacaagccc gtcagggcgc gtcagcgggt gttggcgggt gtcggggctg    3120
gcttaactat gcggcatcag agcagattgt actgagagtg caccatatgc ggtgtgaaat    3180
accgcacaga tgcgtaagga gaaaataccg catcagattg gctattggcc attgcatacg    3240
ttgtatccat atcataatat gtacatttat attggctcat gtccaacatt accgccatgt    3300
tgacattgat tattgactag ttattaatag taatcaatta cggggtcatt agttcatagc    3360
ccatatatgg agttccgcgt tacataactt acggtaaatg gcccgcctgg ctgaccgccc    3420
aacgaccccc gcccattgac gtcaataatg acgtatgttc ccatagtaac gccaataggg    3480
```

-continued

```
actttccatt gacgtcaatg ggtggagtat ttacggtaaa ctgcccactt ggcagtacat    3540
caagtgtatc atatgccaag tacgccccct attgacgtca atgacggtaa atggcccgcc    3600
tggcattatg cccagtacat gaccttatgg gactttccta cttggcagta catctacgta    3660
ttagtcatcg ctattaccat ggtgatgcgg ttttggcagt acatcaatgg gcgtggatag    3720
cggtttgact cacggggatt tccaagtctc cacccccattg acgtcaatgg gagtttgttt    3780
tggcaccaaa atcaacggga ctttccaaaa tgtcgtaaca actccgcccc attgacgcaa    3840
atgggcggta ggcgtgtacg gtgggaggtc tatataagca gagctcgttt agtgaaccgt    3900
cagatcgcct ggagacgcca tccacgctgt tttgacctcc atagaagaca ccgggaccga    3960
tccagcctcc gcggccggga acggtgcatt ggaacgcgga ttccccgtgc caagagtgac    4020
gtaagtaccg cctatagact ctataggcac accccctttgg ctcttatgca tgctatactg    4080
tttttggctt ggggcctata caccccccgct tccttatgct ataggtgatg gtatagctta    4140
gcctataggt gtgggttatt gaccattatt gaccactccc ctattggtga cgatactttc    4200
cattactaat ccataacatg gctctttgcc acaactatct ctattggcta tatgccaata    4260
ctctgtcctt cagagactga cacggactct gtattttttac aggatggggt cccattttatt    4320
atttacaaat tcacatatac aacaacgccg tccccgtgc ccgcagtttt tattaaacat    4380
agcgtgggat ctccacgcga atctcgggta cgtgttccgg acatgggctc ttctccggta    4440
gcggcggagc ttccacatcc gagccctggt cccatgcctc cagcggctca tggtcgctcg    4500
gcagctcctt gctcctaaca gtggaggcca gacttaggca cagcacaatg cccaccacca    4560
ccagtgtgcc gcacaaggcc gtggcggtag ggtatgtgtc tgaaaatgag cgtggagatt    4620
gggctcgcac ggctgacgca gatggaagac ttaaggcagc ggcagaagaa gatgcaggca    4680
gctgagttgt tgtattctga taagagtcag aggtaactcc cgttgcggtg ctgttaacgg    4740
tggagggcag tgtagtctga gcagtactcg ttgctgccgc gcgcgccacc agacataata    4800
gctgacagac taacagactg ttccttttcca tgggtctttt ctgcagtcac cgtcgtcgac    4860
acgtgtgatc agatatcgcg gccgctctag accaggcgcc tggatccgcc accatgccac    4920
tctgggtgtt cttctttgtg atcctcaccc tcagcaacag ctcccactgc tccccacctc    4980
ccccctttgac cctcaggatg cggcggtatt atgcagatgc catcttcacc aacagctacc    5040
ggaaggtgct ggcccagctg tccgcccgca aggcccctcca ggacatcatg agcaggtaga    5100
gatccagatc t                                                          5111
```

<210> SEQ ID NO 56
<211> LENGTH: 3327
<212> TYPE: DNA
<213> ORGANISM: Artificial Sequence
<220> FEATURE:
<223> OTHER INFORMATION: Description of Artificial Sequence:
      pGHRH1-29Yala1522SK construct

<400> SEQUENCE: 56

```
ggtaccgagc tcttacgcgt gctagcccgg gctcgagatc tgcgatctaa gtaagcttgc     60
caccatgcca ctctgggtgt tcttctttgt gatcctcacc ctcagcaaca gctcccactg    120
ctccccacct ccccctttga ccctcaggat gcggcggtat tatgcagatg ccatcttcac    180
caacagctac cggaaggtgc tggcccagct gtccgcccgc aaggcccctcc aggacatcat    240
gagcaggtag tctagagtcg ggcggccgg ccgcttcgag cagacatgat aagatacatt    300
gatgagtttg gacaaaccac aactagaatg cagtgaaaaa aatgctttat ttgtgaaatt    360
```

-continued

```
tgtgatgcta ttgctttatt tgtaaccatt ataagctgca ataaacaagt taacaacaac    420
aattgcattc attttatgtt tcaggttcag ggggaggtgt gggaggtttt ttaaagcaag    480
taaaacctct acaaatgtgg taaaatcgat aaggatccgt cgaccgatgc ccttgagagc    540
cttcaaccca gtcagctcct tccggtgggc gcggggcatg actatcgtcg ccgcacttat    600
gactgtcttc tttatcatgc aactcgtagg acaggtgccg gcagcgctct tccgcttcct    660
cgctcactga ctcgctgcgc tcggtcgttc ggctgcggcg agcggtatca gctcactcaa    720
aggcggtaat acggttatcc acagaatcag gggataacgc aggaaagaac atgtgagcaa    780
aaggccagca aaaggccagg aaccgtaaaa aggccgcgtt gctggcgttt ttccataggc    840
tccgcccccc tgacgagcat cacaaaaatc gacgctcaag tcagaggtgg cgaaacccga    900
caggactata aagataccag gcgtttcccc ctggaagctc cctcgtgcgc tctcctgttc    960
cgaccctgcc gcttaccgga tacctgtccg cctttctccc ttcgggaagc gtggcgcttt    1020
ctcaatgctc acgctgtagg tatctcagtt cggtgtaggt cgttcgctcc aagctgggct    1080
gtgtgcacga accccccgtt cagcccgacc gctgcgcctt atccggtaac tatcgtcttg    1140
agtccaaccc ggtaagacac gacttatcgc cactggcagc agccactggt aacaggatta    1200
gcagagcgag gtatgtaggc ggtgctacag agttcttgaa gtggtggcct aactacggct    1260
acactagaag gacagtattt ggtatctgcg ctctgctgaa gccagttacc ttcggaaaaa    1320
gagttggtag ctcttgatcc ggcaaacaaa ccaccgctgg tagcggtggt ttttttgttt    1380
gcaagcagca gattacgcgc agaaaaaaag gatctcaaga agatcctttg atcttttcta    1440
cggggtctga cgctcagtgg aacgaaaact cacgttaagg gattttggtc atgagattat    1500
caaaaaggat cttcacctag atccttttaa attaaaaatg aagttttaaa tcaatctaaa    1560
gtatatatga gtaaacttgg tctgacagtt accaatgctt aatcagtgag gcacctatct    1620
cagcgatctg tctatttcgt tcatccatag ttgcctgact ccccgtcgtg tagataacta    1680
cgatacggga gggcttacca tctggcccca gtgctgcaat gataccgcga gacccacgct    1740
caccggctcc agatttatca gcaataaacc agccagccgg aagggccgag cgcagaagtg    1800
gtcctgcaac tttatccgcc tccatccagt ctattaattg ttgccgggaa gctagagtaa    1860
gtagttcgcc agttaatagt ttgcgcaacg ttgttgccat tgctacaggc atcgtggtgt    1920
cacgctcgtc gtttggtatg gcttcattca gctccggttc ccaacgatca aggcgagtta    1980
catgatcccc catgttgtgc aaaaaagcgg ttagctcctt cggtcctccg atcgttgtca    2040
gaagtaagtt ggccgcagtg ttatcactca tggttatggc agcactgcat aattctctta    2100
ctgtcatgcc atccgtaaga tgcttttctg tgactggtga gtactcaacc aagtcattct    2160
gagaatagtg tatgcggcga ccgagttgct cttgcccggc gtcaatacgg ataataccg    2220 cgccacatag cagaacttta aaagtgctca tcattggaaa acgttcttcg ggcgaaaac    2280 tctcaaggat cttaccgctg ttgagatcca gttcgatgta acccactcgt gcacccaact    2340
gatcttcagc atcttttact ttcaccagcg tttctgggtg agcaaaaaca ggaaggcaaa    2400
atgccgcaaa aaagggaata agggcgacac ggaaatgttg aatactcata ctcttccttt    2460
ttcaatatta ttgaagcatt tatcagggtt attgtctcat gagcggatac atatttgaat    2520
gtatttagaa aaataaacaa ataggggttc cgcgcacatt tccccgaaaa gtgccacctg    2580
acgcgccctg tagcggcgca ttaagcgcgg cgggtgtggt ggttacgcgc agcgtgaccg    2640
ctacacttgc cagcgcccta gcgcccgctc ctttcgcttt cttcccttcc tttctcgcca    2700
cgttcgccgg ctttccccgt caagctctaa atcgggggct ccctttaggg ttccgattta    2760
```

-continued

```
gtgctttacg gcacctcgac cccaaaaaac ttgattaggg tgatggttca cgtagtgggc      2820
catcgccctg atagacggtt tttcgccctt tgacgttgga gtccacgttc tttaatagtg      2880
gactcttgtt ccaaactgga acaacactca accctatctc ggtctattct tttgatttat      2940
aagggatttt gccgatttcg gcctattggt taaaaaatga gctgatttaa caaaaattta      3000
acgcgaattt taacaaaata ttaacgttta caatttccca ttcgccattc aggctgcgca      3060
actgttggga agggcgatcg gtgcgggcct cttcgctatt acgccagccc aagctaccat      3120
gataagtaag taatattaag gtacgggagg tacttggagc ggccgcaata aaatatcttt      3180
attttcatta catctgtgtg ttggttttt gtgtgaatcg atagtactaa catacgctct      3240
ccatcaaaac aaaacgaaac aaaacaaact agcaaaatag gctgtcccca gtgcaagtgc      3300
aggtgccaga acatttctct atcgata                                          3327
```

<210> SEQ ID NO 57
<211> LENGTH: 3954
<212> TYPE: DNA
<213> ORGANISM: Artificial Sequence
<220> FEATURE:
<223> OTHER INFORMATION: Description of Artificial Sequence:
      pGHRH1-29Yala1522SK construct

<400> SEQUENCE: 57

```
ggtaccatcg ctggggagct gggggagggg tcgccttcct gccctaccca ggactccggg        60
tgcgaccgct cctctatctc tccagcccac caccactcca ccacttggac acgtctccct       120
cctccctgga gtcgctctag agggtttggg ggtctgagta aagaacccga agtagggata       180
cagtgtggcg gcaccttcca gaggccccgg gcgcagggta gaccggggcg gggcggcccg       240
cggacaggtg cagccccagg cgcaggcgca ctcgcgcctc ccggcgcagg cggtgaacct       300
cgccccaccc cagcccctcc gggggcagc tgggccgggt cgggaggggc ccaccagccc       360
gggagacact ccatatacgg ccaggcccgc tttacctggg ctccggccag gccgctcctt       420
ctttggtcag cacaggggac ccgggcgggg gcccaggccg ctaacccgcc ggggagggg       480 gctccagtgc ccaacaccca aatatggctc gagaagggga gcgacattcc agtgaggcgg       540
ctcgggggga gaacccgcgg gctatataaa acctgagcgt ggggaccagc ggccaccgca       600
gcggacagcg ccgagagaag cctcgcttcc ctcccgcggc gaccagggcc cagccggag       660 agcagcaggt gtagccacca agcttgccac catgccactc tgggtgttct tctttgtgat       720 cctcacctc agcaacagct cccactgctc cccacctccc cctttgaccc tcaggatgcg       780
gcggtattat gcagatgcca tcttcaccaa cagctaccgg aaggtgctgg cccagctgtc       840
cgcccgcaag gccctccagg acatcatgag caggtagtct agagtcgggg cggccggccg       900
cttcgagcag acatgataag atacattgat gagtttggac aaaccacaac tagaatgcag       960 tgaaaaaat gctttatttg tgaaatttgt gatgctattg cttatttgt aaccattata      1020 agctgcaata aacaagttaa caacaacaat tgcattcatt ttatgtttca ggttcagggg      1080
gaggtgtggg aggttttta aagcaagtaa acctctaca aatgtggtaa atcgataag        1140 gatccgtcga ccgatgccct tgagagcctt caacccagtc agctccttcc ggtgggcgcg      1200
gggcatgact atcgtcgccg cacttatgac tgtcttcttt atcatgcaac tcgtaggaca      1260
ggtgccggca gcgctcttcc gcttcctcgc tcactgactc gctgcgctcg gtcgttcggc      1320
tgcggcgagc ggtatcagct cactcaaagg cggtaatacg ttatccaca gaatcagggg       1380 ataacgcagg aaagaacatg tgagcaaaag gccagcaaaa ggccaggaac cgtaaaaagg      1440
```

```
ccgcgttgct ggcgtttttc cataggctcc gcccccctga cgagcatcac aaaaatcgac    1500
gctcaagtca gaggtggcga aacccgacag gactataaag ataccaggcg tttcccctg     1560 gaagctccct cgtgcgctct cctgttccga ccctgccgct taccggatac ctgtccgcct    1620
ttctcccttc gggaagcgtg gcgctttctc aatgctcacg ctgtaggtat ctcagttcgg    1680
tgtaggtcgt tcgctccaag ctgggctgtg tgcacgaacc ccccgttcag cccgaccgct    1740
gcgccttatc cggtaactat cgtcttgagt ccaacccggt aagacacgac ttatcgccac    1800
tggcagcagc cactggtaac aggattagca gagcgaggta tgtaggcggt gctacagagt    1860
tcttgaagtg gtggcctaac tacggctaca ctagaaggac agtatttggt atctgcgctc    1920
tgctgaagcc agttaccttc ggaaaaagag ttggtagctc ttgatccggc aaacaaacca    1980
ccgctggtag cggtggtttt tttgtttgca agcagcagat tacgcgcaga aaaaaggat    2040 ctcaagaaga ccctttgatc ttttctacgg ggtctgacgc tcagtggaac gaaaactcac    2100
gttaagggat tttggtcatg agattatcaa aaaggatctt cacctagatc cttttaaatt    2160
aaaaatgaag ttttaaatca atctaaagta tatatgagta aacttggtct gacagttacc    2220
aatgcttaat cagtgaggca cctatctcag cgatctgtct atttcgttca tccatagttg    2280
cctgactccc cgtcgtgtag ataactacga tacgggaggg cttaccatct ggccccagtg    2340
ctgcaatgat accgcgagac ccacgctcac cggctccaga tttatcagca ataaaccagc    2400
cagccggaag ggccgagcgc agaagtggtc ctgcaacttt atccgcctcc atccagtcta    2460
ttaattgttg ccgggaagct agagtaagta gttcgccagt taatagtttg cgcaacgttg    2520
ttgccattgc tacaggcatc gtggtgtcac gctcgtcgtt tggtatggct tcattcagct    2580
ccggttccca acgatcaagg cgagttacat gatcccccat gttgtgcaaa aaagcggtta    2640
gctccttcgg tcctccgatc gttgtcagaa gtaagttggc cgcagtgtta tcactcatgg    2700
ttatggcagc actgcataat tctcttactg tcatgccatc cgtaagatgc ttttctgtga    2760
ctggtgagta ctcaaccaag tcattctgag aatagtgtat gcggcgaccg agttgctctt    2820
gcccggcgtc aatacgggat aataccgcgc cacatagcag aactttaaaa gtgctcatca    2880
ttggaaaacg ttcttcgggg cgaaaactct caaggatctt accgctgttg agatccagtt    2940
cgatgtaacc cactcgtgca cccaactgat cttcagcatc ttttactttc accagcgttt    3000
ctgggtgagc aaaaacagga aggcaaaatg ccgcaaaaaa gggaataagg gcgacacgga    3060
aatgttgaat actcatactc ttcctttttc aatattattg aagcatttat cagggttatt    3120
gtctcatgag cggatacata tttgaatgta tttagaaaaa taaacaaata ggggttccgc    3180
gcacatttcc ccgaaaagtg ccacctgacg cgccctgtag cggcgcatta agcgcggcgg    3240
gtgtggtggt tacgcgcagc gtgaccgcta cacttgccag cgccctagcg cccgctcctt    3300
tcgctttctt cccttccttt ctcgccacgt tcgccggctt tccccgtcaa gctctaaatc    3360
gggggctccc tttagggttc cgatttagtg ctttacggca cctcgacccc aaaaaacttg    3420
attagggtga tggttcacgt agtgggccat cgccctgata cggttttt cgcccttga     3480 cgttggagtc cacgttcttt aatagtggac tcttgttcca aactggaaca cactcaacc    3540 ctatctcggt ctattctttt gatttataag ggattttgcc gatttcggcc tattggttaa    3600
aaaatgagct gatttaacaa aaatttaacg cgaatttta caaatatta acgtttacaa    3660 tttcccattc gccattcagg ctgcgcaact gttgggaagg gcgatcggtg cgggcctctt    3720
cgctattacg ccagcccaag ctaccatgat aagtaagtaa tattaaggta cgggaggtac    3780
```

-continued

| | |
|---|---|
| ttggagcggc cgcaataaaa tatctttatt ttcattacat ctgtgtgttg gttttttgtg | 3840 |
| tgaatcgata gtactaacat acgctctcca tcaaaacaaa acgaaacaaa acaaactagc | 3900 |
| aaaataggct gtccccagtg caagtgcagg tgccagaaca tttctctatc gata | 3954 |

<210> SEQ ID NO 58
<211> LENGTH: 5283
<212> TYPE: DNA
<213> ORGANISM: Artificial Sequence
<220> FEATURE:
<223> OTHER INFORMATION: Description of Artificial Sequence:
    pGHRH1-29Yala1522SK2014 construct

<400> SEQUENCE: 58

| | |
|---|---|
| ggtaccgcta taggagagaa aagagctgca ctgagcaccc tccttcccct ttaaatgtca | 60 |
| acagattagg agtcagtgaa tgacagcaca cctcttgcta ccttagagac caaaatttaa | 120 |
| gctactcccc ttaagctata gctagagtgc acctgccagt gtctttagtc cccactgatg | 180 |
| gaacaggacc caaggtattg aagatggaac atagttattc attcatcctc taatttaaaa | 240 |
| agctggatat gctgtacagc agaaattgac ggaacaatgt aaatcaacta taacagaaga | 300 |
| aataaaaacc tggggggaaa gaagctgact atgaaacccc aggagctttc tacatgggcc | 360 |
| tggactcacc aaactcttta ttttgtaatg gacttctgac atttttagga agggctgtcc | 420 |
| tgatgtgggc tatagaagag ggtttcacat gcttcttcaa gaggacccac actgtcccag | 480 |
| ttgctgagtc ccaccaccag atgctagtgg cagctatttg gggaacactt aggcactaca | 540 |
| aaaaaatgag tgattccatt ctggctcaca ccatatccct gatgtacccc ttaaagcatg | 600 |
| tcactgagtt catcacagaa aattgtttcc cctgtgcctt ccacaacaag gttagagctg | 660 |
| tccttggggc caggggaagg gggcagggag tgagaagcac caactggata acctcctctg | 720 |
| accccccactc cacccttacca taagtagatc caaatccttc tagaaaatta ggaaggcata | 780 |
| tcccccatata tcagcgatat aaatagaact gcttcagcgc tctggtagac ggtgactctc | 840 |
| caaggtggac tgggaggcag cctggccttg gctgggcatc gtcctctaaa tagaaagatg | 900 |
| aacttgttca gcctttccag aaggaaaact gctgcccagc ctacagtgca acgtccttgt | 960 |
| cttccatctg gaggaagcac gggtgacata tcatctagta agggcacctc tctgtttcca | 1020 |
| cctccaggtc gagggtgtg acccttactt ctcagcctca agggagggac actcaacccc | 1080 |
| ccaaaaagac atgagggcgc tcagctcggc ccaccgcacc ccggaccgga gccgtcaccc | 1140 |
| cccgaaattc actcccttca caagccccca agcgcgttct ctggtgcgga ctgctccggg | 1200 |
| gccctggctt tgtgcccagc gttgtcagag ccaccgccct gagcctgtcc ccgggagccc | 1260 |
| cgcgcctcct cccaccgctc cgctctcgcg ccccgcggcc agttgtctgc cccgagacag | 1320 |
| ctgcgcgccc tcccgctgcc ggtggccctc tccggtgggg gtggggaccg acagggtcag | 1380 |
| ccctccggat ccggggcgct ccgggtagcg gggagaagtg atcgctgggg agctggggga | 1440 |
| ggggtcgcct tcctgcccta cccaggactc cgggtgcgac cgctcctcta tctctccagc | 1500 |
| ccaccaccac tccaccactt ggacacgtct ccctcctccc tggagtcgct ctagagggtt | 1560 |
| tgggggtctg agtaaagaac ccgaagtagg gatacagtgt ggcggcacct tccagaggcc | 1620 |
| ccgggcgcag ggtagaccgg ggcgggggcgg cccgcgcgaca ggtgcagccc caggcgcagg | 1680 |
| cgcactcgcg cctcccggcg caggcggtga acctcgcccc accccagccc ctccgggggg | 1740 |
| cagctgggcc gggtcgggag gggcccacca gcccggagga cactccatat acggccaggc | 1800 |
| ccgctttacc tgggctccgg ccaggccgct ccttctttgg tcagcacagg ggacccgggc | 1860 |

-continued

```
gggggcccag gccgctaacc cgccggggga gggggctcca gtgcccaaca cccaaatatg      1920
gctcgagaag gggagcgaca ttccagtgag gcggctcggg gggagaaccc gcgggctata      1980
taaaacctga gcgtggggac cagcggccaa gcttgccacc atgccactct gggtgttctt      2040
ctttgtgatc ctcacctca gcaacagctc ccactgctcc ccacctcccc ctttgacccc       2100
caggatgcgg cggtattatg cagatgccat cttcaccaac agctaccgga aggtgctggc      2160
ccagctgtcc gcccgcaagg ccctccagga catcatgagc aggtagtcta gagtcggggc      2220
ggccggccgc ttcgagcaga catgataaga tacattgatg agtttggaca aaccacaact      2280
agaatgcagt gaaaaaaatg ctttatttgt gaaatttgtg atgctattgc tttatttgta      2340
accattataa gctgcaataa acaagttaac aacaacaatt gcattcattt tatgtttcag      2400
gttcaggggg aggtgtggga ggtttttaa agcaagtaaa acctctacaa atgtggtaaa       2460
atcgataagg atccgtcgac cgatgcccctt gagagccttc aacccagtca gctccttccg     2520
gtgggcgcgg ggcatgacta tcgtcgccgc acttatgact gtcttcttta tcatgcaact      2580
cgtaggacag gtgccggcag cgctcttccg cttcctcgct cactgactcg ctgcgctcgg      2640
tcgttcggct gcggcgagcg gtatcagctc actcaaaggc ggtaatacgg ttatccacag      2700
aatcagggga taacgcagga agaacatgt gagcaaaagg ccagcaaaag gccaggaacc       2760
gtaaaaaggc cgcgttgctg gcgttttcc ataggctccg ccccctgac gagcatcaca        2820 aaaatcgacg ctcaagtcag aggtggcgaa acccgacagg actataaaga taccaggcgt      2880
ttccccctgg aagctccctc gtgcgctctc ctgttccgac cctgccgctt accggatacc      2940
tgtccgcctt tctcccttcg ggaagcgtgg cgctttctca atgctcacgc tgtaggtatc      3000
tcagttcggt gtaggtcgtt cgctccaagc tgggctgtgt gcacgaaccc cccgttcagc     3060
ccgaccgctg cgccttatcc ggtaactatc gtcttgagtc aacccggta agacacgact       3120 tatcgccact ggcagcagcc actggtaaca ggattagcag agcgaggtat gtaggcggtg      3180
ctacagagtt cttgaagtgg tggcctaact acggctacac tagaaggaca gtatttggta     3240
tctgcgctct gctgaagcca gttaccttcg aaaaagagt tggtagctct tgatccggca      3300
aacaaaccac cgctggtagc ggtggttttt tgtttgcaa gcagcagatt acgcgcagaa       3360
aaaaaggatc tcaagaagat cctttgatct tttctacggg gtctgacgct cagtggaacg     3420
aaaactcacg ttaagggatt ttggtcatga gattatcaaa aaggatcttc acctagatcc     3480 tttaaatta aaatgaagt tttaaatcaa tctaaagtat atatgagtaa acttggtctg       3540
acagttacca atgcttaatc agtgaggcac ctatctcagc gatctgtcta tttcgttcat     3600
ccatagttgc ctgactcccc gtcgtgtaga taactacgat acgggagggc ttaccatctg      3660
gccccagtgc tgcaatgata ccgcgagacc cacgctcacc ggctccagat ttatcagcaa     3720
taaaccagcc agccggaagg gccgagcgca gaagtggtcc tgcaacttta tccgcctcca     3780
tccagtctat taattgttgc cgggaagcta gagtaagtag ttcgccagtt aatagtttgc     3840
gcaacgttgt tgccattgct acaggcatcg tggtgtcacg ctcgtcgttt ggtatggctt     3900
cattcagctc cggttcccaa cgatcaaggc gagttacatg atcccccatg ttgtgcaaaa    3960
aagcggttag ctccttcggt cctccgatcg ttgtcagaag taagttggcc gcagtgttat     4020
cactcatggt tatggcagca ctgcataatt ctcttactgt catgccatcc gtaagatgct     4080
tttctgtgac tggtgagtac tcaaccaagt cattctgaga atagtgtatg cggcgaccga     4140
gttgctcttg cccggcgtca atacgggata ataccgcgcc acatagcaga actttaaaag     4200
tgctcatcat tggaaaacgt tcttcggggc gaaaactctc aaggatctta ccgctgttga    4260
```

```
gatccagttc gatgtaaccc actcgtgcac ccaactgatc ttcagcatct tttactttca    4320
ccagcgtttc tgggtgagca aaaacaggaa ggcaaaatgc cgcaaaaaag ggaataaggg    4380
cgacacggaa atgttgaata ctcatactct tcctttttca atattattga agcatttatc    4440
agggttattg tctcatgagc ggatacatat ttgaatgtat ttagaaaaat aaacaaatag    4500
gggttccgcg cacatttccc cgaaaagtgc cacctgacgc gccctgtagc ggcgcattaa    4560
gcgcggcggg tgtggtggtt acgcgcagcg tgaccgctac acttgccagc gccctagcgc    4620
ccgctccttt cgctttcttc ccttcctttc tcgccacgtt cgccggcttt ccccgtcaag    4680
ctctaaatcg gggctccct ttagggttcc gatttagtgc tttacggcac ctcgacccca    4740
aaaaacttga ttagggtgat ggttcacgta gtgggccatc gccctgatag acggtttttc    4800
gccctttgac gttggagtcc acgttcttta atagtggact cttgttccaa actggaacaa    4860
cactcaaccc tatctcggtc tattcttttg atttataagg gattttgccg atttcggcct    4920
attggttaaa aaatgagctg atttaacaaa aatttaacgc gaattttaac aaaatattaa    4980
cgtttacaat ttcccattcg ccattcaggc tgcgcaactg ttgggaaggg cgatcggtgc    5040
gggcctcttc gctattacgc cagcccaagc taccatgata agtaagtaat attaaggtac    5100
gggaggtact tggagcggcc gcaataaaat atctttattt tcattacatc tgtgtgttgg    5160
ttttttgtgt gaatcgatag tactaacata cgctctccat caaaacaaaa cgaaacaaaa    5220
caaactagca aaataggctg tccccagtgc aagtgcaggt gccagaacat ttctctatcg    5280
ata                                                                  5283
```

<210> SEQ ID NO 59
<211> LENGTH: 5188
<212> TYPE: DNA
<213> ORGANISM: Artificial Sequence
<220> FEATURE:
<223> OTHER INFORMATION: Description of Artificial Sequence:
      pGHRH1-44YWTCMV construct

<400> SEQUENCE: 59

```
gctgtgcctt ctagttgcca gccatctgtt gtttgcccct cccccgtgcc ttccttgacc     60
ctggaaggtg ccactcccac tgtccttttcc taataaaatg aggaaattgc atcgcattgt   120
ctgagtaggt gtcattctat tctggggggt ggggtggggc aggacagcaa ggggggaggat  180 tgggaagaca atagcaggca tgctggggat gcggtgggct ctatgggtac ccaggtgctg   240
aagaattgac ccggttcctc ctgggccaga agaagcagg cacatcccct tctctgtgac    300
acaccctgtc cacgccccctg gttcttagtt ccagccccac tcataggaca ctcatagctc   360
aggagggctc cgccttcaat cccacccgct aaagtacttg gagcggtctc tccctcccctc  420 atcagcccac caaccaaac ctagcctcca agagtgggaa gaaattaaag caagataggc    480
tattaagtgc agagggagag aaaatgcctc caacatgtga ggaagtaatg agagaaatca   540
tagaatttct tccgcttcct cgctcactga ctcgctgcgc tcggtcgttc ggctgcggcg   600
agcggtatca gctcactcaa aggcggtaat acgttatcc acagaatcag ggataacgc     660 aggaaagaac atgtgagcaa aaggccagca aaaggccagg aaccgtaaaa aggccgcgtt   720
gctggcgttt ttccataggc tccgcccccc tgacgagcat cacaaaaatc gacgctcaag   780
tcagaggtgg cgaaacccga caggactata aagataccag gcgtttcccc ctggaagctc   840
cctcgtgcgc tctcctgttc cgaccctgcc gcttaccgga tacctgtccg cctttctccc   900
ttcgggaagc gtggcgcttt ctcatagctc acgctgtagg tatctcagtt cggtgtaggt   960
```

-continued

```
cgttcgctcc aagctgggct gtgtgcacga acccccgtt cagcccgacc gctgcgcctt    1020
atccggtaac tatcgtcttg agtccaaccc ggtaagacac gacttatcgc cactggcagc   1080
agccactggt aacaggatta gcagagcgag gtatgtaggc ggtgctacag agttcttgaa   1140
gtggtggcct aactacggct acactagaag aacagtattt ggtatctgcg ctctgctgaa   1200
gccagttacc ttcggaaaaa gagttggtag ctcttgatcc ggcaaacaaa ccaccgctgg   1260
tagcggtggt ttttttgttt gcaagcagca gattacgcgc agaaaaaaag gatctcaaga   1320
agatcctttg atcttttcta cggggtctga cgctcagtgg aacgaaaact cacgttaagg   1380
gattttggtc atgagattat caaaaaggat cttcacctag atccttttaa attaaaaatg   1440
aagttttaaa tcaatctaaa gtatatatga gtaaacttgg tctgacagtt accaatgctt   1500
aatcagtgag gcacctatct cagcgatctg tctatttcgt tcatccatag ttgcctgact   1560 cgggggggggg gggcgctgag gtctgcctcg tgaagaaggt gttgctgact cataccaggc   1620
ctgaatcgcc ccatcatcca gccagaaagt gagggagcca cggttgatga gagctttgtt   1680
gtaggtggac cagttggtga ttttgaactt ttgctttgcc acggaacggt ctgcgttgtc   1740
gggaagatgc gtgatctgat ccttcaactc agcaaaagtt cgatttattc aacaaagccg   1800
ccgtcccgtc aagtcagcgt aatgctctgc cagtgttaca accaattaac caattctgat   1860
tagaaaaact catcgagcat caaatgaaac tgcaatttat tcatatcagg attatcaata   1920
ccatattttt gaaaaagccg tttctgtaat gaaggagaaa actcaccgag gcagttccat   1980
aggatggcaa gatcctggta tcggtctgcg attccgactc gtccaacatc aatacaacct   2040
attaatttcc cctcgtcaaa ataaggtta tcaagtgaga atcaccatg agtgacgact   2100 gaatccggtg agaatggcaa aagcttatgc atttctttcc agacttgttc aacaggccag   2160
ccattacgct cgtcatcaaa atcactcgca tcaaccaaac cgttattcat tcgtgattgc   2220
gcctgagcga gacgaaatac gcgatcgctg ttaaaaggac aattacaaac aggaatcgaa   2280
tgcaaccggc gcaggaacac tgccagcgca tcaacaatat tttcacctga atcaggatat   2340
tcttctaata cctggaatgc tgttttcccg gggatcgcag tggtgagtaa ccatgcatca   2400
tcaggagtac ggataaaatg cttgatggtc ggaagaggca taaattccgt cagccagttt   2460
agtctgacca tctcatctgt aacatcattg gcaacgctac cttttgccatg tttcagaaac   2520 aactctggcg catcgggctt cccatacaat cgatagattg tcgcacctga ttgcccgaca   2580
ttatcgcgag cccatttata cccatataaa tcagcatcca tgttggaatt taatcgcggc   2640
ctcgagcaag acgtttcccg ttgaatatgg ctcataacac cccttgtatt actgtttatg   2700
taagcagaca gttttattgt tcatgatgat atatttttat cttgtgcaat gtaacatcag   2760
agattttgag acacaacgtg ctttcccccc ccccccatt attgaagcat ttatcagggt   2820
tattgtctca tgagcggata catatttgaa tgtatttaga aaataaaca aatagggggtt   2880 ccgcgcacat ttccccgaaa agtgccacct gacgtctaag aaaccattat tatcatgaca   2940
ttaacctata aaataggcg tatcacgagg ccctttcgtc ctcgcgcgtt tcggtgatga   3000
cggtgaaaac ctctgacaca tgcagctccc ggagacggtc acagcttgtc tgtaagcgga   3060
tgccgggagc agacaagccc gtcagggcgc gtcagcgggt gttggcgggt gtcgggctg   3120 gcttaactat gcggcatcag agcagattgt actgagagtg caccatatgc ggtgtgaaat   3180
accgcacaga tgcgtaagga gaaaataccg catcagattg gctattggcc attgcatacg   3240
ttgtatccat atcataatat gtacatttat attggctcat gtccaacatt accgccatgt   3300
```

```
tgacattgat tattgactag ttattaatag taatcaatta cggggtcatt agttcatagc    3360
ccatatatgg agttccgcgt tacataactt acggtaaatg gcccgcctgg ctgaccgccc    3420
aacgacccc gcccattgac gtcaataatg acgtatgttc ccatagtaac gccaataggg    3480
actttccatt gacgtcaatg ggtggagtat ttacggtaaa ctgcccactt ggcagtacat    3540
caagtgtatc atatgccaag tacgcccct attgacgtca atgacggtaa atggcccgcc    3600
tggcattatg cccagtacat gaccttatgg gactttccta cttggcagta catctacgta    3660
ttagtcatcg ctattaccat ggtgatgcgg ttttggcagt acatcaatgg gcgtggatag    3720
cggtttgact cacggggatt tccaagtctc caccccattg acgtcaatgg gagtttgttt    3780
tggcaccaaa atcaacggga ctttccaaaa tgtcgtaaca actccgcccc attgacgcaa    3840
atgggcggta ggcgtgtacg gtgggaggtc tatataagca gagctcgttt agtgaaccgt    3900
cagatcgcct ggagacgcca tccacgctgt tttgacctcc atagaagaca ccgggaccga    3960
tccagcctcc gcggccggga acgtgcatt ggaacgcgga ttccccgtgc aagagtgac    4020
gtaagtaccg cctatagact ctataggcac accccttgg ctcttatgca tgctatactg    4080
tttttggctt ggggcctata caccccgct tccttatgct ataggtgatg gtatagctta    4140
gcctataggt gtgggttatt gaccattatt gaccactccc ctattggtga cgatactttc    4200
cattactaat ccataacatg gctctttgcc acaactatct ctattggcta tatgccaata    4260
ctctgtcctt cagagactga cacggactct gtatttttac aggatggggt cccatttatt    4320
atttacaaat tcacatatac aacaacgccg tccccgtgc ccgcagtttt tattaaacat    4380
agcgtgggat ctccacgcga atctcgggta cgtgttccgg acatgggctc ttctccggta    4440
gcggcggagc ttccacatcc gagccctggt cccatgcctc cagcggctca tggtcgctcg    4500
gcagctcctt gctcctaaca gtggaggcca gacttaggca cagcacaatg cccaccacca    4560
ccagtgtgcc gcacaaggcc gtggcggtag ggtatgtgtc tgaaaatgag cgtggagatt    4620
gggctcgcac ggctgacgca gatggaagac ttaaggcagc ggcagaagaa gatgcaggca    4680
gctgagttgt tgtattctga taagagtcag aggtaactcc cgttgcggtg ctgttaacgg    4740
tggagggcag tgtagtctga gcagtactcg ttgctgccgc gcgcgccacc agacataata    4800
gctgacagac taacagactg ttccttttcca tgggtctttt ctgcagtcac cgtcgtcgac    4860
acgtgtgatc agatatcgcg gccgctctag accaggcgcg tggatccgcc accatgccac    4920
tctgggtgtt cttctttgtg atcctcaccc tcagcaacag ctcccactgc tccccacctc    4980
cccctttgac cctcaggatg cggcggtatt atgcagatgc catcttcacc aacagctacc    5040
ggaaggtgct gggccagctg tccgcccgca gctgctcca ggacatcatg agcaggcagc    5100
agggagagag aaaccaagag caaggagcaa gggtgcggct ttgaagatct tagtagtagt    5160
aggcggccgc tctagaggat ccagatct                                        5188
```

<210> SEQ ID NO 60
<211> LENGTH: 5254
<212> TYPE: DNA
<213> ORGANISM: Artificial Sequence
<220> FEATURE:
<223> OTHER INFORMATION: Description of Artificial Sequence:
pGHRH1-44WTGHpep construct

<400> SEQUENCE: 60

```
gctgtgcctt ctagttgcca gccatctgtt gtttgcccct ccccgtgcc ttccttgacc       60
ctggaaggtg ccactcccac tgtcctttcc taataaaatg aggaaattgc atcgcattgt      120
```

```
ctgagtaggt gtcattctat tctggggggt ggggtggggc aggacagcaa ggggaggat      180 tgggaagaca atagcaggca tgctggggat gcggtgggct ctatgggtac ccaggtgctg      240
aagaattgac ccggttcctc ctgggccaga aagaagcagg cacatcccct tctctgtgac      300
acaccctgtc cacgccctg gttcttagtt ccagccccac tcataggaca ctcatagctc       360
aggagggctc cgccttcaat cccacccgct aaagtacttg gagcggtctc tccctccctc      420
atcagcccac caaaccaaac ctagcctcca agagtgggaa gaaattaaag caagataggc      480
tattaagtgc agagggagag aaaatgcctc caacatgtga ggaagtaatg agagaaatca      540
tagaatttct tccgcttcct cgctcactga ctcgctgcgc tcggtcgttc ggctgcggcg      600
agcggtatca gctcactcaa aggcggtaat acggttatcc acagaatcag gggataacgc      660
aggaaagaac atgtgagcaa aaggccagca aaaggccagg aaccgtaaaa aggccgcgtt      720
gctggcgttt ttccataggc tccgccccc tgacgagcat cacaaaaatc gacgctcaag       780
tcagaggtgg cgaaacccga caggactata aagataccag gcgtttcccc ctggaagctc      840
cctcgtgcgc tctcctgttc cgaccctgcc gcttaccgga tacctgtccg cctttctccc      900
ttcgggaagc gtggcgcttt ctcatagctc acgctgtagg tatctcagtt cggtgtaggt      960
cgttcgctcc aagctgggct gtgtgcacga accccccgtt cagcccgacc gctgcgcctt     1020
atccggtaac tatcgtcttg agtccaaccc ggtaagacac gacttatcgc cactggcagc     1080
agccactggt aacaggatta gcagagcgag gtatgtaggc ggtgctacag agttcttgaa     1140
gtggtggcct aactacggct acactagaag aacagtattt ggtatctgcg ctctgctgaa     1200
gccagttacc ttcggaaaaa gagttggtag ctcttgatcc ggcaaacaaa ccaccgctgg     1260
tagcggtggt ttttttgttt gcaagcagca gattacgcgc agaaaaaaag gatctcaaga     1320
agatcctttg atcttttcta cggggtctga cgctcagtgg aacgaaaact cacgttaagg     1380
gattttggtc atgagattat caaaaaggat cttcacctag atccttttaa attaaaaatg     1440
aagttttaaa tcaatctaaa gtatatatga gtaaacttgg tctgacagtt accaatgctt     1500
aatcagtgag gcacctatct cagcgatctg tctatttcgt tcatccatag ttgcctgact     1560 cgggggggg gggcgctgag gtctgcctcg tgaagaaggt gttgctgact cataccaggc      1620
ctgaatcgcc ccatcatcca gccagaaagt gagggagcca cggttgatga gagctttgtt     1680
gtaggtggac cagttggtga ttttgaactt ttgctttgcc acggaacggt ctgcgttgtc     1740
gggaagatgc gtgatctgat ccttcaactc agcaaaagtt cgatttattc aacaaagccg     1800
ccgtcccgtc aagtcagcgt aatgctctgc cagtgttaca accaattaac caattctgat     1860
tagaaaaact catcgagcat caaatgaaac tgcaatttat tcatatcagg attatcaata     1920 ccatatttt gaaaaagccg tttctgtaat gaaggagaaa actcaccgag gcagttccat      1980
aggatggcaa gatcctggta tcggtctgcg attccgactc gtccaacatc aatacaacct     2040
attaatttcc cctcgtcaaa aataaggtta tcaagtgaga aatcaccatg agtgacgact     2100
gaatccggtg agaatggcaa aagcttatgc atttctttcc agacttgttc aacaggccag     2160
ccattacgct cgtcatcaaa atcactcgca tcaaccaaac cgttattcat tcgtgattgc     2220
gcctgagcga gacgaaatac gcgatcgctg ttaaaaggac aattacaaac aggaatcgaa     2280
tgcaaccggc gcaggaacac tgccagcgca tcaacaatat tttcacctga atcaggatat     2340
tcttctaata cctggaatgc tgttttcccg gggatcgcag tggtgagtaa ccatgcatca     2400
tcaggagtac ggataaaatg cttgatggtc ggaagaggca taaattccgt cagccagttt     2460
agtctgacca tctcatctgt aacatcattg gcaacgctac ctttgccatg tttcagaaac     2520
```

-continued

```
aactctggcg catcgggctt cccatacaat cgatagattg tcgcacctga ttgcccgaca    2580
ttatcgcgag cccatttata cccatataaa tcagcatcca tgttggaatt taatcgcggc    2640
ctcgagcaag acgtttcccg ttgaatatgg ctcataacac cccttgtatt actgtttatg    2700
taagcagaca gttttattgt tcatgatgat atatttttat cttgtgcaat gtaacatcag    2760
agattttgag acacaacgtg gctttccccc cccccccatt attgaagcat ttatcagggt    2820
tattgtctca tgagcggata catatttgaa tgtatttaga aaaataaaca aatagggggtt   2880 ccgcgcacat ttccccgaaa agtgccacct gacgtctaag aaaccattat tatcatgaca    2940
ttaacctata aaataggcg tatcacgagg ccctttcgtc ctcgcgcgtt tcggtgatga    3000
cggtgaaaac ctctgacaca tgcagctccc ggagacggtc acagcttgtc tgtaagcgga    3060
tgccgggagc agacaagccc gtcagggcgc gtcagcgggt gttggcgggt gtcggggctg    3120
gcttaactat gcggcatcag agcagattgt actgagagtg caccatatgc ggtgtgaaat    3180
accgcacaga tgcgtaagga gaaaataccg catcagattg gctattggcc attgcatacg    3240
ttgtatccat atcataatat gtacatttat attggctcat gtccaacatt accgccatgt    3300
tgacattgat tattgactag ttattaatag taatcaatta cggggtcatt agttcatagc    3360
ccatatatgg agttccgcgt tacataactt acggtaaatg gcccgcctgg ctgaccgccc    3420 aacgacccc gcccattgac gtcaataatg acgtatgttc ccatagtaac gccaataggg    3480
actttccatt gacgtcaatg ggtggagtat ttacggtaaa ctgcccactt ggcagtacat    3540
caagtgtatc atatgccaag tacgcccct attgacgtca atgacggtaa atggcccgcc    3600
tggcattatg cccagtacat gaccttatgg gactttccta cttggcagta catctacgta    3660
ttagtcatcg ctattaccat ggtgatgcgg ttttggcagt acatcaatgg gcgtggatag    3720
cggtttgact cacggggatt tccaagtctc cacccattg acgtcaatgg gagtttgttt    3780
tggcaccaaa atcaacggga ctttccaaaa tgtcgtaaca actccgcccc attgacgcaa    3840
atgggcggta ggcgtgtacg gtgggaggtc tatataagca gagctcgttt agtgaaccgt    3900
cagatcgcct ggagacgcca tccacgctgt tttgacctcc atagaagaca ccgggaccga    3960
tccagcctcc gcggccggga acggtgcatt ggaacgcgga ttccccgtgc caagagtgac    4020
gtaagtaccg cctatagact ctataggcac accccttttgg ctcttatgca tgctatactg    4080
tttttggctt ggggcctata caccccgct tccttatgct ataggtgatg gtatagctta    4140
gcctataggt gtgggttatt gaccattatt gaccactccc ctattggtga cgatactttc    4200
cattactaat ccataacatg gctctttgcc acaactatct ctattggcta tatgccaata    4260
ctctgtcctt cagagactga cacggactct gtattttac aggatggggt cccatttatt    4320
atttacaaat tcacatatac aacaacgccg tccccgtgc ccgcagtttt tattaaacat    4380
agcgtgggat ctcacgcga atctcgggta cgtgttccgg acatgggctc ttctccggta    4440
gcggcggagc ttccacatcc gagccctggt cccatgcctc cagcggctca tggtcgctcg    4500
gcagctcctt gctcctaaca gtggaggcca gacttaggca cagcacaatg cccaccacca    4560
ccagtgtgcc gcacaaggcc gtggcggtag ggtatgtgtc tgaaaatgag cgtggagatt    4620
gggctcgcac ggctgacgca gatggaagac ttaaggcagc ggcagaagaa gatgcaggca    4680
gctgagttgt tgtattctga taagagtcag aggtaactcc cgttgcggtg ctgttaacgg    4740
tggagggcag tgtagtctga gcagtactcg ttgctgccgc gcgcgccacc agacataata    4800
gctgacagac taacagactg ttcctttcca tgggtctttt ctgcagtcac cgtcgtcgac    4860
```

```
acgtgtgatc agatatcgcg gccgctctag accaggcgcc tggatccgcc accatgccac    4920
tctgggtgtt cttctttgtg atcctcaccc tcagcaacag ctcccactgc tccccacctc    4980 ccccttttgac cctcaggatg cggcggtatt atgcagatgc catcttcacc aacagctacc    5040
ggaaggtgct gggccagctg tccgcccgca agctgctcca ggacatcatg agcaggcagc    5100
agggagagag aaaccaagag caaggagcaa gggtgcggct tgggcggaaa gtagaaacgt    5160
ttctgcgtat tgtacagtgt cgtagcgtag aagggagctg tgggttttga agatcttagt    5220
agtagtaggc ggccgctcta gaggatccag atct                                5254

<210> SEQ ID NO 61
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 61
agatctgcca ccatgccact ctgggtgttc ttctttgtg                             39

<210> SEQ ID NO 62
<211> LENGTH: 36
<212> TYPE: DNA
<213> ORGANISM: Artificial Sequence
<220> FEATURE:
<223> OTHER INFORMATION: Description of Artificial Sequence:  Primer

<400> SEQUENCE: 62
ggatccaagc cgcacccttg ctccttgctc ttggtt                                36

<210> SEQ ID NO 63
<211> LENGTH: 492
<212> TYPE: DNA
<213> ORGANISM: Artificial Sequence
<220> FEATURE:
<223> OTHER INFORMATION: Description of Artificial Sequence:  Primer

<400> SEQUENCE: 63
ggttttttgt ggatccaagg ccgagacgta cctgcgggtc atgaagtgtc gccgcttcgt      60
ggaaagcagc tgtgccttca cctacaaaga gtttgagcgg gcgtacatcc ccagggaca     120 gaggtactcc atccagaacg cgcaggccgc cttctgcttc tcggagacca tcccggcccc    180
cacgggcaag gacgaggccc agcagcgatc cgacgtggag ctgctccgct tctccctgct    240
gctcatccag tcgtggctcg ggcccgtgca gtttctcagc agggtcttca ccaacagcct    300
ggtgttcggc acctcagacc gagtctacga gaagctcaag gacctggagg aaggcatcca    360
agccctgatg cgggagctgg aagatggcag tccccgggcc gggcagatcc tgaagcagac    420
ctacgacaag tttgacacga acctgcgcag tgacgatgcg ctgcttaaga actacgggct    480
gctctcctgc tt                                                        492

<210> SEQ ID NO 64
<211> LENGTH: 69
<212> TYPE: DNA
<213> ORGANISM: Artificial Sequence
<220> FEATURE:
<223> OTHER INFORMATION: Description of Artificial Sequence:  Primer

<400> SEQUENCE: 64
ggatccgaag gcacagctgc tttccacgaa gcggcgacac ttcatgaccc gcaggtacgt      60
ctcggcctt                                                             69
```

```
<210> SEQ ID NO 65
<211> LENGTH: 102
<212> TYPE: DNA
<213> ORGANISM: Artificial Sequence
<220> FEATURE:
<223> OTHER INFORMATION: Description of Artificial Sequence: Primer

<400> SEQUENCE: 65
agatcttcaa agccgcaccc ttgctccttg ctcttggttt ctctctccct gctgcctgct    60
catgatgtcc tggagcagct tgcgggcgga cagctggccc ag                      102

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 66
ccgcggcatc ctgagggtca a                                             21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 67
tatgcagatg ccatcttcaa c                                             21
```

GROWTH HORMONE AND GROWTH HORMONE RELEASING HORMONE COMPOSITIONS

CROSS-REFERENCE TO RELATED APPLICATIONS

This application is a continuation of U.S. Ser. No. 09/546,411, filed Apr. 12, 2000, now abandoned, which claims the benefit of priority of U.S. Ser. No. 60/128,830, filed Apr. 12, 1999.

INTRODUCTION

The present invention relates to novel variants of growth hormone releasing hormone (GHRH) that have enhanced resistance to enzymatic degradation and polynucleotides encoding said GHRH variants. The present invention relates to methods and therapeutic compositions for the treatment of growth hormone related deficiencies comprising administrating to humans, companion animals, livestock or poultry, plasmid compositions comprising polynudeotides encoding GHRH or variants thereof, alone or in combination with polynucleotides encoding growth hormone or modified growth hormone. The present invention further relates to methods and compositions that promote the release and expression of growth hormone in order to enhance the growth and performance of companion animals, livestock or poultry comprising the administration plasmid compositions encoding GHRH variants, GHRH or modified GHRH, and/or GH or modified GH.

BACKGROUND OF THE INVENTION

Growth hormone-releasing hormone ("GHRH") is a peptide hormone secreted from the hypothalamus. Following secretion, GHRH enters the portal circulation connecting the hypothalamus to pituitary gland. GHRH then interacts with its receptors on the pituitary gland and induces the release of growth hormone ("GH"). GH secreted from the pituitary gland enters the general circulation and from there it reaches various organs and tissues of the body where it interacts with specific receptors and induces a wide range of developmental effects.

GHRH peptides have been isolated and characterized from several species including humans, porcine, ovine and bovine. In each of these species, GHRH is a small polypeptide consisting of 44 amino acids (GHRH(1–44)-NH$_2$). However, it has been also shown that smaller fragments, most notably those consisting of the first (amino terminal) 29 amino acids (referred to as GHRH1–29 fragment) retain the same intrinsic biological activity as the full length parent molecule.

GHRH is synthesized as a precursor polypeptide consisting of 107 or 108 amino acids depending on the species. Following synthesis, the precursor GHRH polypeptide undergoes sequential processing. First, the 31 amino acid signal peptide (Met$^{-30}$ to Arg$^0$) of the GHRH precursor polypeptide is cleaved (Smith et al., 1992, *Biotechnology* 10:315–319). Subsequently, the GHRH precursor polypeptide is cleaved at position 46–47 and at position 45–46 by a trypsin-like endopeptidase and a carboxypeptidase, respectively, resulting in generation of GHRH(1–45)-OH and a 30 amino acid peptide (amino acids 77–107) designated GCTP (Brar, A. K. et al., 1991, *Endocrinology* 129: 3274–3280). The GHRH(1–45)-OH polypeptide is further processed by peptidyl glycine α-amidating monooxygenase ("PAM"), which transfers an amide group from Gly$^{45}$ to Leu$^{44}$ and results in the formation of GHRH(1–44)-NH$_2$, the full length form of GHRH (Brar, A.K. et al., 1991, *Endocrinology* 129: 3274–3280). The GCTP is also undergoes processing by PAM, which results in the transfer of an amide group from Gly$^{77}$ to Gln$^{76}$. Although the role of GHRH (1–44)-NH$_2$ in inducing the release of GH is well established, the role of the GCTP peptide is less clear. One report has implicated the GCTP peptide in the control of feeding behavior (Arase, K. et al., 1987, *Endocrinology* 121:1960–1965).

GH has been identified and its gene cloned from many species including human, porcine, bovine, and equine. Unlike GHRH, there exists natural variants of GH within a given species. For example, bovine GH is released from the pituitary gland in one of four variants which differ from one another by one or more amino acids and some studies suggest that these variants differ in their potency (e.g., in terms of their ability to increase milk yield). Several studies have also identified amino acid substitutions that lead to an increase in the affinity of GH to its receptors and/or enhanced stability to enzymatic degradation. Studies have also shown that immunization against specific peptides from GH (e.g., a peptide consisting of amino acids 35 to 53 of GH) leads to production of antibodies that bind growth hormone and increase the efficacy of GH treatment, presumably because the antibodies delay the clearance of GH from circulation, thus, increasing half-life of GH, and/or protect GH from proteolytic degradation (Bomford, F. and Aston, P., 1990, *Endocrnnology* 125:31–38).

Significant research efforts have focused on the structural attributes of GH and GHRH, as well as their biological and developmental activities. A number of groups have attempted to exploit GH and GHRH in a manner that could provide important therapeutic and economic benefits as a result of their use in humans and animals. For example, the traditional treatment of GH-deficient children has been the administration of growth hormone isolated from human pituitary glands, however these preparations are no longer available in the United States due to virus-contaminated samples (Vance, 1990, *Clin. Chem* 36/3: 415–420). Recombinantly expressed and purified GH have been shown to have some benefits in treating GH-deficient children, however the combination of recombinantly expressed GH and GHRH in the treatment of GH-deficient children has provided conflicting results. (Vance. supra). Further, purified GH and GHRH must be administered at very high quantities to be effective as the exposure of these polypeptides to serum results in their rapid degradation to a polypeptide which exhibits considerably different biological and pharmacokinetic properties. (Fronman et al., 1989, *J. Clin. Invest.* 83:1533–1540).

Other studies have shown that GH or GHRH administered as purified polypeptides have significant impact on animal growth (muscle and bone growth), average daily gain, milk production, feed efficiency (the ratio of feed consumed to body weight gain), adipose tissue accretion and others. For example, it has been shown that daily administration of maximally effective doses of GH administered to growing pigs for 33–77 days can increase average daily gain –10–20%, improves feed efficiency 13–33%, decrease adipose tissue accretion by as much as 70%, and stimulates protein deposition (muscle growth) by as much as 62%. (Etherton et al.,1998, *Physiological Reviews* 78:745–761). Furthermore, when GH was administered to dairy cows, milk yields were increased by 10–15% (□4–6kg/day) (Etherton et al.,1998, *Physiological Reviews* 78:745–761).

A major impediment to fulfilling the therapeutic and economic potential of GHRH peptides is their susceptibility to cleavage (and subsequent conversion to inactive forms) by specific tissue and plasma proteolytic enzymes; most notably dipeptidylpeplidase IV ("DPPIV"). A number of researchers have focused on manipulating GHRH in order to develop compounds with significant therapeutic potential. Consequently, a wide variety of synthetic GHRH peptide analogues have been produced. They consist of GHRH polypeptides in which one or more amino acids have been chemically modified or replaced with other L- or D-amino acids. These modifications or substitutions are designed to yield analogues with biological properties superior to those of the parent molecule in terms of potency, stability and resistance to chemical and enzymatic degradation. However, these chemically modified polypeptides are not easily or efficiently produced in a suitable form to be administered to humans or animals.

In spite of the significant therapeutic and economic benefits of GH or GHRH alluded to above, exogenous supplementation of animals with GH or GHRH proteins have not been widely adopted as a component of routine management practices to enhance the quality of meat from animals and/or enhance the productivity of livestock. This is because in order to get these benefits, animals have to be repeatedly administered GH or GHRH polypeptides (often daily, but typically in a slow release formulation given every 7–10 days). (Etherton, T. D., 1997, *Nature Biotechnology* 15:1248) This situation is labor intensive, time consuming, expensive, and does not fit current management practices where animals are reared in large numbers and are handled very infrequently, it is apparent therefore that in order to realize the therapeutic and economic benefits of GH and/or GHRH administration, much improved formulations for delivery of these hormones must be developed to overcome the current limitations of their use; namely the need for repeated administration.

SUMMARY OF THE INVENTION

The present invention relates to novel variants of GHRH that have enhanced resistance to enzymatic degradation and polynucleotides encoding said variants. The present invention also relates to pharmaceutical formulations comprising polynucleotide sequences encoding GHRH variants alone or in combination with polynucleotide sequences encoding GHRH, modified GHRH, GH and/or modified GH. The present invention also relates to pharmaceutical formulations comprising GHRH variant peptides alone or in combination with GHRH polypeptides, modified GHRH polypeptides, GH polypeptides and/or modified GH polypeptides. The present invention further relates to pharmaceutical formulations comprising canine or feline GHRH peptides alone or in combination with GHRH variant polypeptides, modified GHRH polypeptides, GH polypeptides and/or modified GH polypeptides.

The present invention relates to therapeutic methods and compositions for the treatment of growth hormone related deficiencies comprising growth hormone ("GH") and/or growth hormone-releasing hormone ("GHRH") in human, companion animals, livestock and poultry. The invention also relates to methods for the improvement in the health of humans, companion animals, livestock and poultry. The invention also relates to methods for the treatment of obesity and frailty of companion animals. The invention further relates to methods for the enhancement of the growth and performance of companion livestock and poultry. The methods of the present invention comprise pharmaceutical compositions which enhance the expression of growth hormone or promote the release of growth hormone or both when administered to humans, companion animals, livestock or poultry. According to the present invention, the term "GHRH" relates to the full length wildtype form of GHRH which is 44 amino acids (aa) or a precursor form of GHRH. In accordance with the present invention, the term "modified GHRH" refers to any amino terminal polypeptide fragment of GHRH from 29 amino acids to 107 or 108 amino acids in length and any mutant of GHRH, including additions, deletions or substitutions at the nudeotide or amino acid level, which retains at least the level of activity of wildtype GHRH, that is, the ability to induce GH gene transcription at levels comparable to wildtype GHRH.

In accordance with the present invention, the term "GHRH variant" relates to a GHRH polypeptide to which one or more amino acids have been attached to the carboxy or amino terminus of the polypeptide, or a wildtype GHRH polypeptide that contains a substitution of one or more amino acids, so that the GHRH variant retains at least equal or enhanced wildtype GHRH activity and has enhanced resistance to enzymatic degradation relative to the wildtype GHRH. In accordance with the present invention, wildtype GHRH activity is measured by its ability to induce GH gene transcription. In accordance with the present invention, resistance to enzymatic degradation is determined by the ability of the polypeptide to resist degradation caused by dipeptidylpeptidase type IV.

According to the present invention, the term "GH" refers to the full length wildtype form of GH, which is 191 amino acids, and "modified GH" refers to any fragment of GH and any mutant including additions, deletions or substitutions at the nucleotide or amino acid level, which retains at least the level of wildtype activity of GH, that is, the ability to induce insulin growth factor (IGF) gene transcription at levels comparable to wildtype GH, or mimic the anti-adipogenic and lipolytic effects of GH.

DETAILED DESCRIPTION OF THE INVENTION

Figure 1:
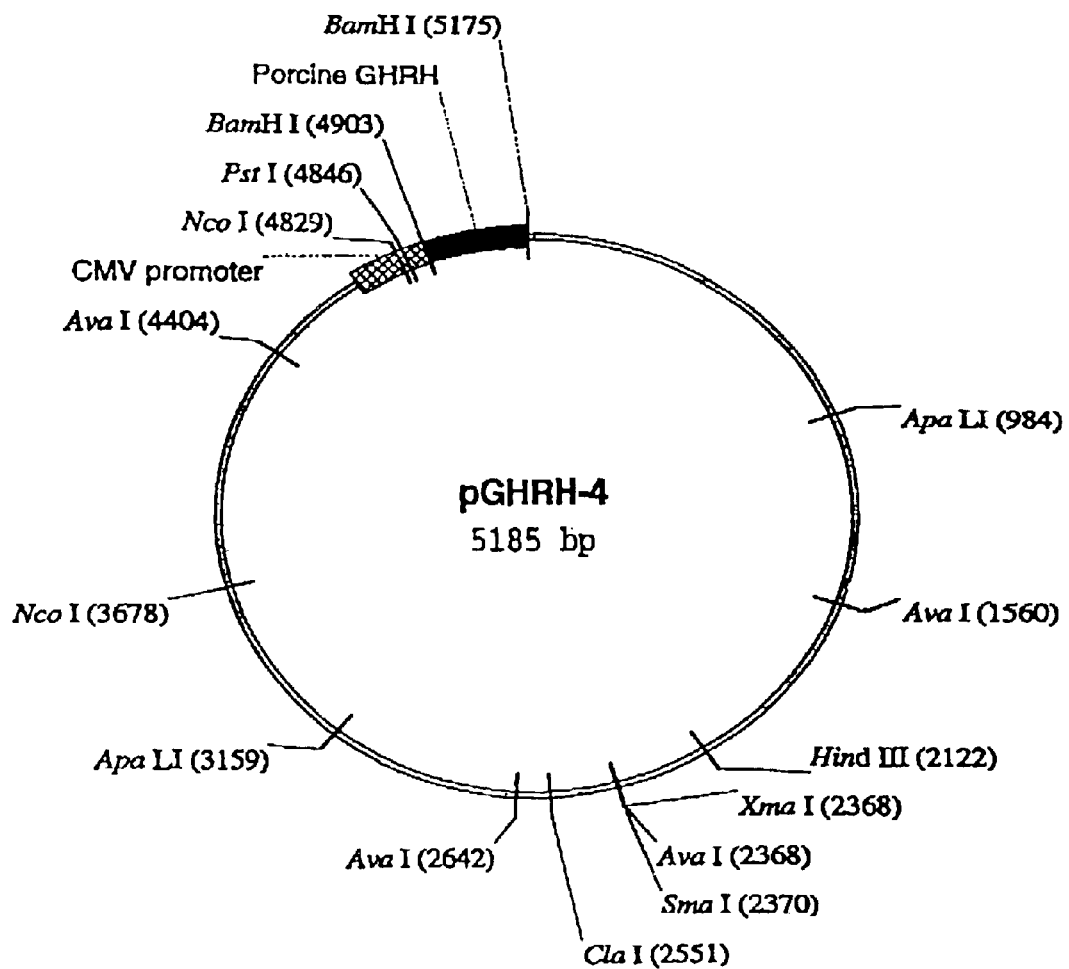
FIG. 1 is a map of the pGHRH-4 construct (SEQ ID No. 47).

The present invention relates to novel variants of GHRH that have enhanced resistance to enzymatic degradation and polynudeotides encoding said GHRH variants. The present invention relates to pharmaceutical compositions which promote the release and/or expression of GH. In particular, the pharmaceutical compositions of the present invention comprise polynucleotide sequences encoding GHRH variants alone or in combination with polynucleotide sequences encoding GHRH, modified GHRH, GH and/or modified GH or any combination thereof. In another embodiment, the pharmaceutical compositions of the present invention comprise GHRH variant polypeptides alone or in combination with GHRH polypeptides, GHRH modified polypeptides, GH polypeptides or GH modified polypeptides or any combination thereof.

The present invention relates to methods of treating disorders related to GH related deficiencies in humans, companion animals, livestock and poultry, comprising administering pharmaceutical formulations which enhance GH expression and/or release. The present invention further relates to methods of treating livestock and poultry in order to enhance growth and performance comprising administering pharmaceutical formulations which enhance GH expression and/or release.

The pharmaceutical formulations to be administered in accordance with the methods of the, present invention encompass plasmid compositions comprising (a) polynucleotide sequences encoding GHRH variants; (b) polynucleotide sequences encoding GHRH or modified GHRH; (c) polynucleotide sequences encoding GH or modified GH; or any combination thereof, wherein the polynucleotide sequences are operably linked to a promoter or regulatory element, preferably one that is transcriptionally active in muscle tissue. The pharmaceutical formulations to be administered in accordance with the methods of the present invention also include: i) plasmid compositions comprising polynucleotides encoding for GH or modified or variant GHRH gene; ii) plasmid compositions comprising polynucleotides encoding for both GH and GHRH genes; iii) plasmid compositions comprising polynucleotides encoding for a GHRH gene, a GH gene or a gene encoding a fusion protein consisting of a peptide from GH and a carrier protein for induction of GH potency-enhancing antibodies; (iv) recombinant proteins, peptides, fragments or derivatives thereof comprising canine GHRH or feline GHRH; (v) recombinant proteins, peptides, fragments or derivatives thereof of the GHRH variants of the present invention; and (vi) recombinant fusion proteins, peptides, fragments or derivatives thereof comprising GH and GHRH.

In one embodiment, the pharmaceutical compositions of the present invention comprise polynucleotide sequences encoding canine or feline GHRH alone or in combination with polynucleotide sequences encoding GHRH variant, modified GHRH, GH and/or modified GH or any combination thereof. In another embodiment, the pharmaceutical compositions of the present Invention comprise canine or feline GHRH polypeptides alone or in combination with GHRH variant polypeptides, modified GHRH, GH polypeptides or GH modified polypeptides or any combination thereof. The pharmaceutical compositions of the present invention are in suitable formulation to be administered to humans, companion animals, livestock or poultry for the treatment of growth hormone related deficiencies or the enhancement of growth and performance of livestock and poultry. The pharmaceutical compositions of the present invention are also in suitable formulation for the treatment of obesity and frailty of companion animals or the improvement in the health of humans, companion animals, livestock, and poultry.

The present invention relates to therapeutic methods and compositions for the treatment of growth hormone related deficiencies comprising growth hormone ("GH"); modified GH; growth hormone releasing hormone ("GHRH"); GHRH variants; modified GHRH or any combination thereof. The therapeutic compositions of the invention are administered to animals, preferably to mammals, more preferably to companion animals (e.g., dogs, cats and horses), livestock (e.g., cows and pigs) and poultry (e.g., chickens and turkeys), and most preferably to humans. The invention also relates to methods and compositions for the enhancement of the growth and performance of animals, more preferably mammals, and most preferably livestock (e.g., cows and pigs) and poultry (e.g., chickens and turkeys) with the proviso that such compositions are not to be administered to mice, rats, rodents, guinea pigs, or rabbits. The invention also relates to methods and compositions for the treatment of obesity and frailty of animals, preferably to mammals, more preferably to companion animals (e.g., dogs, cats and horses). The invention further relates to methods and compositions for the improvement in the health of animals, preferably to mammals, more preferably to companion animals (e.g., dogs, cats and horses), livestock (e.g., cows and pigs) and poultry (e.g., chickens and turkeys), and most preferably to humans.

The present invention is based in part of the discovery of recombinantly engineered GHRH variants which retain at least the level of activity wildtype GHRH, that is the ability to induce GH gene transcription at levels comparable to wildtype GHRH, and which have enhanced resistance to enzymatic degradation relative to the wildtype GHRH. The GHRH variants of the present invention may be recombinantly expressed at high levels in host cells and easily isolated and purified in a form suitable for administration to humans and animals. Thus, the GHRH variants of the present invention may be efficiently produced and isolated at high levels as opposed to modified GHRH polypeptides in the art which are modified using traditional chemistry methods to introduce modifications in the native GHRH sequence.

In one embodiment, a GHRH variant of the present invention comprises the addition of one amino acid, preferably a hydrophobic residue and more preferably a tyrosine residue, to the amino terminus (position 1) of GHRH. In another embodiment, a GHRH variant comprises the addition of two amino acids, wherein the second amino acid is not proline or alanine, to the amino terminus (position 1) of GHRH. In another embodiment, a GHRH variant comprises the addition of three amino acids, wherein the second amino acid is proline or alanine, to the amino terminus (position 1) of GHRH. In another embodiment, a GHRH variant comprises the addition of more than three amino acids to the amino terminus (position 1) of GHRH, wherein the addition does not interfere with the functional activity of GHRH, that is, the ability of GHRH to induce GH gene transcription. In a preferred embodiment of the present invention, a GHRH variant comprises the addition of a tripeptide to the amino terminus, wherein the tripeptide is diprotin A or diprotin B or a peptide with a structure analogous to diprotin A or diprotin B. In yet another embodiment, a GHRH variant comprises the addition of glycine and arginine at the carboxy-terminus. This addition results in the amidation of GHRH; the glycine and arginine is cleaved off and the last amino acid before the added glycine is amidated.

In one embodiment, a GHRH variant comprises any of the amino acid additions described above and the substitution of glycine with alanine at residue 15. In another embodiment, a GHRH variant comprises any of the amino acid additions described above and the substitution of leucine with alanine at residue 22. In another embodiment, a GHRH variant comprises any of the amino acid additions described above and the substitutions of glycine with alanine at residue 15 and leucine with alanine at residue 22. In another embodiment, a GHRH variant comprises any of the amino acid additions at the amino terminus and the amino acid additions at the carboxy-terminus. In another embodiment, a GHRH variant comprises any of the amino acid additions at the amino terminus described above, the amino acid additions at the carboxy-terminus described above, and the substitution of glycine to alanine at residue 15. In another embodiment, a GHRH variant comprises any of the amino acid additions at the amino terminus described above, the amino acid additions at the carboxy-terminus described above, and the substitution of leucine to alanine at residue 22. In yet another embodiment, a GHRH variant comprises any of the amino acid additions at the amino terminus described above, the amino acid additions at the carboxy-terminus described above, and the substitutions of glycine to alanine at residue 15 and leucine to alanine at residue 22. The term "GHRH precursor variant" as used herein refers to a precursor form of the full length wildtype GHRH polypeptide to which one or more amino acids have been attached to the amino terminus of the polypeptide and/or contains a substitution of one or more amino acids, so that the GHRH precursor variant retains at least equal or enhanced wildtype GHRH activity and has enhanced resistance to enzymatic degradation relative to wildtype GHRH. In one embodiment of the present invention, a GHRH precursor variant comprises the amino acid additions and/or the amino acid substitutions described above. The present invention also encompasses a fusion variant comprising any of the GHRH variants described above and GH or modified GH. The term "fusion variant" as used herein refers to a fusion protein comprising GHRH variants or modified GHRH and GH or modified GH. In one embodiment of the present invention, a fusion variant comprises any of the GHRH variants described above, which consist of amino acid additions at the amino terminus and/or amino acid substitutions, and GH or modified GH.

The modifications and/or substitutions of GHRH described herein are made to GHRH polypeptides which retain the biological activity at least equal to the full length wildtype GHRH, preferably a precursor form of GHRH, more preferably the sequence of GHRH consisting of about 29 amino acids to about 44 amino acids. The polynucleotide sequences encoding the GHRH variants described herein are also within the scope of the present invention. The present invention provides that the polypeptides are encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins. The present invention encompasses GHRH variants encoded by the polynucleotide sequence any species.

The present invention encompasses polynucleotide sequences encoding precursor forms of GHRH, full length wildtype GHRH, modified GHRH, GHRH variants, and fragments of GHRH from 29 amino acids to 44 amino acids in length for any species, which retain at least the activity of wildtype GHRH. For example, the polynucleotide sequences encoding human, swine, and bovine growth hormone releasing hormone disclosed in Genbank accession number SEG HSGHRH, accession number U90275, and accession number U29611, respectively, are incorporated herein by reference. The present invention also encompasses polynucleotide sequences encoding GHRH polypeptides disclosed for any species (e.g., the polynucleotide sequence encoding the human GHRH precursor polypeptide disclosed in Genbank accession number P01286 is incorporated herein by reference). The present invention further encompasses polynucleotide sequences encoding full length wildtype GH or modified GH for any species. For example, the polynucleotide sequences encoding human, swine, and bovine growth hormone disclosed in Genbank accession number J03071, accession number U19787, and accession number E00293, respectively, are incorporated herein by reference. The present invention also encompasses polynucleotide sequences encoding GH polypeptides disclosed for any species (e.g., the polynucleotide sequence encoding the bovine GH polypeptide disclosed in Genbank accession number STBO is incorporated herein by reference).

The polynucleotide sequence encoding GHRH, modified GHRH or GHRH variants can be inserted into an appropriate expression vector, i.e., a vector which contains the necessary elements for the transcription and translation of the inserted protein-coding sequence. The polynucleotide sequence encoding GH or modified GH can be inserted into an appropriate expression vector, i.e., a vector which contains the necessary elements for the transcription and translation of the inserted protein coding sequence. The necessary transcriptional and translational signals can also be supplied by the native GH or native GHRH genes or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In one embodiment, the wildtype or modified human GH gene is expressed. In another embodiment, the wildtype, modified or variant human GHRH is expressed. In yet another embodiment, the wildtype or modified human GH and the wildtype, modified or variant human GHRH gene are expressed.

Any of the methods previously described for the insertion of DNA fragments into a vector may be used to construct expression vectors containing a chimeric gene, comprising GH or modified GH and GHRH, modified GHRH or GHRH variants, consisting of appropriate transcriptional and translational control signals and the protein coding sequences. These methods may include in vitro recombinant DNA and synthetic techniques and in vivo recombinants (genetic recombination). Expression of the nucleic acid sequence encoding GH or modified GH may be regulated by a second nucleic acid sequence so that the GH or modified GH is expressed in a host transformed with the recombinant DNA molecule. Expression of the nucleic acid sequence encoding GHRH, modified GHRH or GHRH variant may be regulated by a second nucleic acid sequence so that the GHRH modified GHRH or GHRH variant is expressed in a host transformed with the recombinant DNA molecule. For example, expression of GH or GHRH may be controlled by any promoter or enhancer element known in the art. Promoters which may be used to control GH and/or GHRH gene expression include, but are not limited to, the Cytomeglovirus (CMV) immediate early promoter region, the SV40 early promoter region (Bernoist and Chambon, 1981, *Nature* 290:304–310), the promoter contained in the 3' long terminal repeat of Rous sarcoma virus (Yamamoto, et al., 1980, *Cell* 22:787–797), the herpes thymidine kinase promoter (Wagner et al., 1981, *Proc. Natl. Acad. Sci. USA* 78:1441–1445), the regulatory sequences of the metallothionein gene (Brinster et al., 1982, *Nature* 296:39–42); prokaryotic expression vectors such as the β-lactamase promoter (Villa-Kamaroff et al., 1978, *Proc. Natl. Acad. Sci. USA* 75:3727–3731), or the tac promoter (DeBoer et al., 1983, *Proc. Natl. Aced. Sci. USA* 80:21–25); see also "Useful proteins from recombinant bacteria" in *Scientific American*, 1980, 242:74–94; plant expression vectors comprising the nopaline synthetase promoter region (Herrera-Estrella et al., *Nature* 303:209–213) or the cauliflower mosaic virus 35S RNA promoter (Gardner et al., 1981, *Nucl. Acids Res.* 9:2871), and the promoter of the photosynthetic enzyme ribulose biphosphate carboxylase (Herrera-Estrella et al., 1984, *Nature* 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, *Cell* 38:639–646; Omitz et al., 1986, *Cold Spring Harbor Symp. Quant. Biol.* 50:399–409; MacDonald, 1987, *Hepatology* 7:425–515); Insulin gene control region which is active in pancreatic beta cells (Hanahan, 1985, *Nature* 315:115–122), immunoglobulin gene control region which is active in lymphoid cells (Grosschedl et al., 1984, *Cell* 38:647–658; Adames et al., 1985, *Nature* 318:533–538; Alexander et al., 1987, *Mol. Cell. Biol.* 7:1436–1444), mouse mammary tumor virus control region which is active in testicular, breast, lymphoid and mast cells (Leder et al., 1986, *Cell* 45:485–495), albumin gene control region which is active in liver (Pinkert et al., 1987, *Genes and Devel.* 1:268–276), alpha-fetoproteln gene control region which is active in liver (Krumlauf et al., 1985, *Mol. Cell. Biol.* 5:1639–1648; Hammer et al., 1987, *Science* 235:53–58; alpha 1-antitrypsin gene control region which is active in the liver (Kelsey et al., 1987, *Genes and Devel.* 1:161–171), beta-globin gene control region which is active in myeloid cells (Mogram et al., 1985, *Nature* 315:338–340; Kollias et al., 1986, *Cell* 46:89–94; myelin basic protein gene control region which is active in oligodendrocyte cells in the brain (Readhead et al., 1987, *Cell* 48:703–712); myosin light chain-2 gene control region which is active in skeletal muscle (Sani, 1985, *Nature* 314:283–286), swine alpha-skeletal actin control region which is active in muscle (Reecy, M. et al., 1998, *Animal Biotechnology* 9:101–120) and gonadotropic releasing hormone gene control region which is active in the hypothalamus (Mason et al., 1986, *Science* 234:1372–1378).

In a specific embodiment, a vector is used that comprises a promoter operably linked to GH- or modified GH-encoding nucleic acid, one or more origins of replication, and, optionally, one or more selectable markers (e.g., an antibiotic resistance gene). In another embodiment, a vector is used that comprises a promoter operably linked to GHRH-, modified GHRH- or GHRH variant-encoding nucleic acid, one or more origins of replication, and, optionally, one or more selectable markers (e.g., an antibiotic resistance gene). In yet another embodiment, a vector is used that comprises a promoter operably linked to GH or modified GH and GHRH, modified GHRH or GHRH variant-encoding nucleic acids, one or more origins of replication, and, optionally, one or more selectable markers (e.g., an antibiotic resistance gene).

Expression vectors containing gene inserts can be identified by three general approaches: (a) nucleic acid hybridization, (b) presence or absence of "marker" gene functions, and (c) expression of Inserted sequences. In the first approach, the presence of the GH- or modified GH-encoding polynucleotides and GHRH-, modified GHRH- or GHRH variant-encoding polynucleotides inserted in an expression vector(s) can be detected by nucleic acid hybridization using probes comprising sequences that are homologous to the inserted genes. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of the gene(s) in the vector(s). For example, if the GH gene is inserted within the marker gene sequence of the vector, recombinants containing the GH gene insert can be identified by the absence of the marker gene function. In the third approach, recombinant expression vectors can be identified by assaying the gene product expressed by the recombinant. Such assays can be based, for example, on the physical or functional properties of the GH and GHRH in in vitro assay systems, e.g., binding of GH with anti-GH antibody or binding of GHRH with anti-GHRH antibody.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

For long-term, high-yield production of recombinant proteins, stable expression is preferred. For example, cell lines which stably express the differentially expressed or pathway gene protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the differentially expressed or pathway gene protein. Such engineered cell lines may be particularly useful in screening and evaluation of compounds that affect the endogenous activity of the differentially expressed or pathway gene protein.

A number of selection systems may be used, including but not limited to the herpes simplex virus thymidine kinase (Wigler, et al., 1977, *Cell* 11:223), hypoxanthine-guanine phosphoribosyltransferase (Szybalska & Szybalski, 1962, *Proc. Natl. Aced. Sci. USA* 48:2026), and adenine phosphoribosyhtransferase (Lowy et al., 1980, *Cell* 22:817) genes can be employed in tk$^{31}$, hgprt⁻ or aprt⁻ cells, respectively. Also, antimetabolite resistance can be used as the basis of selection for dhfr, which confers resistance to methotrexate (Wigler et al., 1980, *Natl. Acad. Sci. USA* 77:3567; O'Hare et al., 1981, *Proc. Natl. Acad. Sci. USA* 78:1527); gpt, which confers resistance to mycophenolic acid (Mulligan & Berg, 1981, *Proc. Nail. Acad. Sci. USA* 78:2072); neo, which confers resistance to the aminoglycoside G-418 (Colberre-Garapin et al., 1981, *J. Mol. Biol.* 150:1); and hygro, which confers resistance to hygromycin (Santerre et al., 1984, *Gene* 30:147) genes.

The present invention provides for the treatment or prevention of GH associated diseases or disorders, including those disorders characterized by GH deficiency, comprising the administration of a pharmaceutical formulation to a human, companion animal, livestock or poultry which enhances GH expression and/or release. The present invention also provides for methods and protocols to enhance the growth and performance of livestock and poultry, comprising the administration of a pharmaceutical formulation to a companion animal, livestock or poultry which enhances GH expression and/or release. The present invention also provides for the treatment of obesity and frailty, comprising the administration of a pharmaceutical formulation to a companion animal which enhances or modulates GH expression and/or release. The present invention further provides for methods for the improvement in health, comprising the administration of a pharmaceutical formulation to a human, companion animal, livestock or poultry which enhances GH expression and/or release. In accordance with the invention, methods of the present invention encompass the administration of pharmaceutical formulations comprising: (a) polynucleotide sequences encoding GHRH variants alone or in combination with polynucleotide sequences encoding GHRH, modified GHRH, GH, modified GH or any combination thereof, wherein the polynucleotide sequences are operably linked to a promoter or regulatory element, preferably one that is transcriptionally active in muscle tissue; (b) polynucleotide sequences encoding canine or feline GHRH alone or in combination with polynucleotide sequences encoding GHRH variants, modified GHRH, GH, modified GH or any combination thereof, wherein the polynucleotide sequences are operably linked to a promoter or regulatory element, preferably one that is transcriptionally active in muscle tissue; (c) polynucleotide sequences encoding GHRH, modified GHRH, GH, modified GH or any combination thereof wherein the polynucleotide sequences are operably linked to a promoter or regulatory element, preferably one that is transcriptionally active in muscle tissue; (c) variant GHRH polypeptides alone, expressed as a fusion protein, or in combination with GHRH, modified GHRH, GH or modified GH polypeptides or any combination thereof; or (d) canine or feline GHRH polypeptides alone, expressed as a fusion protein, or in combination with GHRH variants, modified GHRH, GH or modified GH polypeptides or any combination thereof.

Generally, administration of products of a species origin or species reactivity (in the case of antibodies) that is the same species as that of the patient is preferred. Thus, in a preferred embodiment, human GH and/or GHRH genes, gene fragments or derivatives thereof are administered to a human patient for therapy or prophylaxis.

In a specific embodiment, nucleic acids comprising sequences encoding GH and/or GHRH or functional derivatives thereof, are administered to promote the release and/or elevation of growth hormone, by way of gene therapy. Gene therapy refers to therapy performed by the administration to a subject of an expressed or expressible nucleic acid. In this embodiment of the invention, the nucleic acids produce their encoded protein that mediate a therapeutic effect by promoting the function of GH.

Any of the methods for gene therapy available in the art can be used according to the present invention. Exemplary methods are described below.

For general reviews of the methods of gene therapy, see Goldspiel et al., 1993, *Clinical Pharmacy* 12:488–505; Wu and Wu, 1991, *Biotherapy* 3:87–95; Tolstoshev, 1993, *Ann. Rev. Pharmacol. Toxicol.* 32:573–596; Mulligan, 1993, *Science* 260:926–932; and Morgan and Anderson, 1993, *Ann. Rev. Biochem.* 62:191–217; May, 1993, *TIBTECH* 11(5): 155–215). Methods commonly known in the art of recombinant DNA technology which can be used are described in Ausubel et al. (eds.), 1993, Current Protocols in Molecular Biology, John Wiley & Sons, NY; and Kriegler, 1990. Gene Transfer and Expression, A Laboratory Manual, Stockton Press, NY.

In a preferred aspect, the compound comprises nucleic acid sequences encoding GH or modified GH and GHRH, modified GHRH or GHRH variants, said nucleic acid sequences being part of expression vectors that express GH or modified GH and GHRH, modified GHRH or GHRH variants in a suitable host. In particular, such nucleic acid sequences have promoters operably linked to the GH or modified GH and GHRH, modified GHRH or GHRH variants coding regions, said promoters being inducible or constitutive, and, optionally, tissue-specific. In another particular embodiment, nucleic acid molecules are used in which the GH or modified GH and GHRH, modified GHRH or GHRH variants coding sequences and any other desired sequences are flanked by regions that promote homologous recombination at a desired site in the genome, thus providing for intrachromosomal expression of the GH or modified GH and GHRH, modified GHRH or GHRH variants nucleic acids (Koller and Smithies, 1989, *Proc. Natl. Acad. Sci. USA* 86:8932–8935; Zijlstra et al., 1989, *Nature* 342:435–438).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic add sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, *J. Biol.*

Chem. 262:4429–4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO 92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, *Proc. Natl. Acad. Sci. USA* 86:8932–8935; Zijlstra et al., 1989, *Nature* 342:435–438).

In a specific embodiment, viral vectors that contain nucleic acid sequences encoding GH or modified GH and/or GHRH, modified GHRH or GHRH variants are used. For example, a retroviral vector can be used (see Miller et al., 1993, *Meth. Enzymol.* 217:581–599). These retroviral vectors have been to delete retroviral sequences that are not necessary for packaging of the viral genome and integration into host cell DNA. The nucleic acid sequences encoding the GH or modified GH and GHRH, modified GHRH or GHRH variants to be used in gene therapy are cloned into one or more vectors, which facilitates delivery of the gene into a patient. More detail about retroviral vectors can be found in Boesen et al., 1994, *Biotherapy* 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, *J. Clin. Invest.* 93:644–651; Kiem et al., 1994, *Blood* 83:1467–1473; Salmons and Gunzberg, 1993, *Human Gene Therapy* 4:129–141; and Grossman and Wilson, 1993, *Curr. Opin. in Genetics and Devel.* 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, *Current Opinion in Genetics and Development* 3:499–503 present a review of adenovirus-based gene therapy. Bout et al., 1994, *Human Gene Therapy* 5:3–10 demonstrated the use of adenovirus vectors to transfer genes to the respiratory epithelia of rhesus monkeys. Other instances of the use of adenoviruses in gene therapy can be found in Rosenfeld et al., 1991, *Science* 252:431–434; Rosenfeld et al., 1992, *Cell* 68:143–155; Mastrangeli et al., 1993, *J. Clin. Invest.* 91:225–234; PCT Publication WO94/12649; and Wang, et al., 1995, *Gene Therapy* 2:775–783. In a preferred embodiment, adenovirus vectors are used. Adeno-associated virus (AAV) has also been proposed for use in gene therapy (Walsh et al., 1993, *Proc. Soc. Exp. Biol. Med.* 204:289–300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, *Meth. Enzymol.* 217:599–618; Cohen et al., 1993, *Meth. Enzymol.* 217:618–644; Cline, 1985, *Pharmac. Ther.* 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, subject=s state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the subject.

In an embodiment in which recombinant cells are used in gene therapy, nucleic acid sequences encoding GH or modified GH and/or GHRH, modified GHRH or GHRH variants are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598, dated Apr. 28, 1994; Stemple and Anderson, 1992, *Cell* 71:973–985; Rheinwald, 1980, *Meth. Cell Bio.* 21A:229; and Pittelkow and Scott, 1986, *Mayo Clinic Proc.* 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

The polypeptides of the invention include polypeptides which comprise the amino acid sequence of canine or feline GHRH. The polypeptides of the invention also include polypeptides which comprise the amino acid sequence of a GHRH variant of the present invention. The polypeptides of the invention further include polypeptides which comprise the amino acid sequence of GH or modified and GHRH or modified GHRH. Protein compositions of the present invention may further comprise an acceptable carrier, such as a hydrophilic, e.g., pharmaceutically acceptable, carrier.

The invention also relates to methods for producing a polypeptide comprising growing a culture of the cells of the invention in a suitable culture medium, and purifying the protein from the culture. For example, the methods of the invention include a process for producing a polypeptide in which a host cell containing a suitable expression vector that includes a polynucleotide of the invention is cultured under conditions that allow expression of the encoded polypeptide. The polypeptide can be recovered from the culture, conveniently from the culture medium, and further purified.

The present invention further provides isolated polypeptides encoded by the nucleic acid fragments of the present invention or by degenerate variants of the nucleic acid fragments of the present invention. By "degenerate variant is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins. A variety of methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides. Fragments are useful, for example, in generating antibodies against the native polypeptide. In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, *Protein Purification: Principles and Practice*, Springer-Verlag (1994); Sambrook, et al., in *Molecular Cloning: A Laboratory Manual*; Ausubel et al., *Current Protocols in Molecular Biology*.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention. The purified polypeptides can be used in in vitro binding assays which are well known in the art to identify molecules which bind to the polypeptides. These molecules include but are not limited to, for e.g., small molecules, molecules from combinatorial libraries, antibodies or other proteins.

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBat.RTM. kit), and such methods are well known in the art, as described in Summers and Smith, Texas Agricultural Experiment Station Bulletin No. 1555 (1987). incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl.RTM. or Cibacrom blue 3GA Sepharose.RTM.; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and in Vitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purity the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The compounds of the invention are preferably tested in vitro, and then in vivo for the desired therapeutic or prophylactic activity, prior to use in humans. For example, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

The expression of GH or modified GH and GHRH, modified GHRH or GHRH variants can be assayed by the immunoassays, gel electrophoresis followed by visualization, or any other method known to those skilled in the art.

In various specific embodiments, in vitro assays can be carried out with representative cells of cell types involved in a patient's disorder, to determine if a compound has a desired effect upon such cell types. In accordance with the present invention, the functional activity of GHRH can be measured by its ability to induce GH gene transcription in vitro. In accordance with the present invention, the functional activity of GHRH can be measured by its ability to induce IGF gene transcription in vitro.

Compounds for use in therapy can be tested in suitable animal model systems prior to testing in humans, including but not limited to pigs, chicken, cows or monkeys.

The invention provides methods of treatment (and prophylaxis) by administration to a subject of an effective amount of a compound of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human. In a specific embodiment, a non-human mammal is the subject.

Formulations and methods of administration that can be employed when the compound comprises a nucleic acid are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, 1987, *J. Biol. Chem.* 262:4429–4432), construction of a nucleic acid as part of a retroviral or other vector, etc. Methods of introduction include but are not limited to intratumoral, intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the compound can be delivered in a vesicle, in particular a liposome (see Langer, *Science* 249:1527–1533 (1990); Treat et al., in Liposomes in the Therapy of Infectious Disease and Cancer, Lopez-Berestein and Fidler (ads.), Liss, New York, pp. 353–365 (1989); Lopez-Berestein, ibid., pp. 317–327; see generally ibid.)

In yet another embodiment, the compound can be delivered in a controlled release system. In one embodiment, a pump may be used (see Langer, supra; Sefton, CRC Crt. *Ref Biomed. Eng.* 14:201 (1987); Buchwald et al., *Surery* 88:507 (1980); Saudek et al., *N. Engl. J. Med.* 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, *J. Macromol. Sci Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, ie., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (*Science* 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, *Proc. Natl. Acad. Sci. USA* 88:1864–1868), etc. Aternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particulariy for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can indude standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachefte indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of cancer can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

EXAMPLES

Cloning of Canine and Feline GHRH

1. Cloning of Canine GHRH

In order to clone the canine GHRH, the canine genomic library (Clonetech Lab) is screened with the radioactively labeled fragment encoding the porcine GHRH (SEQ ID No. 1) following protocols known to one of ordinary skill in the art. The fragment encoding the porcine GHRH (SEQ ID No. 1) is labeled using commercially available DNA labeling kits as recommended by the manufacturer. Clones identified that contain the gene coding for the canine precursor GHRH are isolated and sequenced by methods known to one of ordinary skill in the art. The sequence results obtained from sequencing both DNA strands of a done is compared with sequences of known GHRH species and the canine GHRH is subcloned into appropriate plasmid vectors (e.g., pVR1012; Vical, San Diego, Calif.) according to protocols known to one of ordinary skill in the art.

2. Cloning of Feline GHRH

In order to clone the feline GHRH, the feline genomic library (Clonetech Lab) is screened with the radioactively labeled fragment encoding the porcine GHRH (SEQ ID No. 1) following protocols known to one of ordinary skill in the art. The fragment encoding the porcine GHRH (SEQ ID No. 1) is labeled using commercially available DNA labeling kits as recommended by the manufacturer. Clones identified that contain the gene coding for the feline precursor GHRH are isolated and sequenced by methods known to one of ordinary skill in the art. The sequence results obtained from sequencing both DNA strands of a clone is compared with sequences of known GHRH species and the feline GHRH is subcloned into appropriate plasmid vectors (e.g., pVR1012; Vical, San Diego, Calif.) according to protocols known to one of ordinary skill in the art.

Synthesis of GHRH Constructs 3. pGHRH-4 (pGHRH1–44WTCMV)

In order to construct a plasmid containing the gene that codes for the natural porcine GHRH polypeptide and to have the latter secreted into the blood circulation when such plasmids are injected into animals, primers designated GHRH-1 (SEQ ID No. 61), GHRH-2 (SEQ ID No. 62), GHRH-4 (SEQ ID No. 66), and GHRH-7 (SEQ ID No. 67) were synthesized. The primers were used in reverse transcription polymerase chain reactions (RT-PCRs) to amplify the human GHRH signal sequence from human mRNA and the porcine GHRH protein sequence from porcine mRNA. The resulting PCR-amplified human GHRH signal sequence and porcine GHRH protein sequence were digested with Bgl II and Bam HI, respectively. Then the fragments were ligated together and cloned into the Bam HI site of the plasmid pVR1012 (Vical, San Diego, Calif.) to produce a plasmid designated pGHRH-4 (FIG. 1). The expression of the GHRH oligonucleotide (SEQ ID Nos. 1 and 2), which encodes a 75 amino acid polypeptide comprising the porcine GHRH protein sequence (44 amino acids) preceded by the signal sequence from human GHRH protein (31 amino acids), is driven by Cytomegalo-virus immediate early (CMV IE) promoter/enhancer element.

4. pGHRH1–4WTSK685:

A plasmid containing the polynucleotide sequences encoding the 75-amino acid GHRH protein described above driven by a 685 bp fragment derived from the swine α-skeletal actin promoter (SEQ ID No. 3) was constructed as described below.

Figure 2:
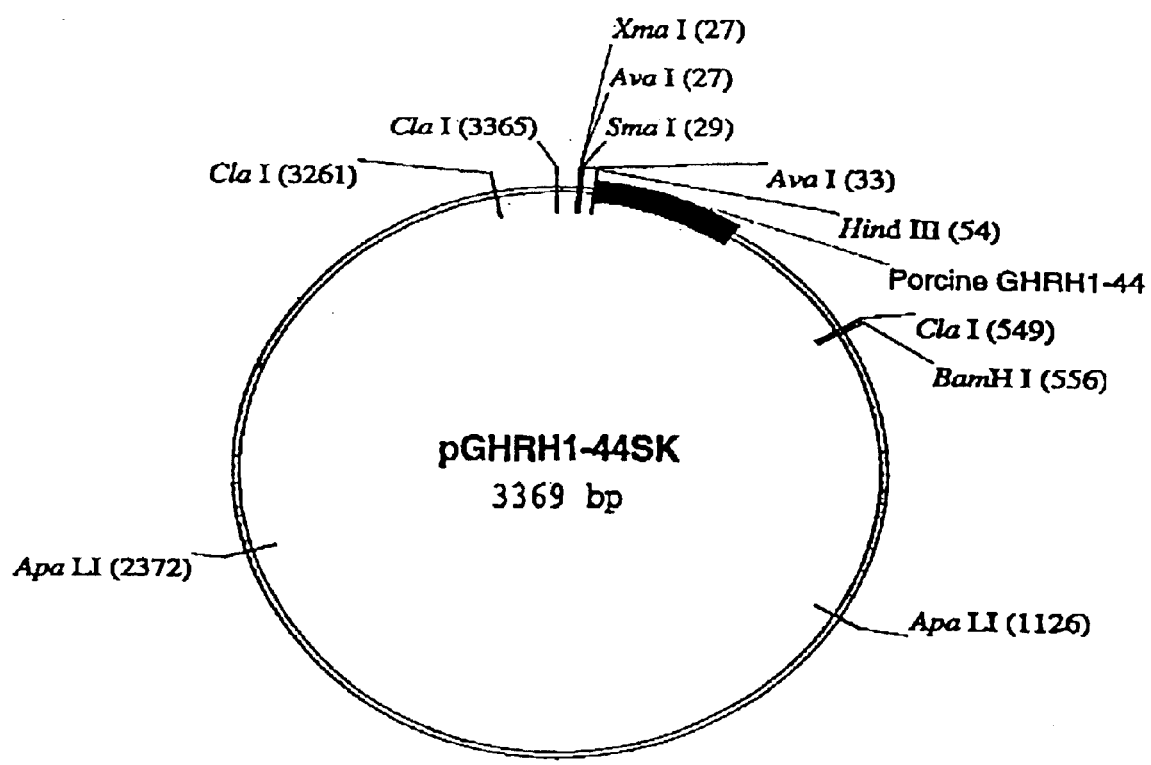
FIG. 2 is a map of the PGHRH1–44SK construct (SEQ ID No. 48).
Figure 3:
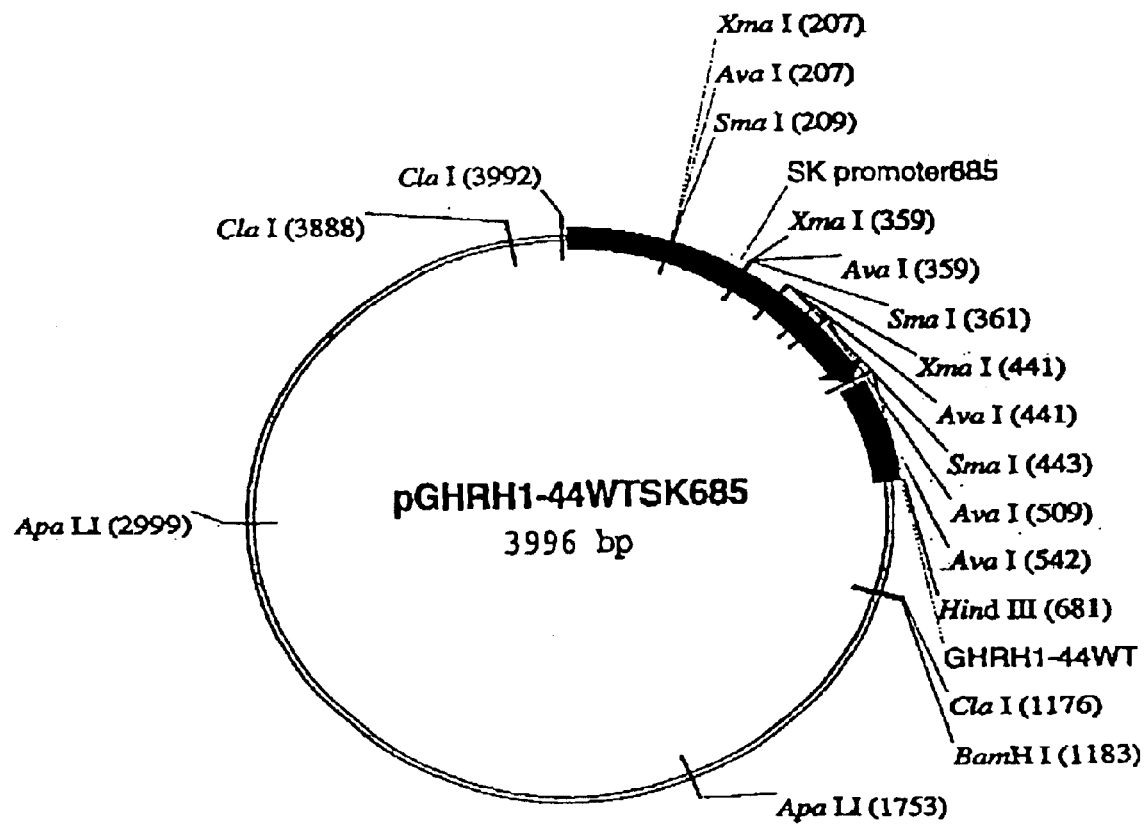
FIG. 3 is a map of the pGHRH1–44WTSK685 construct (SEQ ID No. 49).

The oligonucleotide fragment encoding the 75 amino acid GHRH protein (SEQ ID No. 1) was PCR-amplified from plasmid pGHRH-4 using a primer designated p97-S1 containing a Hind III site SEQ ID No. 4) and a primer designated p97-A258, containing an Xba I site (SEQ ID No. 5). The PCR-amplified sequence was then cloned into the Hind III-Xba I site of plasmid pGL3 basic (Promega) to produce a plasmid designated GHRH1–44 SK (FIG. 2). A 685 bp fragment corresponding to a portion of the porcine α-skeletal actin promoter designated SK685 was PCR-amplified from swine genomic DNA using primer designated SK-3, containing a Kpn I site (SEQ ID No. 6) and primer designated SK-4, containing a Hind III site; (SEQ ID No. 7). The PCR-amplified SK685 promoter fragment was then doned into plasmid GHRH1–44SK digested with Kpn I and HindIII enzymes to produce a plasmid designated GHRH1–44WTSK685 (FIG. 3).

5. pGHRH1–44WTSK2014

A plasmid containing the polynucleotide sequences encoding the 75-amino acid GHRH protein described above operatively linked to a fragment derived from the swine α-skeletal actin promoter approximately 2014 bp (SEQ ID No. 8) was constructed as described below.

Figure 4:
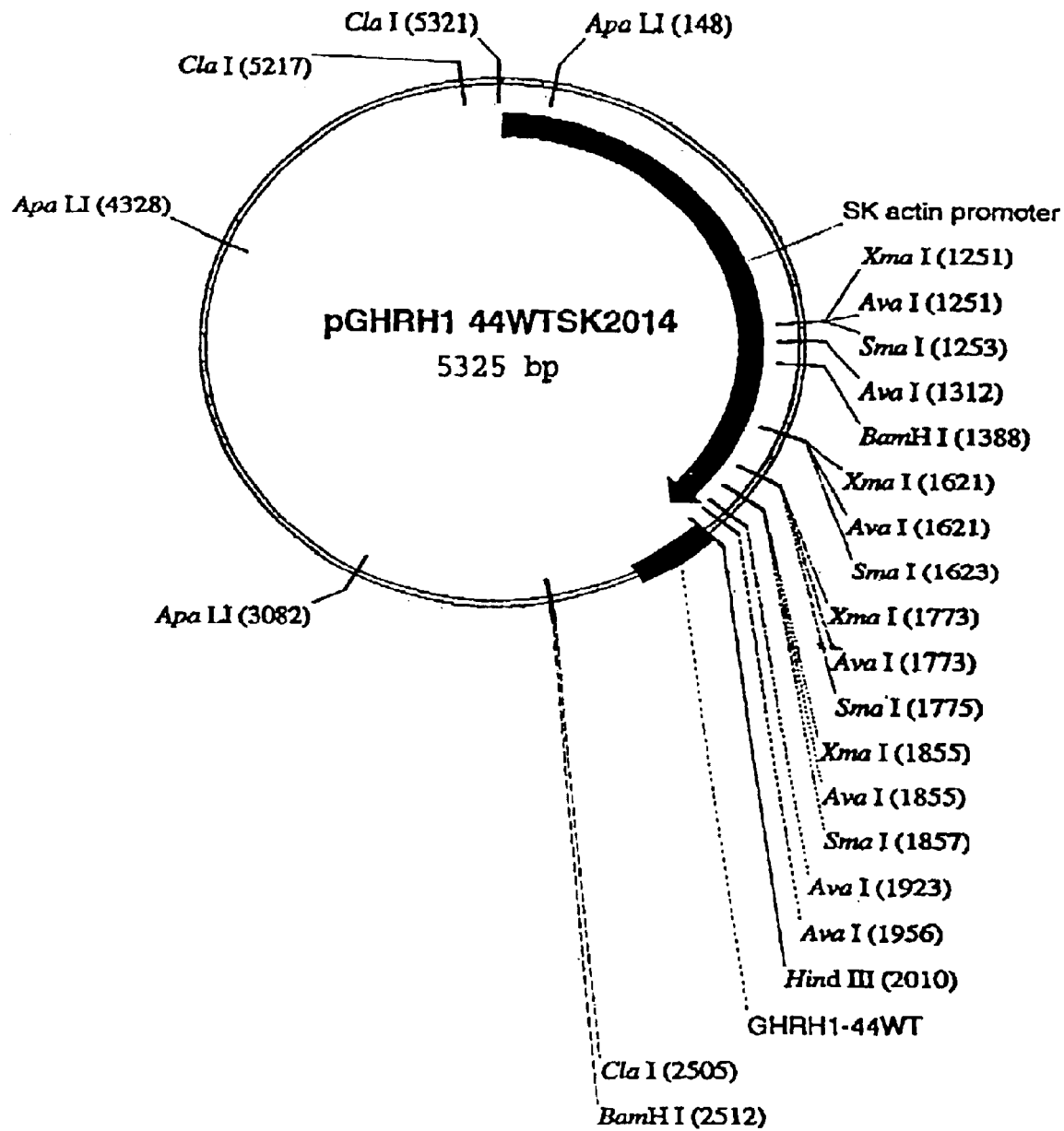
FIG. 4 is a map of the pGHRH1–44WTSK2014 construct (SEQ ID No. 50).

An approximately 2014 bp fragment designated SK 2014 corresponding to a portion of the porcine α-skeletal actin promoter was PCR-amplified from swine genomic DNA using primer designated SK-7; containing a Kpn I site (SEQ ID No. 9) and primer designated SK-8; containing a Hind III site; (SEQ ID No. 10). The PCR-amplified SK2014 promoter fragment was then cloned into plasmid GHRH1–44SK which was digested with Kpn I and Hind III enzymes to produce a plasmid designated GHRH1–44WTSK2014 (FIG. 4).

6. pGHRH1–29WTCMV

A plasmid containing the polynudjeotide sequences encoding the signal sequence derived from human GHRH polynucleotide and encoding amino acids 1–29 of swine GHRH protein was produced as described below.

An approximately 189 bp DNA fragment was PCR-amplified from plasmid pGHRH-4 using primer designated GHRH-5, containing a Bam HI site; (SEQ ID No. 11) and primer designated GHRH-6, containing a Bgl II site; (SEQ ID No. 12). The PCR-amplifled fragment was digested with Bam HI and Bgl II enzymes and cloned into plasmid pVR1012 (Vical, San Diego, Calif.) which was digested with 8am HI and Bgl II enzymes to produce a plasmid designated GHRH1–29WTCMV (SEQ ID No. 51) in which expression of the GHRH 1–29 protein is driven by CMV IE promoter/enhancer sequences.

7. pGHRH1–29YWTCMV

In order to produce novel variants of GHRH protein with enhanced stability to enzymatic degradation (e.g. DPPIV enzyme degradation) a plasmid containing polynucdeotide sequences encoding the signal sequence of human GHRH and an altered version of the 1–29 porcine GHRH protein was produced. The alteration consisted of the addition of an extra tyrosine residue just preceding the first tyrosine residue of the natural porcine GHRH 1–29 sequence. This modification alters the amino terminal in such away that it is no longer recognized or deaved by DPPIV enzyme. A plasmid containing the gene for this variant GHRH protein was produced as described below.

A set of overlapping oligonucleotides (SEQ ID Nos. 13–25) were synthesized, mixed, and GHRH was amplified using the PCR method. The PCR reaction resulted in the formation of a fragment of approximately 192 bp encoding amino acids 1–29 of GHRH in which nucleotides encoding a tyrosine residue were inserted immediately 5' to the coding sequence of GHR(1–29) and further containing a Bam HI site (5' end) and an Bgl II site (3' end ). The 192 bp fragment was then digested with Bam HI and Bgl II enzymes and cloned into plasmid pVR1012 which was digested with Bam HI and Bgl II enzymes to produce plasmid designated GHRH1–29YWTCMV (SEQ ID No. 52) in which expression of GHRH1–29 (now 30) is driven by CMV IE promoter enhancer elements.

8. pGHRH1–29YWTSK685

A plasmid containing the 192 bp fragment described above in Section 5 under the control of the SK685 promoter fragment was produced as described below.

The 192 bp fragment was amplified with two primers designated p99-S1, containing a 5' end Hind III site; (SEQ ID No. 26) and p99-A214, containing a 3' end Xba I site; (SEQ ID No. 27). The PCR-amplified fragment was then digested with Hind III and Xba I enzymes and cloned into plasmid GHRH1–29 Yala1522SK685 (see below) also digested with Hind III and Xba I enzymes to produce plasmid GHRH1–29YWTSK685 (SEQ ID No. 53).

9. pGHRH1–29YWTSK2014

A plasmid containing the 192 bp fragment described above in Section 5 under the control of the SK2014 promoter fragment was produced as described below.

The 192 bp fragment was amplified with two primers designated p99-S1 containing a 5' end Hind III site; (SEQ ID No. 28) and p99-A214 containing a 3' end Xba I site; (SEQ ID No. 29). The PCR-amplified fragment was then digested with Hind III and Xba I enzymes and cloned into plasmid GHRH1–29 YAla 1522SK2014 (see below) also digested with Hind III and Xba I enzymes to produce plasmid GHRH1–29YWTSK2014 (SEQ ID No. 54).

10. pGHRH1–29YAla1522CMV

In order to produce novel variants of GHRH protein with enhanced stability to enzymatic degradation (e.g., due to DPPIV enzyme) and enhanced potency, a plasmid containing the signal sequence of human GHRH and an altered version of the 1–29 porcine GHRH protein was produced. The alteration consisted of the addition of an extra tyrosine residue just preceding the first tyrosine residue of the natural porcine GHRH 1–29 sequence and replacement of glycine 15 and leucine 22 with alanine. These modifications alter the amino terminal end of GHRH1 –29 in such away that it is no longer by recognized or cleaved by the DPP IV enzyme and the modified protein has enhanced potency relative to the 29 or the 44 amino acid GHRH protein. A plasmid containing the gene for this variant protein was produced as described below.

A set of overlapping oligonucleotides were synthesized (SEQ ID Nos. 30–42), mixed and amplified using the PCR method. The PCR reaction resulted in the formation of a fragment of approximately 192 bp containing a Bam HI site (5' end) and an Bgl II site (3' end) and in which an extra three nucleotides encoding for tyrosine is immediately 5' to the nudeotide sequence encoding the natural tyrosine at position 1 of the GHRH1–29 sequence. Furthermore, the alteration included replacement of the 3 nucleotides encoding glycine 15 with three nucleotides encoding alanine and replacement of three nucleotides encoding leucine 22 with three nucleotides encoding alanine. The 192 bp fragment was then digested with Bam HI and Bgl II enzymes and cloned into plasmid pVR1012 which was digested with Bam HI and Bgl II enzymes to produce plasmid designated GHRH1–29YAla 1522CMV in which expression of the variant GHRH1–29

(now 30) is driven by CMV IE promoter enhancer elements (SEQ ID No. 55).

11. pGHRH1–29YAla15225K685

A plasmid containing the GHRH1–29YAla1522 fragment described above under the control of the SK685 promoter fragment was produced as described below.

An approximately 192 bp fragment as described above in Section 8 was PCR-amplified with primers designated p99-S1, containing a Hind III at 5' end (SEQ ID No. 26) and p99-A214 containing a Xba I site at 3' end: (SEQ ID No. 27). The PCR-amplified fragment was digested with Hind III and Xba I enzymes and cloned into plasmid pGL3 (Promega) also digested with Hind III and Xba I to produce plasmid GHRH1–29YAla 1522SK (SEQ ID No. 56). A 685 bp fragment corresponding to a portion of the porcine α-skeletal actin promoter was PCR-amplified from swine genomic DNA using primers SK-3 (Kpn I site) and SK-4 (Hind III site). This fragment was designated SK685. The PCR-amplified SK685 promoter fragment was then cloned into plasmid GHRH1–29YAla1522SK digested with KpnI and HindIII enzymes to produce a plasmid designated GHRH1–29YA1a1522SK685 (SEQ ID No. 57).

12. pGHRH1–29Yala1522SK2014

A plasmid containing the GHRH1–29YAla1522 fragment described above under the control of the SK2014 promoter fragment was produced as described below.

An approximately 192 bp fragment as described above in Section 8 was PCR amplified with primers designated p99-S1 containing a Hind III at 5' end; (SEQ ID No. 26) and p99-A214 containing a Xba I site at 3' end; (SEQ ID No. 27). The PCR-amplified fragment was digested with Hind III and Xba I enzymes and cloned into plasmid pGL3 (Promega) also digested with HindIII and Xba I to produce plasmid GHRH1–29YAla1522SK. An 2014 bp fragment corresponding to a portion of the porcine α-skeletal actin promoter was PCR-amplified from swine genomic DNA using primers SK-7 containing a Kpn I site and SK-8 containing a Hind III site. This fragment was designated SK2014. The PCR-amplified SK2014 promoter fragment was then cloned into plasmid GHRH1–29YAla1522SK digested with Kpn I and Hind III enzymes to produce a plasmid designated GHRH1–29YAla1522SK2014 (SEQ ID No. 58).

13. PGHRH 1–44YWTCMV

In order to produce novel variants of GHRH protein with enhanced stability to enzymatic degradation (e.g., due to DPPIV enzyme) a plasmid containing the signal sequence of human GHRH and an altered version of the 1–44 porcine GHRH protein was produced. The alteration consisting of the addition of an extra tyrosine residue Immediately 5' to the nucleotide sequence encoding the first tyrosine residue of the natural porcine GHRH 1–44 sequence. This modification will alter the amino terminal end in such away that it is no longer by recognized or cleaved by DPPIV enzyme. A plasmid containing the gene for this modified GHRH protein is produced as described below.

A set primers designated GHRH-1 (SEQ ID No. 61) and GHRH-3 (SEQ ID No. 65) were used in a PCR reaction amplify the human GHRH signal sequence and porcine GHRH from pGHRH1–29YWTCMV. The resulting GHRH fragment was digested with Bam HI and Bgl II, and cloned into the Bam HI site of plasmid pVR1012 (Vical, San Diego, Calif.) to produce the plasmid designated GHRH1–44YWTCMV (SEQ ID No. 59).

14. Synthesis of GH Constructs

In order to provide plasmid constructs containing GH genes suitable for treatment of growth hormone maladies or to enhance animal health and productivity, the construction of plasmids of the invention and their methods of use are described below in detail.

The canine GH gene was cloned into plasmids vectors suitable for the various aspects of the present invention using the following procedures. Total RNA was prepared from the pituitary gland of a dog using the RNAzol B method using reagents and procedures from Biotecx Laboratories, Houston Tex. Briefly, about 0.15 mg of the tissue was homogenized in 2 ml of RNAzol B solution in a RNase-free glass homogenizer. The material was then divided into two equal halves, and RNA extracted by chloroform and ethanol precipitation. The nudeic acid pellet was dried and taken up in RNase-free water. Reverse transcription (RT) of total RNA was done in a 20 ml volume using 0.02 mg of RNA, 138 pmol of oligo #2 (SEQ ID No. 43), 1 mM $MnCl_2$, and the recommended amounts of dNTPs and rTth enzyme from the RT-PCR kit purchased from Perkin-Elmer, Norwalk, Conn. The reaction was incubated at 70□ for 11 min in a Perkin-Elmer Thermal cycler. The completed (RT) reaction was then subjected to PCR following addition of 66 pmol of oligo #1 (SEQ ID No. 44), 2.5 mM $MgCl_2$, and chelating buffer from the RT-PCR reaction kit. The PCR conditions were as follows: 94 C, 1 min; 55 C, 1 min; and 72 C, 2 min; for 32 cycles. The □0.7 kb PCR-amplified DNA fragment obtained was cloned into plasmid pCRScript purchased from Stratagene, La Jolla, Calif. and used according to manufacturer's recommendations. The recombinant plasmid thus generated was termed cCG-SP. The insert fragment was partially sequenced and confirmed to contain the growth hormone ("GH") DNA sequences. cGH-SP plasmid DNA was then used as a template to PCR-amplify using oligonucleotides oligo #3 (SEQ ID No. 45) and oligo #4 (SEQ ID No. 46) using reagents from the PCR system kit from Perkin-Elmer using standard procedures and following cycling conditions: 94 C, 1 min 1 cycle; 94 C, 30 sec; 55 C, 30 sec; 72 C, 1 min; 30 cycles. The □0.7 kb PCR-amplified DNA fragment obtained was subjected to column purification (Qiagen, Chatsworth, Calif.), and digested with restriction enzymes EcoRV and BgIII by standard protocols (Sambrook et al., 1989). The digested PCR fragment was ligated to EcoRV-BgIII digested pCMV-MCS, a plasmid derivative of pCMVb (Clontech, Palo Alto, Calif.), engineered to contain multiple cloning sites in place of lacZ gene. The ligation product was used to transform E. coli, and transformants were selected for resistance to ampicillin (pCMV-MCS-enooded marker). Transformants were analyzed by plasmid DNA preparation and restriction site analysis, and a clone of the GH DNA sequences in PCMV-MCS was isolated (termed pCGH#9). The insert sequences were completely sequenced by standard procedures to confirm presence of GH DNA sequences. The EcoRV-BgIII GH fragment from pCGH#9 has also been sub-cloned into gene therapy plasmid VR1012 (obtained from Vical, San Diego, Calif.). This clone referred to as pC51.

15. Synthesis of GH-GHRH Constructs

A GH-GHRH fusion protein, comprising the carboxy terminal 20 amino acids of GH and full length wildtype GHRH is produced. The full length GHRH gene is PCR amplified from plasmid pGHRH-4 using two primers designated GHRH-1 containing a Bgl II site (SEQ ID No. 61) and GHRH-2 containing a Bam HI site (SEQ ID No. 62). The PCR-amplified fragment is then cloned into the Bam HI site of the pVR1012 plasmid. Two complementary oligonucleotides encoding the carboxy terminal amino acids 172–191 of GH (GH-1 oligo.; SEQ ID No. 62 and GH-2 oligo.; SEQ ID No. 63) are synthesized. The GH-1 and GH-2 oligonucleotides are annealed and cloned into the Bam HI site of the pVR1012 plasmid containing the full length GHRH gene to produce pGHRH1–44WTGHpep (SEQ ID No. 60).

16. In Vitro Studies Assessing GHRH Expression Levels

Figure 5:
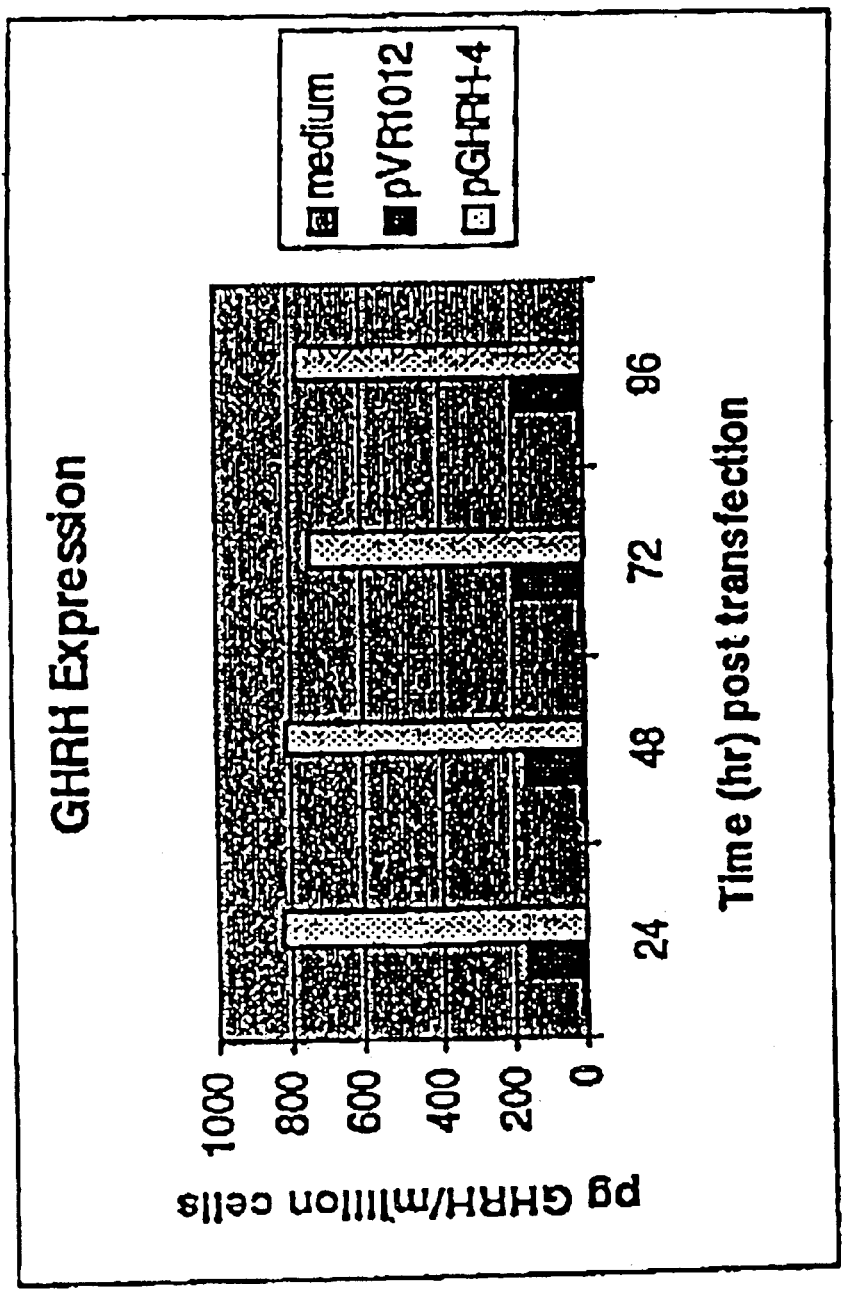
FIG. 5 is a graph depicting the GHRH expression levels detected in supernatants from pGHRH-4 transfected cells.

In order to assess the expression level of GHRH from pGHRH-4, this plasmid or pVR1012 was transfected into C2C12 mouse myoblasts using the fugene reagent according to the manufacturer=s recommendations (Boehringer Ingelheim). Supernatant harvested from transfected and non-transfected cells at various time points were assayed for the presence of GHRH using a commerically available radio-immune assay kit (Pennisula Laboratories). The results depicted in FIG. 5 indicate that GHRH production could be detected 24 hours post-transfection.

17. The Effect of GH Plasmid Injection on Swine Growth

In order to evaluate the effect of a single injection of plasmids containing GH gene on swine growth, experiments addressing the effect GH treatment on swine of different ages were carried out according to the experimental design described below.

Materials & Methods

Thirty six 3-week old (weaned) cross-bred (Yorkshire X landrace) pigs of mixed sex were brought into experimental barns and maintained for an acclimation period of 3 weeks. Animals were kept in pens (2/pen) according to treatment group. Animals were fed daily a non-medicated commercial pig diet ad libitum (16% protein pellet until approximately 45 Kg body weight and then a 14% protein pellet until slaughter) and fresh water was available ad libitum. Animals were randomized into one of four treatment groups (A–D; table 1) according to weight, sex and litter. Eight animals in group A were injected once with plasmids containing GH gene at 6 weeks of age. Controls (10 animals; group C) were injected with blank plasmid vector when they were also 6 weeks of age. Eight animals in group B were injected once with plasmids containing GH gene at 13 weeks of age. Controls (group D; 10 animals) were injected with blank plasmid vector when they were also 13 weeks of age. Food consumption was recorded daily for each pen and animals were weighed on two consecutive days each week until slaughter. Loin eye area and back fat were quantified at slaughter.

TABLE 1

Experimental Design

| Group | Number of Animals | Plasmid dose | Age at time of injection | Weight at time of injection |
| --- | --- | --- | --- | --- |
| A | 8 | 4.6 mg | 6 weeks | 12.4 |
| B | 8 | 4.6 mg | 13 weeks | 4.2 |
| C | 10 | Placebo | 6 weeks | 13.8 |
| D | 10 | Placebo | 13 weeks | 41.9 |

Results

As shown in table 2, treatment of 6 week-old pigs with plasmids encoding GH gene results in enhanced performance. This is evident by the 5% increase in weight gain and 5.1% increase in Average daily gain (ADG) achieved in GH injected animals versus placebo injected pigs. Moreover, the data shows that GH plasmid injection resulted in an improvement of 3.3% in feed efficiency (ratio of feed consumed relative to weight gain) as well as an increase of 7.2% in loin eye area of GH plasmid injected animals.

The data in table 3 shows that treatment of 13 week-old pigs with plasmids encoding GH gene results in an even higher magnitude of increase in animal performance relative to age placebo injected controls than treatment of 6 week-old pigs. This is evident by the 9.5% increase in weight gain and 9.3% increase in Average daily gain (ADG) achieved in GH injected animals versus placebo injected pigs. Moreover, the data shows that GH plasmid injecbon resulted in an improvement of 6.7% in feed efficiency (ratio of feed consumed relative to weight gain) as well as an increase of 6.8% in loin eye area of GH plasmid injected animals. Thus treatment of animals with plasmids containing GH gene results in enhanced animal growth and performance.

TABLE 2

The effect of GH plasmid administration of weight gain

| Group | A | C | % Improvement |
| --- | --- | --- | --- |
| Weight at injection time (Kg) | 12.4 | 13.8 | |
| Weight gain$^a$ | 77.7 | 73.8 | 5.0% |
| ADG$^b$ | .79 | .75 | 5.1% |
| total feed intake/pen$^c$ | 473.3 | 457.6 | 3.4% |
| Feed intake/pen/day$^d$ | 4.8 | 4.7 | 2.1% |
| feed to gain$^e$ | 3.03 | 3.13 | 3.3% |
| Loin eye area at Slaughter (Cm$^2$) | 39.51 | 36.83 | 7.2% |

$^{a \rightarrow e}$= from time of injection to time of slaughter

TABLE 3

The effect of GH plasmid administration of weight gain

| Group | B | D | % Improvement |
| --- | --- | --- | --- |
| Weight at injection time (Kg) | 42.0 | 41.9 | N/A |
| Weight gain$^a$ | 52.1 | 47.6 | 9.5% |
| ADG$^b$ | 1.06 | .97 | 9.3% |
| total feed intake/pen$^c$ | 309.6 | 300.7 | 3.0% |
| Feed intake/pen/day$^d$ | 6.3 | 6.1 | 3.3% |
| feed to gain$^e$ | 3.0 | 3.2 | 6.7% |
| Loin eye area at Slaughter (Cm$^2$) | 41.61 | 38.96 | 6.8% |

$^{a \rightarrow e}$= from time of injection to time of slaughter

A number of references have been cited and the entire disclosures of which are incorporated herein by reference.

The present invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

What is claimed is:

1. A method of increasing the growth of an animal by administering a polynucleotide sequence that encodes a growth hormone releasing hormone, which is operably linked to a swine α-skeletal actin promoter corresponding to SEQ ID NO: 3, directly to the muscle of the animal.

* * * * *